United States Patent
Ruoslahti et al.

(10) Patent No.: US 10,500,246 B2
(45) Date of Patent: Dec. 10, 2019

(54) COMPOSITIONS FOR DELIVERY TO AND TREATMENT OF ATHEROSCLEROTIC PLAQUES

(71) Applicant: Sanford Burnham Prebys Medical Discovery Institute, La Jolla, CA (US)

(72) Inventors: Erkki Ruoslahti, La Jolla, CA (US); Tambet Teesalu, La Jolla, CA (US); Lauri Paasonen, La Jolla, CA (US)

(73) Assignee: Sanford Burnham Prebys Medical Discovery Institute, La Jolla, CA (US)

( * ) Notice: Subject to any disclaimer, the term of this patent is extended or adjusted under 35 U.S.C. 154(b) by 0 days.

(21) Appl. No.: 15/738,000

(22) PCT Filed: Jun. 27, 2016

(86) PCT No.: PCT/US2016/039596
§ 371 (c)(1),
(2) Date: Dec. 19, 2017

(87) PCT Pub. No.: WO2016/210423
PCT Pub. Date: Dec. 29, 2016

(65) Prior Publication Data
US 2018/0303898 A1    Oct. 25, 2018

Related U.S. Application Data

(60) Provisional application No. 62/184,839, filed on Jun. 25, 2015.

(51) Int. Cl.
| | | |
|---|---|---|
| *A61K 38/04* | (2006.01) | |
| *A61K 38/08* | (2019.01) | |
| *A61K 9/107* | (2006.01) | |
| *A61K 31/195* | (2006.01) | |
| *A61K 47/55* | (2017.01) | |
| *A61P 9/10* | (2006.01) | |
| *A61K 47/54* | (2017.01) | |
| *A61K 47/64* | (2017.01) | |

(52) U.S. Cl.
CPC ............ *A61K 38/08* (2013.01); *A61K 9/1075* (2013.01); *A61K 31/195* (2013.01); *A61K 47/55* (2017.08); *A61P 9/10* (2018.01); *A61K 47/543* (2017.08); *A61K 47/643* (2017.08)

(58) Field of Classification Search
None
See application file for complete search history.

(56) References Cited

U.S. PATENT DOCUMENTS

| | | | |
|---|---|---|---|
| 4,016,100 A | 4/1977 | Suzuki | |
| 4,089,801 A | 5/1978 | Schneider | |
| 4,235,871 A | 11/1980 | Papahadjopoulos | |
| 4,485,054 A | 11/1984 | Mezei | |
| 4,745,160 A | 5/1988 | Churchill | |
| 4,853,228 A | 8/1989 | Wallach | |
| 5,013,497 A | 5/1991 | Yiournas | |
| 5,410,016 A | 4/1995 | Hubbell | |
| 5,412,072 A | 5/1995 | Sakurai | |
| 5,449,513 A | 9/1995 | Yokoyama | |
| 5,474,848 A | 12/1995 | Wallach | |
| 5,628,936 A | 5/1997 | Wallach | |
| 5,693,751 A | 12/1997 | Sakurai | |
| 5,820,873 A | 10/1998 | Choi | |
| 5,885,613 A | 3/1999 | Holland | |
| 5,916,596 A | 6/1999 | Desai | |
| 5,925,720 A | 7/1999 | Kataoka | |
| 5,929,177 A | 7/1999 | Kataoka | |
| 6,320,017 B1 | 11/2001 | Ansell | |
| 6,506,405 B1 | 1/2003 | Desai | |
| 6,537,579 B1 | 3/2003 | Desai | |
| 2005/0004002 A1 | 1/2005 | Desai | |
| 2009/0054350 A1 | 2/2009 | Tayot | |
| 2011/0258713 A1* | 10/2011 | Zhu | C12N 5/0696 800/9 |
| 2013/0022328 A1 | 1/2013 | Gronvall | |
| 2013/0115167 A1 | 5/2013 | Ruoslahti | |
| 2016/0039596 A1 | 2/2016 | Nelson | |

FOREIGN PATENT DOCUMENTS

| | | |
|---|---|---|
| WO | 9632434 | 10/1996 |
| WO | 9633233 | 10/1996 |
| WO | 9700623 | 1/1997 |

OTHER PUBLICATIONS

Hamzah, PNAS I Apr. 26, 2011 I vol. 108 I No. 17 I, 7154-59 (Year: 2011).*
Agemy, et al., "Nanoparticle-induced vascular blockade in human prostate cancer", Blood, 116:2847-56 (2010).
Agemy, et al., "Proapoptotic Peptide-Mediated Cancer Therapy Targeted to Cell Surface p32", Molecular Therapy, 21:2195-2204 (2013).
Agemy, et al., "Targeted nanoparticle enhanced proapoptotic peptide as potential therapy for glioblastoma", PNAS, 108(42):17450-5 (2011).
Anthony-Cahill, et al., "Site-specific mutagenesis with unnatural amino acids", TIBS, 14(10):400-3 (1989).
Bangham, et al., "Diffusion of univalent ions across the lamellae of swollen phospholipids", J Mol. Biol., 13:238-52 (1965).
Barenholz, et al., "A new method for preparation of phospholipid vesicles (liposomes)—French press", FEBS Lett., 99:210-4 (1979).
Barile, et al., "NMR-based approaches for the identification and optimization of inhibitors of protein-protein interactions", Chem. Rev., 114:4749-63 (2014).

(Continued)

*Primary Examiner* — Satyanarayana R Gudibande
(74) *Attorney, Agent, or Firm* — Pabst Patent Group LLP

(57) ABSTRACT

Disclosed are compositions and methods for treatment of atherosclerosis and atherosclerotic plaques. In some forms, the compositions and methods can prevent, inhibit, or reduce atherosclerosis. In some forms, the compositions and methods can prevent, inhibit, or reduce atherosclerotic plaques. In particular, compositions comprising a plaque-homing element, a CendR-activating element, and a plaque-inhibiting element are disclosed.

23 Claims, 12 Drawing Sheets

Specification includes a Sequence Listing.

(56) References Cited

OTHER PUBLICATIONS

Batzri, et al., "Single bilayer liposomes prepared without sonication", Biochim et Biophys Acta 298:1015-19 (1973).
Benner, "Expanding the genetic lexicon: incorporating non-standard amino acids into proteins by ribosome-based synthesis", TIB Tech, 12:158-163 (1994).
Bialucha, et al., "p32 is a novel mammalian Lgl binding protein that enhances the activity of protein kinase Cζ and regulates cell polarity", J Cell Biol. 178(4):575-581 (2004).
Braun, et al., "Etchable plasmonic nanoparticle probes to image and quantify cellular internalization", Nature Materials, 13:904-911 (2014).
Brito, et al., "Nanoparticulate carriers for the treatment of coronary restenosis", Int J Nanomedicine. 2(2):143-6 (2007).
Callo, et al., "Thermodynamic modeling and cryomicroscopy of cell-size, unilamellar, and paucilamellar liposomes", Cryobiology, 22(3):251-267 (1985).
Charo and Taub, "Anti-inflammatory therapeutics for the treatment of atherosclerosis", Nat Rev Drug Discov, 10(5):365-376 (2011).
Chatterjee, et al., "N-methylation of peptides and proteins: an important element for modulating biological functions", Angewandte Chemie—International Edition. 52:254-269 (2013).
Deamer, et al., "Large volume liposomes by an ether vaporization method", Biochim et Biophys Acta, 443:629-34 (1976).
Feig, et al., "LXR promotes the maximal egress of monocyte-derived cells from mouse aortic plaques during atherosclerosis regression", J Clinical Investigation., 120(12):4415-4424 (2010).
Finlayson, Seminars in Thrombosis and Hemostasis, 6:85-120 (1980).
Fogal, et al., "Mitochondrial/cell-surface protein p32/gC1qR as a molecular target in tumor cells and tumor stroma", Cancer Res.; 68(17):7210-8 (2008).
Fogal, et al., "Mitochondrial p32 protein is a critical regulator of tumor metabolism via maintenance of oxidative phosphorylation", Mol Cell Biol; 30(6):1303-18 (2010).
Friedman, et al., "The smart targeting of nanoparticles", Curr. Pharm. Des., 19:6315-6329 (2013).
Gershlick, "Treating atherosclerosis: local drug delivery from laboratory studies to clinical trials", Atherosclerosis, 160(2):259-71 (2002).
Ghebrehiwet, et al., "Isolation, cDNA cloning, and overexpression of a 33-kD cell surface glycoprotein that binds to the globular "heads" of C1q", J Exp Med., 179(6):1809-1821 (1994).
Glass and Witztum, "Atherosclerosis. the road ahead", Cell. 104(4):503-516 (2001).
Grefhorst, et al., "Stimulation of lipogenesis by pharmacological activation of the liver X receptor leads to production of large, triglyceride-rich very low density lipoprotein particles", J Biol Chem., 277(37):34182-90 (2002).
Hamzah, et al., "Specific penetration and accumulation of a homing peptide within atherosclerotic plaques of apolipoprotein E-deficient mice", PNAS, 108(17):7154-7159 (2011).
Hauser, et al., "Oxygen transport responses to colloids and crystalloids in critically ill surgical patients", Surgery, Gynecology and Obstetrics, 150:811-816 (1980).
Houston, et al., "Homing markers for atherosclerosis: applications for drug delivery, gene delivery and vascular imaging", FEBS letters., 492(1-2):73-77 (2001).
Hussain, et al., "Quantity and accessibility for specific targeting of receptors in tumours", Sci Rep., 4:5232 (2014).
Ibba and Hennecke, "Towards engineering proteins by site-directed incorporation in vivo of non-natural amino acids", Biotechnology, 12:678-682 (1994).
Ibba, "Strategies for in vitro and in vivo translation with non-natural amino acids", Biotechnology & Genetic Engineering Reviews, 13:197-216 (19956).
Jha, et al., "Disulfide bond formation through Cys186 facilitates functionally relevant dimerization of trimeric hyaluronan-binding protein 1 (HABP1)/p32/gC1qR.", Eu J Biochem., 269 298-306 (2002).

Jiang, et al., "Crystal structure of human p32, a doughnut-shaped acidic mitochondrial matrix protein", PNAS, 96(7):3572-7 (1999).
Joseph, et al., "Synthetic LXR ligand inhibits the development of atherosclerosis in mice", PNAS, 99(11):7604-9 (2002).
Karmali, et al., "Targeting of albumin-embedded paclitaxel nanoparticles to tumors", Nanomed., 5(1):73-82 (2009).
Kim, et al., "Preparation of multivesicular liposomes", Biochim et Biophys Acta 728:339-348 (1983).
Kohori, et al., "Preparation and characterization of thermally responsive block copolymer micelles comprising poly(N-isopropylacrylamide-b-DL-lactide)", J. Control. Rel . . . 55: 87-98, (1998).
Kohori, F. et al., "Control of adriamycin cytotoxic activity using thermally responsive polymeric micelles composed of poly(N-isopropylacrylamide-co-N,N-dimethylacrylamide)-b-poly(d,l-lactide)", Colloids Surfaces B: Biointerfaces, 16:195-205, (1999).
Laakkonen, et al., "A tumor-homing peptide with a targeting specificity related to lymphatic vessels". Nat Med., 8(7):751-755 (2002).
Laakkonen, et al., "Antitumor activity of a homing peptide that targets tumor lymphatics and tumor cells", PNAS, 101(25):9381-9386 (2004).
Labhasetwar, et al., "Arterial uptake of biodegradable nanoparticles: effect of surface modifications", J Pharm Sci., 87(10):1229-34 (1998).
Lea, et al., "Fluorescence polarization assays in small molecule screening", Expert Opinion on Drug Discovery. 6:17-32 (2011).
Leamon, et al., "Folate-mediated targeting: from diagnostics to drug and gene delivery", Drug Discov. Today. 6:44-51 (2001).
Lee and Meisel, "Adsorption and surface-enhanced Raman of dyes on silver and gold sols", J. Phys. Chem.,86:3391-5 (1982).
Liggins and Burt, "Polyether-polyester diblock copolymers for the preparation of paclitaxel loaded polymeric micelle formulations", Adv. Drug Del. Rev., 54:191-202, (2002).
Liu, et al., "In vivo interrogation of the molecular display of atherosclerotic lesion surfaces", Am J Pathology, 163(5):1859-71 (2003).
Luo, et al., "LyP-1-conjugated nanoparticles for targeting drug delivery to lymphatic metastatic tumors", Int. J. Pharm., 385:150-6; (2010).
Matthews and Russell, "Adenovirus core protein V interacts with p32—a protein which is associated with both the mitochondria and the nucleus", J General Virology., 79 (Pt. 7):1677-1685 (1998).
Moghimi, et al., "Long-circulating and target-specific nanoparticles: theory to practice.", Pharm. Rev. 53:283-318 (2001).
Mullick, et al., "Modulation of atherosclerosis in mice by Toll-like receptor 2", J Clin Invest. 115(11):3149-3156 (2005).
Mullick, et al., "Increased endothelial expression of Toll-like receptor 2 at sites of disturbed blood flow exacerbates early atherogenic events", J Experimental Medicine, 205(2):373-83 (2008).
Muta, et al., "p32 Protein, A Splicing Factor 2-associated Protein, Is Localized in Mitochondrial Matrix and Is Functionally Important in Maintaining Oxidative Phosphorylation", J Biol Chem., 272(39):24363370 (1997).
Nahrendorf, et al., "18F-4V for PET-CT imaging of VCAM-1 expression in inflammatory atherosclerosis", JACC Cardiovascular imaging, 2(10):1213-1222 (2004).
Nakai, et al., "Ranking the selectivity of pubchem screening hits by activity based proteins profiling: MMP13 as a case study", Bioorg Med Chem, 17(3):1101-8 (2009).
Owicki, "Fluorescence polarization and anisotropy in high throughput screening: perspectives and primer", J Biomolecular Screening, 5:297-306 (2000).
Paasonen, et al., "New p32/gC1qR Ligands for Targeted Tumor Drug Delivery", Chembiochem17(7):570-575 (2016).
Pang, et al., "A free cysteine prolongs the half-life of a homing peptide and improves its tumor-penetrating activity", J Control Release., 175:48-53 (2014).
Pang, et al., "An endocytosis pathway initiated through neuropilin-1 and regulated by nutrient availability", Nat Commun. 5:4904 (2014b).
Papahadjopoulos, "Phospholipid model ,embranes, 1 Structural cjaracterisrics of hydrated liuid crystals", Biochim et Biophys Acta, 135:624-38 (1967).
Park, et al., "Cooperative nanomaterial system to sensitize, target, and treat tumors", PNAS,. 107 981-986 (2010).

(56) References Cited

OTHER PUBLICATIONS

Park, et al., "Systematic Surface Engineering of Magnetic Nanoworms for in vivo Tumor Targeting", Small. 694-700 (2009).
Peerschke, et al., "Expression of gC1q-R/p33 and its major ligands in human atherosclerotic lesions", Molecular immunology 41(8):759-66 (2004).
Pernot, et al., "Stability of peptides and therapeutic success in cancer", Expert Opin. Drug Metab. Toxicol., 7:793-802 (2011).
Peters, et al., "Targeting atherosclerosis by using modular, multi-functional micelles", PNAS, 106(24):9815-9 (2009).
Pirollo, et al., "Materializing the Potential of Small Interfering RNA via a Tumor-Targeting, Nanodelivery System", Cancer Res., 67:2938-43 (2007).
Reef, et al., "The autophagic inducer smARF interacts with and is stabilized by the mitochondrial p32 protein.", Oncogene. 26(46):6677-83 (2007).
Rizo and Gierasch, "Constrained peptides: models of bioactive peptides and protein substructures", Ann. Rev. Biochem., 61:387-418 (1992).
Roth, et al., "Transtumoral targeting enabled by a novel neuropilin-binding peptide", Oncogene. 31(33):3754-3763 (2012).
Ruoslahti, et al., "Peptides as targeting elements and tissue penetration devices for nanoparticles", Adv Mater. 24 3747-3756 (2012).
Ruoslahti, et al., "Targeting of drugs and nanoparticles to tumors", J Cell Biol., 188(6):759-768 (2010).
Ruoslahti, "Tumor penetrating peptides for improved drug delivery", Adv Drug Deliv Rev. Apr. 1 pii: S0169-409X(16)30094-1 doi: 10.1016/j.addr.2016.03.008; (2017).
Ruusalepp, et al., "A model of neointima formation in the atherosclerotic carotid artery of mice", Interactive cardiovascular and thoracic surgery, 2(2):196-200 (2003).
She, et al., "Clot-Targeted Micellar Formulation Improves Anticoagulation Efficacy of Bivalirudin", ACS Nano. ;8(10):10139-49 (2014).
She, et al., "NG2 proteoglycan ablation reduces foam cell formation and atherogenesis via decreased low-density lipoprotein retention by synthetic smooth muscle cells", Arteriosclerosis, thrombosis, and vascular biolog, 36(1):49-59 (2016).
She, et al., "Human paraoxonase gene cluster transgenic overexpression represses atherogenesis and promotes atherosclerotic plaque stability in ApoE-null mice", Circulation research., 104(10):1160-1168 (2009).
Simberg, et al., "Biomimetic amplification of nanoparticle homing to tumors", PNAS, 104(3):932-6 (2007).
Storz, et al., "Protein Kinase C m Is Regulated by the Multifunctional Chaperon Protein p32", J Biol Chem. ;275(32):24601-24607 (2000).
Sugahara, et al., "Co-administration of a Tumor-Penetrating Peptide Enhances the Efficacy of Cancer Drugs", Science, 328(5981):1031-5 (2010).
Sugahara, et al., "Tissue-penetrating delivery of compounds and nanoparticles into tumors", Cancer Cell. ;16(6):510-520 (2009).
Teesalu, et al., "Mapping of vascular ZIP codes by phage display", Methods Enzymol., 503:35-56 (2012).
Teesalu, et al., "C-end rule peptides mediate neuropilin-1-dependent cell, vascular, and tissue penetration", PNAS, 106(38):16157-16162 (2009).
Thomas, et al., "The road map to oral bioavailability: an industrial perspective", Expert Opinion on Drug Metabolism & Toxicology. 2 591-608 (2004).
Thorson, et al., "1 engh ra and r huber 1991 accurate bond and angle", Methods in Molec. Biol. 77:43-73 (1991).
Tullis, "Albumin. 1. Background and use", JAMA, 237:355-360, 460-463 (1977).
Tuzar, et al., "Block and graft copolymer miclles in solutions", Adv. Colloid Interface Sci., 6:201-232, (1976).
Uchida, et al., "Protein Cage Nanoparticles Bearing the LyP-1 Peptide for Enhanced Imaging of Macrophage-Rich Vascular Lesions", ACS Nano., ;5(4):2493-2502(2010).
Uwatoku, et al., "Application of nanoparticle technology for the prevention of restenosis after balloon injury in rats", Circ Res, 18;92(7):e62-9. Epub (2003).
Vander Kooi, et al., "Structural basis for ligand and heparin binding to neuropilin B domains", PNAS, 104(15):6152-57 (2007).
Waibel, et al., "New Derivatives of Vitamin B12 Show Preferential Targeting of Tumors", Cancer Res., 68 2904-2911(2008).
Wilhelm, et al., "Poly(styrene-ethylene oxide) block copolymer micelle formation in water: a fluorescence probe study", Macromolecules, 24:1033-40 (1991).
Yan, et al., "LyP-1-conjugated PEGylated liposomes: a carrier system for targeted therapy of lymphatic metastatic tumor", J. Controlled Release, 157:118-125 (2012).
Zanuy, et al., "In silico molecular engineering for a targeted replacement in a tumor-homing peptide", J Phys Chem B., 113:7879-89; (2009).
Zanuy, et al., "Engineering strategy to improve peptide analogs: from structure-based computational design to tumor homing", J. Comput. Aided Mol. Des., 27:31-43 (2013).
Zhang, et al., "Development of amphiphilic diblock copolymers as micellar carriers of taxol", Int. J. Pharm., 132:195-206, (1996).

\* cited by examiner

SEQUENCE LISTING

```
<160> NUMBER OF SEQ ID NOS: 25

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1
```

```
Cys Gly Asn Lys Arg Thr Arg Gly Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Cys Gly Gln Lys Arg Thr Arg Gly Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid

<400> SEQUENCE: 3

Cys Xaa Arg Gly Xaa Arg Ser Xaa Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Cys Lys Arg Gly Ala Arg Ser Thr Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Cys Lys Arg Gly Ser Arg Ser Thr Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Cys Lys Arg Gly Asn Arg Ser Thr Cys
```

```
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 7

Gly Asn Lys Arg Thr Arg
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa = any amino acid

<400> SEQUENCE: 8

Arg Gly Xaa Arg Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 9

Cys Lys Arg Gly Ala Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 10

Cys Lys Arg Gly Ser Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Cys Lys Arg Gly Asn Arg
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (3)..(3)
<223> OTHER INFORMATION: Xaa = any amino acid

<400> SEQUENCE: 12

Arg Gly Xaa Arg
1

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid

<400> SEQUENCE: 13

Cys Xaa Arg Gly Xaa Arg
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

Lys Arg Gly Ala Arg
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Lys Arg Gly Ser Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 16

Lys Arg Gly Asn Arg
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
```

```
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 17

Xaa Arg Gly Xaa Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 18

Arg Pro Ala Arg Pro Ala Arg
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 19

Cys Cys Gly Asn Lys Arg Thr Arg Gly Cys
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 20

Cys Arg Glu Lys Ala
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 21

Cys Arg Leu Thr Leu Thr Val Arg Lys Cys
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 22

Asp Pro Arg Ser Phe Leu
1               5

<210> SEQ ID NO 23
<211> LENGTH: 10
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-terminal FAM modification
<220> FEATURE:
<221> NAME/KEY: MISC_FEATURE
<222> LOCATION: (10)..(10)
<223> OTHER INFORMATION: C-terminal NH2 modification

<400> SEQUENCE: 23

Ala Arg Ala Leu Pro Ser Gln Arg Ser Arg
1               5                   10

<210> SEQ ID NO 24
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = arginine, lysine, or histidine
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = arginine, lysine, or histidine

<400> SEQUENCE: 24

Xaa Xaa Xaa Xaa
1

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = arginine, lysine, or histidine
<220> FEATURE:
<221> NAME/KEY: MISC_FEATURE
<222> LOCATION: (2)..(3)
<223> OTHER INFORMATION: Xaa = any amino acid

<400> SEQUENCE: 25

Xaa Xaa Xaa Lys Gly
1               5
```

COMPOSITIONS FOR DELIVERY TO AND TREATMENT OF ATHEROSCLEROTIC PLAQUES

CROSS-REFERENCE TO RELATED APPLICATIONS

This application is a 371 application of PCT/US2016/039596, filed Jun. 27, 2016, which claims priority to and benefit of U.S. Provisional Application No. 62/184,839, filed Jun. 25, 2015. The disclosure of Application No. 62/184,839, filed Jun. 25, 2015, is hereby incorporated herein by reference in its entirety.

STATEMENT REGARDING FEDERALLY SPONSORED RESEARCH

This invention was made with Government support under Grant Nos. R01CA167174 and R01CA152327 awarded by the National Institutes of Health. The Government has certain rights in the invention.

REFERENCE TO SEQUENCE LISTING

The Sequence Listing submitted Dec. 29, 2017, as a text file named "SBMRI_15_024_US_ST25.txt," created on Dec. 28, 2017, and having a size of 5,972 bytes is hereby incorporated by reference pursuant to 37 C.F.R. 1.52(e)(5).

FIELD OF THE INVENTION

The disclosed invention is generally in the field of atherosclerosis and specifically in the area of treatment of atherosclerosis.

BACKGROUND OF THE INVENTION

Strategies to prevent the formation of plaque and to resolve existing plaque are urgently needed to treat atherosclerosis, the primary cause of heart disease and stroke, and the most common cause of morbidity and mortality worldwide. The existing means of intervention provide substantial benefits to patients with atherosclerosis, but side effects and limited access of therapeutic agents to plaque interior remain major obstacles to success of such therapies (Charo and Taub, Nat Rev Drug Discov. 2011; 10(5):365-376).

Specific molecular signatures distinguish the endothelium covering atherosclerotic plaques from normal endothelium. These signatures can be used to target diagnostics and therapeutics to plaque. Drugs coupled to a homing molecule, such as a peptide, become concentrated at the target tissue (synaphic or active targeting), resulting in increased efficacy and/or decreased side effects (reviewed in Ruoslahti et al., J Cell Biol. 2010; 188(6):759-768). One plaque marker is VCAM-1, which can be engaged with antibodies and a peptide ligand (e.g., Nahrendorf et al., JACC Cardiovascular imaging. 2009; 2(10):1213-1222). In vivo phage display has been used in search for additional markers of plaques, and peptides that selectively recognize the endothelium over plaques have been reported (Houston et al., FEBS letters. 2001; 492(1-2):73-77; Liu et al., American J Pathology. 2003; 163(5):1859-1871). The binding molecules (receptors) for these peptides have not been identified.

The clot-binding peptide CREKA (Simberg et al., Proc Natl Acad Sci USA. 2007; 104(3):932-936) has been used to target the subtle clotting that occurs on the surface of atherosclerotic plaques (Peters et al., Proc Natl Acad Sci USA. 2009; 106(24):9815-9819). CREKA also homes to tumors (Simberg et al., Proc Natl Acad Sci USA. 2007; 104(3):932-936). Another tumor-homing peptide, LyP-1, can home to the surface of plaques, penetrate into the plaque interior, and accumulate there (Hamzah et al., Proc Natl Acad Sci USA. 2011; 108(17):7154-7159).

LyP-1 is a cyclic nonapeptide that specifically recognizes lymphatic vessels, macrophages, and tumor cells in certain tumors; it shows no binding to any normal tissues (Fogal et al., Cancer Res. 2008; 68(17):7210-7218; Laakkonen et al., Proc Natl Acad Sci USA. 2004; 101(25):9381-9386; Laakkonen et al., Nat Med. 2002; 8(7):751-755). The primary receptor for the LyP-1 peptide is p32/p33/gC1qR/HABP1 (p32; Fogal et al., Cancer Res. 2008; 68(17):7210-7218). Numerous extracellular and intracellular proteins, and even hyaluronic acid have been reported to bind to p32; indeed, p32 may be a multifunctional chaperone (Bialucha et al., J Cell Biol. 2007; 178(4):575-581; Storz et al., J Biol Chem. 2000; 275(32):24601-24607). Crystallography shows p32 as a doughnut-shaped trimer (Jiang et al., Proc Natl Acad Sci USA. 1999; 96(7):3572-3577). The main location of p32 is in the mitochondria (Matthews and Russell, J General Virology. 1998; 79 (Pt. 7):1677-1685), but other subcellular locations have been reported, including the cell surface (Ghebrehiwet et al., J Experimental Medicine. 1994; 179 (6):1809-1821). The mitochondrial and cell surface localization has been confirmed (Fogal et al., Cancer Res. 2008; 68(17):7210-7218; Laakkonen et al., Proc Natl Acad Sci USA. 2004; 101(25):9381-9386; Laakkonen et al., Nat Med. 2002; 8(7):751-755). In yeast (Muta et al., J Biol Chem. 1997; 272(39):24363-24370) and mammalian cells (Fogal et al., Mol Cell Biol. 2010; 30(6):1303-1318), p32 regulates mitochondrial oxidative phosphorylation. A link to autophagy has been proposed (Reef et al., Oncogene. 2007; 26(46):6677-6683). Elevated expression of p32 has been noted in cancer (Fogal et al., Cancer Res. 2008; 68(17): 7210-7218) and in atherosclerotic plaques (Hamzah et al., Proc Natl Acad Sci USA. 2011; 108(17):7154-7159; Peerschke et al., Molecular immunology. 2004; 41 (8):759-766).

It is an object of the present invention to provide compositions for treatment of atherosclerosis.

It is a further object of the present invention to provide compositions for prevention, inhibition, or reduction of atherosclerosis.

It is a further object of the present invention to provide compositions for treatment of atherosclerotic plaques.

It is a further object of the present invention to provide compositions for prevention, inhibition, or reduction of atherosclerotic plaques.

It is a further object of the present invention to provide methods for treatment of atherosclerosis.

It is a further object of the present invention to provide methods for prevention, inhibition, or reduction of atherosclerosis.

It is a further object of the present invention to provide methods for treatment of atherosclerotic plaques.

It is a further object of the present invention to provide methods for prevention, inhibition, or reduction of atherosclerotic plaques.

BRIEF SUMMARY OF THE INVENTION

Disclosed are compositions and methods for treatment of atherosclerosis and atherosclerotic plaques. In some forms, the compositions and methods can prevent, inhibit, or reduce atherosclerosis. In some forms, the compositions and methods can prevent, inhibit, or reduce atherosclerotic plaques.

Disclosed are compositions comprising a plaque-homing element, a CendR-activating element, and a plaque-inhibiting element. The plaque-homing element can be the same as, overlap with, be coupled to, or be conjugated to the CendR-activating element. The plaque-inhibiting element can be the same as, overlap with, be coupled to, be conjugated to, or be not covalently coupled or directly non-covalently associated with the plaque-homing element, the CendR-activating element, or both.

In some forms, the plaque-homing element can bind to p32. In some forms, the plaque-homing element can be a peptide or a small molecule compound. In some forms, the plaque-homing element can be CGNKRTRGC (SEQ ID NO: 1), CGQKRTRGC (SEQ ID NO:2), $CX_aRGX_bRSX_cC$ (SEQ ID NO:3), CKRGARSTC (SEQ ID NO:4), CKRGSRSTC (SEQ ID NO:5), or CKRGNRSTC (SEQ ID NO:6). $X_a$, $X_b$, and $X_c$ independently can be any amino acid.

In some forms, the plaque-homing element can be a compound having the structure of Formula I:

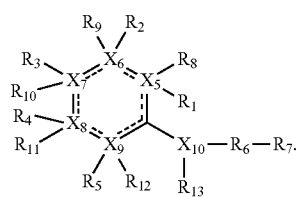

Formula I $X_5$, $X_6$, $X_7$, $X_8$, and $X_9$ can independently be C, N, S, or O. In some forms, at least one of $X_5$, $X_6$, $X_7$, $X_8$, and $X_9$ is C or N. In some forms, at least one of $X_5$, $X_6$, $X_7$, $X_8$, and $X_9$ is N.

$R_1$, $R_2$, $R_3$, $R_4$, and $R_5$ can independently be hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, or absent if valency requires. In some forms, at least one of $R_1$, $R_2$, $R_3$, $R_4$, and $R_5$ is substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

$R_8$, $R_9$, $R_{10}$, $R_{11}$, $R_{12}$, and $R_{13}$ can independently be absent, hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

In some forms, $X_9$, $R_5$, and $R_{12}$ together can be absent, thus forming a 5-membered ring.

$X_{10}$ can be N, O, or S.

$R_6$ can be —$(CH_2)_n$— or —$(CH_2)_n$—$CHR_{14}$—$(CH_2)_m$—, or —$(CH_2)_n$—O—$(CH_2)_m$—, where n and m are independently 1, 2, 3, 4, 5, 6, 7, 8, 9, 10, and where $R_{14}$ is halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

$R_7$ can be —$NR_{15}R_{16}$, where $R_{15}$ is hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl, and where $R_{16}$ is hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, or a group having the structure of Formula II:

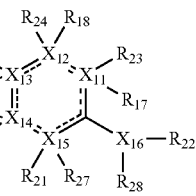

Formula II $X_{11}$, $X_{12}$, $X_{13}$, $X_{14}$, and $X_{15}$ can independently be C, N, S, or O. In some forms, at least one of $X_{11}$, $X_{12}$, $X_{13}$, $X_{14}$, and $X_{15}$ is C or N. In some forms, at least one of $X_{11}$, $X_{12}$, $X_{13}$, $X_{14}$, and $X_{15}$ is N.

$R_{17}$, $R_{18}$, $R_{19}$, $R_{20}$, and $R_{21}$ can independently be hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, or absent if valency requires. In some forms, at least one of $R_{17}$, $R_{18}$, $R_{19}$, $R_{20}$, and $R_{21}$ can be substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

$R_{23}$, $R_{24}$, $R_{25}$, $R_{26}$, $R_{27}$, and $R_{28}$ can independently be absent, hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —CF$_3$, —CN, or substituted or unsubstituted C$_1$-C$_{10}$ alkyl, C$_1$-C$_{10}$ alkylene, C$_2$-C$_{10}$ alkenyl, C$_2$-C$_{10}$ alkynyl, C$_1$-C$_{10}$ alkoxy, C$_1$-C$_{10}$ alkylamino, C$_1$-C$_{10}$ alkylthio, C$_1$-C$_{10}$ carbonyl, C$_1$-C$_{10}$ carboxyl, C$_1$-C$_{10}$ amido, C$_1$-C$_{10}$ sulfonyl, C$_1$-C$_{10}$ sulfonic acid, C$_1$-C$_{10}$ sulfamoyl, C$_1$-C$_{10}$ sulfoxide, C$_1$-C$_{10}$ phosphoryl, or C$_1$-C$_{10}$ phosphonyl.

In some forms, X$_{15}$, R$_{21}$, and R$_{27}$ together can be absent, thus forming a 5-membered ring.

X$_{16}$ can be N, O, or S.

R$_{22}$ can be —(CH$_2$)$_j$— or —(CH$_2$)$_j$—CHR$_{29}$—(CH$_2$)$_k$—, or —(CH$_2$)$_j$—O—(CH$_2$)$_k$—, where j and k are independently 1, 2, 3, 4, 5, 6, 7, 8, 9, 10, and where R$_{29}$ is halogen, azide, hydroxyl, amino, thiol, oxo, phosphate, nitro, nitrile, imino, amido, phosphonate, phosphinate, silyl, ether, ketone, aldehyde, ester, heterocyclyl, —CF$_3$, —CN, or substituted or unsubstituted C$_1$-C$_{10}$ alkyl, C$_1$-C$_{10}$ alkylene, C$_2$-C$_{10}$ alkenyl, C$_2$-C$_{10}$ alkynyl, C$_1$-C$_{10}$ alkoxy, C$_1$-C$_{10}$ alkylamino, C$_1$-C$_{10}$ alkylthio, C$_1$-C$_{10}$ carbonyl, C$_1$-C$_{10}$ carboxyl, C$_1$-C$_{10}$ amido, C$_1$-C$_{10}$ sulfonyl, C$_1$-C$_{10}$ sulfonic acid, C$_1$-C$_{10}$ sulfamoyl, C$_1$-C$_{10}$ sulfoxide, C$_1$-C$_{10}$ phosphoryl, or C$_1$-C$_{10}$ phosphonyl.

In some forms, the plaque-homing compound can be a pharmaceutically acceptable salt or ester of the compound.

In some forms of the plaque-homing compound, R$_1$ is —CH$_3$, R$_2$, R$_4$, R$_5$, R$_{15}$, R$_{16}$, and R$_{17}$ are hydrogen, R$_3$ and R$_8$-R$_{12}$ are absent, R$_6$ is —(CH$_2$)$_n$—, n is 2, R$_7$ is —NR$_{15}$R$_{16}$, R$_{15}$ and R$_{16}$ are hydrogen, X$_5$, X$_6$, X$_8$, and X$_9$ are C, and X$_7$ and X$_{10}$ are N.

In some forms of the plaque-homing compound, R$_7$ is a group having the structure of Formula II, R$_1$, R$_4$, R$_5$, R$_8$-R$_{12}$, R$_{17}$, R$_{20}$, R$_{21}$, and R$_{23}$-R$_{27}$ are absent, R$_3$, R$_{10}$, R$_{19}$, and R$_{25}$ are —CH$_3$, R$_2$, R$_{13}$, R$_{18}$, and R$_{28}$ are hydrogen, R$_6$ is —(CH$_2$)$_n$—, n is 1, X$_5$, X$_{10}$, X$_{11}$, and X$_{16}$ are N, X$_6$, X$_7$, X$_{12}$, and X$_{13}$ are C, X$_8$ and X$_{14}$ are S, X$_9$ and X$_{15}$ are absent, R$_{22}$ is —(CH$_2$)$_j$—, and j is 1.

In some forms, the CendR-activating element can bind to NRP-1, NRP-2, or both. In some forms, the CendR-activating element can be a peptide or a small molecule compound. In some forms, the CendR-activating element can be CGNKRTRGC (SEQ ID NO:1), CGQKRTRGC (SEQ ID NO:2), GNKRTR (SEQ ID NO:7), CX$_a$RGX$_b$RSX$_c$C (SEQ ID NO:3), CKRGARSTC (SEQ ID NO:4), CKRGSRSTC (SEQ ID NO:5), CKRGNRSTC (SEQ ID NO:6), CKRGAR (SEQ ID NO:9), CKRGSR (SEQ ID NO:10), CKRGNR (SEQ ID NO:11), CX$_a$RGX$_b$R (SEQ ID NO:13), KRGAR (SEQ ID NO:14), KRGSR (SEQ ID NO:15), KRGNR (SEQ ID NO: 16), RGX$_b$R (SEQ ID NO:12), X$_a$RGX$_b$R (SEQ ID NO: 17), RPARPAR (SEQ ID NO:18), or a peptide with the sequence X$_1$X$_2$X$_3$X$_4$ at, or exposable at, the free C-terminal end of the peptide, where X$_1$ is R, K or H, where X$_4$ is R, K, H, or KG, and where X$_2$ and X$_3$ are each, independently, any amino acid.

In some forms, the plaque-inhibiting element can be a peptide or a small molecule compound. In some forms, the plaque-inhibiting element can be CGNKRTRGC (SEQ ID NO:1), CGQKRTRGC (SEQ ID NO:2), CKRGARSTC (SEQ ID NO:4), CKRGSRSTC (SEQ ID NO:5), or CKRGNRSTC (SEQ ID NO:6).

In some forms, the plaque-inhibiting element can be GW3965.

In some forms, the plaque-inhibiting element can promote apoptosis of a cell in which it is internalized. In some forms, the plaque-inhibiting element can bind p32.

In some forms of the composition, one or more of the plaque-homing element, CendR-activating element, and plaque-inhibiting element can be a peptide. In some forms, one or more of the one or more plaque-homing element, CendR-activating element, and plaque-inhibiting element that is a peptide can conjugate to albumin in blood. In some forms, one or more of the one or more plaque-homing element, CendR-activating element, and plaque-inhibiting element that is a peptide can be conjugated to a lipid. In some forms, one or more of the plaque-homing element, CendR-activating element, and plaque-inhibiting element can be coupled to a lipid. In some forms, the composition is comprised in a micelle. For example, one or more of the components can be couple to a lipid and the component/lipid can then be formed into a micelle. Other components can be enclosed in the micelle or coupled to the first component, the same lipid, or to a different lipid.

In some forms, one or more of the one or more plaque-homing element, CendR-activating element, and plaque-inhibiting element that is a peptide can be conjugated to nanoparticle. In some forms, one or more of the plaque-homing element, CendR-activating element, and plaque-inhibiting element can be coupled to a nanoparticle.

In some forms of the composition, one or more of the plaque-homing element, CendR-activating element, and plaque-inhibiting element can be an extended blood half-life peptide. An extended blood half-life peptide is one that includes a feature that increases the half-life of the peptide in blood over the half-life in blood of the same peptide without that feature. In some forms, the extended blood half-life peptide is a peptide that can conjugate to albumin in blood. In some forms, the extended blood half-life peptide is a peptide conjugated to a lipid. In some forms, the extended blood half-life peptide is a stabilized peptide. A stabilized peptide is a peptide that is modified to make it less susceptible to proteolytic cleavage, such as by including reduced peptide bonds or N-methylated amino acids.

In some forms of the composition, the plaque-homing element, the CendR-activating element, and plaque-inhibiting elements are collectively comprised in an extended blood half-life LyP-1 peptide. In some forms, the extended blood half-life LyP-1 can comprise CCGNKRTRGC (SEQ ID NO: 19), CGNKRTRGC (SEQ ID NO: 1) tethered to a cysteine, CGNKRTRGC (SEQ ID NO: 1) conjugated to a lipid. In some forms, the extended blood half-life LyP-1 comprises a lipid coupled to CGNKRTRGC (SEQ ID NO:1).

Also disclosed are methods of treating atherosclerosis in a subject by administering one or more of the disclosed compositions. In some forms, the subject is at risk of atherosclerosis. In some forms, the subject has atherosclerosis.

Also disclosed are methods of identifying and methods of assessing compounds that can bind p32, can bind NRP-1, NRP-2, or both, can inhibit atherosclerotic plaques, or a combination. Also disclosed are methods of identifying and methods of assessing compounds that can home to or target plaques, can activate the CendR pathway, can promote the CendR bystander effect, can inhibit atherosclerotic plaques, or a combination.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1A:
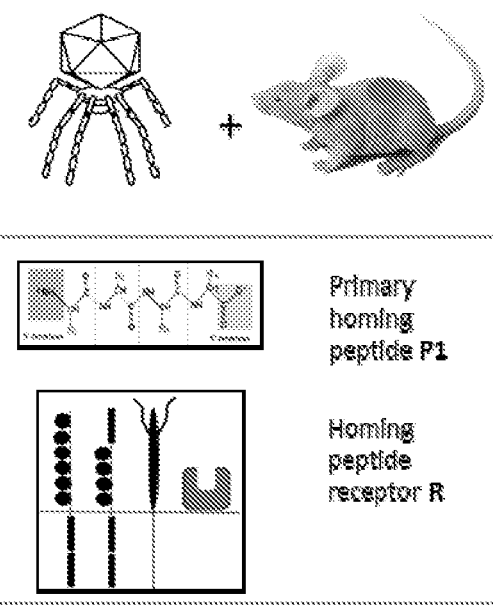
FIGS. 1A, 1B, and 1C are diagrams showing multistep development of systemic homing compounds using reiterative biopanning and FP-based screening. (A) In vivo phage display is used for mapping of systemically accessible diversity of vascular beds. It yields primary homing peptides that can be used for biochemical identification of binding partners, "receptors." (B) In vitro biopanning on purified receptors is used for identification of secondary receptors of improved binding properties. (C) Fluorescence polarization assays are used for high-throughput screening of compounds that bind to peptide binding site on target receptors. Emitted fluorescence polarization increases as the FAM-labeled peptide binds to its partner protein and the rotation slows down. Below: in the presence of competitor compound increased concentration of free fast-rotating FAM-labeled peptide is seen as decrease in fluorescence polarization.
Figure 1B:
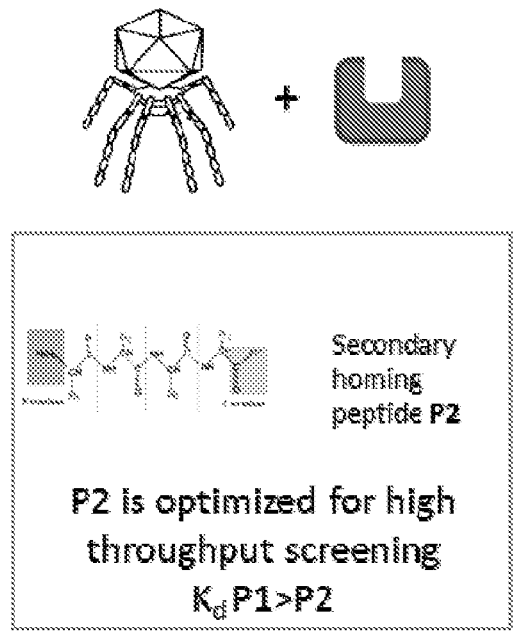

The disclosed method and compositions may be understood more readily by reference to the following detailed description of particular embodiments and the Example included therein and to the Figures and their previous and following description.

p32 is a mitochondrial protein that in certain activated cells is also present at the cell surface. The cell surface p32 serves as a target for a 9-amino acid cyclic peptide, LyP-1, which was originally described as a tumor-homing peptide. More recently, LyP-1 has also been shown to specifically recognize atherosclerotic plaques and promote the delivery of imaging contrast agents to plaques. LyP-1 does not accumulate in any normal tissue. In addition to homing specifically to the sites of plaque, LyP-1 penetrates into the interior of the plaques. The ability to penetrate into target tissue is due to activation by LyP-1 and similar peptides of an endocytic transport pathway that is related to but distinct from macropinocytosis. These peptides accomplish the pathway activation through a complex process that involves binding to a primary, tissue-specific receptor, a proteolytic cleavage, and binding to a second receptor. The second receptor, neuropilin-1 (or neuropilin-2) activates the transport pathway. This trans-tissue pathway, dubbed the CendR pathway, mediates the extravasation and transport through extravascular tissue of payloads ranging from small molecule drugs to nanoparticles. In plaques, the peptide and its payload mainly accumulate in plaque macrophages.

It has been discovered that prolonged systemic treatment with the LyP-1 peptide alone, with no drug, reduces plaque load in ApoE mice. The mechanism appears to be selective apoptosis of the cells in which the peptide accumulates (mainly plaque macrophages). This discovery allows the treatment of treatment of atherosclerosis using peptides and other agents that produce the effect on plaques seen with LyP-1. Disclosed are LyP-1 peptides and variants with increased half-life of the peptide in the circulation. Also disclosed are compounds that produce the anti-plaque activity of LyP-1. The disclosed peptides and compounds can be used to treat atherosclerosis directly, can be used to concentrate systemically administered drugs in plaques, or a combination. The disclosed peptides, compounds, compositions, and methods allow treatments utilizing direct local suppression of plaque formation and selective drug delivery into plaques.

The homing peptide LyP-1 specifically accumulates in atherosclerotic plaques, arterial inflammatory lesions, and tumors, where it primarily recognizes activated macrophage/myeloid lineage cells (Fogal et al., Cancer Res. 2008; 68(17):7210-7218; Hamzah et al., Proc Natl Acad Sci USA. 2011; 108(17):7154-7159; Laakkonen et al., Nat Med. 2002; 8(7):751-755; Uchida et al., ACS Nano. 2011; 5(4):2493-2502). The homing of LyP-1 to these lesions is specific; LyP-1 does not accumulate in normal tissues. The target molecule (receptor) for LyP-1 is p32/gC1qR/HABP (p32), a protein that is intracellular (mostly mitochondrial) in many types of cells, but that is expressed at the cell surface only in highly activated cells. Such cells include the endothelial cells coating plaques and plaque macrophages and various types of cells in tumors, but not in normal cells.

The cell surface expression of p32 makes it a plaque-specific (and tumor-specific) target. It was discovered that LyP-1 can deliver imaging agents into atherosclerotic plaques and carotid inflammatory lesions, allowing enhanced imaging of the lesions (Hamzah et al., Proc Natl Acad Sci USA. 2011; 108(17):7154-7159; Uchida et al., ACS Nano. 2011; 5(4):2493-2502). It was also discovered that LyP-1 possesses a biological activity beyond the homing and carrier functions; treatment with this peptide also has a direct plaque-reducing effect. The molecular mechanism of this activity appears to be LyP-1-induced apoptosis in plaque macrophages. The disclosed peptides, compounds, compositions, and methods utilize this discovery to treat atherosclerosis.

The targeting of p32 by LyP-1 and the disclosed peptides is particularly useful because: (1) p32 is expressed at elevated levels in plaques and is present at the cell surface of plaque cells, plaque macrophages in particular; (2) the LyP-1 peptide is highly effective in homing to plaques because it binds to p32, is internalized into the target cells, and penetrates into the interior of plaques (Hamzah et al., Proc Natl Acad Sci USA. 2011; 108(17):7154-7159); and (3) LyP-1 has a pharmacological activity of its own; it reduces macrophage content and size of plaques, inhibiting atherosclerosis progression. The molecular basis of the anti-atherosclerosis activity of LyP-1 is not entirely clear, but a pro-apoptotic effect on plaque macrophages is likely to underlie the activity. In addition to the utility of this inherent activity of LyP-1, LyP-1 and the other disclosed peptides can be used for selective delivery of drugs into plaques.

The circulation half-life of peptides can be prolonged by engineering them to conjugate with albumin in the blood, or by coating the peptide onto nanoparticles. These modifications have been shown to enhance some peptide activities in vivo. Compounds that specifically bind to p32, and do so at the same site as LyP-1, are described.

CendR motif peptides specifically increase tumor accumulation of co-administered drugs, in many cases without requiring any linkage between the two molecules (a so-called "bystander" effect). This effect can be used in some forms of the disclosed peptides for plaque-targeted drug delivery. This activity allows using the disclosed peptides for a dual purpose, to elicit the effect of the peptide on plaque development and to enhance the accumulation of a drug in plaques.

The disclosed compounds, which affect plaques analogously to the LyP-1 peptide, result in atherosclerosis therapies that use systemic pharmacological intervention to prevent or reverse plaque formation by acting directly on the plaques.

It is not required that all three of the Lyp-1 activities (plaque-homing, CendR-activating, and plaque-inhibiting) be embodied in a single peptide or compound. It was recognized that different peptides and/or compounds having different of these activities can be combined in the same composition. And it was recognized that each of the separate components can have a higher level of activity than Lyp-1, thus providing a composition with higher activity, usefulness, and effectiveness. Small molecule compounds, even if they are not themselves CendR-activating, can passively enter cells or internalization can be mediated by including a separate CendR-activating peptide or compound in the composition. An example of an NRP-1-binding compound has been identified. Such a CendR-activating compound can be coupled to a p32-binding compound, such as #008, to provide a conjugate that both homes to plaques and stimulates internalization into plaque cells (and reproduce the homing and tissue penetration effects of LyP-1).

Figure 9:
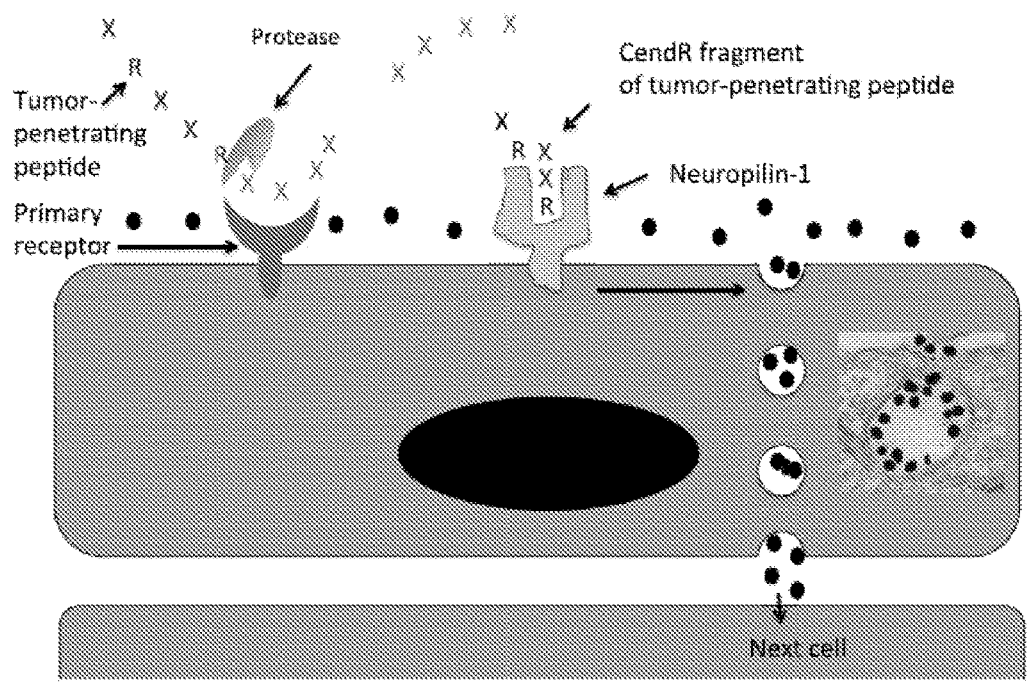
FIG. 9 is a schematic representation of the CendR trans-tissue transport pathway. CendR effect enhances the tissue penetration of cargo that is coupled to a CendR peptide, as well as cargo that is co-administered with it, without any chemical linkage (Sugahara et al., Cancer Cell. 2009; 16(6): 510-520; Sugahara et al., Science 2010; 328(5981):1031-1035). The inset is an EM picture of CendR peptide-coated gold NPs taken up into a macropinocytotic vesicle (Pang et al., Nat Commun. 2014a; 5:4904).

CendR peptides activate an endocytic trans-tissue transport pathway in cells, allowing coupled and co-injected compounds to extravasate and penetrate into tumor tissue (see, for example, Ruoslahti, Adv Drug Deliv Rev. 2016 Apr. 1 pii: S0169-409X(16)30094-1 doi: 10.1016/j.addr.2016.03.008; Sugahara et al., Science 2010; 328 (5981):1031-1035). FIG. 9 illustrates the principle and gives an example of what the endocytic vesicles look like viewed by electron microscopy (Pang et al., Nat Commun. 2014a; 5:4904). The non-conjugated delivery ("by-stander effect") has greater potential than coupling of the peptide to the payload for several reasons: First, the fact that the drug to be delivered does not have to be chemically altered is a major advantage from the translational point of view because it would not be necessary to create a new chemical entity. Yet, more of a drug (or diagnostic probe) could be delivered into plaques than in a standard regimen, which means better efficacy and/or reduced side effects. Second, the plaque penetration effect makes it possible to deliver drugs that ordinarily would not reach the plaque interior. Third, the co-injection-based targeting can circumvent a major limitation of synaphic (ligand-directed) targeting, that the maximum capacity of the delivery is limited by the availability of receptors for the targeting probe. While targeting may greatly enhance the concentration and activity of a drug at the target tissue, the effect is strongest at low concentrations of the drug and tends to disappear when higher doses are used (e.g., Ruoslahti et al., J Cell Biol. 2010; 188(6):759-768). The apparent reason is that the receptors at the target can only handle so much targeted compound, and any excess fails to benefit from the targeting (Hussain et al., Sci Rep. 2014; 4:5232). The co-injection/CendR system circumvents this limitation because it is based on a bulk transport mechanism, and the peptide receptor is only used for the activation of the system.

A. Definitions

As used herein, a small molecule compound is an organic and organometallic compounds having a molecular weight of less than about 2500 g/mol. Preferably, small molecule compounds have a molecular weight of less than about 2000 g/mol, more preferably less than about 1500 g/mol, and most preferably less than about 1200 g/mol. Preferably the small molecule compound is organic. The small molecule compound can be a hydrophilic, hydrophobic, or amphiphilic compound and includes salts of the compound, including pharmaceutically acceptable salts of the compound, or an ester of the compound.

The disclosed peptides, compounds, and methods were developed based on LyP-1, a cyclic, 9-amino acid peptide (CGNKRTRGC; SEQ ID NO: 1) that specifically homes to atherosclerotic plaques (and to tumors) and penetrates into the target tissue. The receptor for LyP-1 is cell surface-expressed p32 protein (Fogal et al., Cancer Res. 2008; 68(17):7210-7218; Laakkonen et al., Proc Natl Acad Sci USA. 2004; 101(25):9381-9386; Laakkonen et al., Nat Med. 2002; 8(7):751-755). Another tumor-penetrating peptide, iRGD (CRGDKGPDC; SEQ ID NO:2), binds to the $\alpha v\beta 3$ and $\alpha v\beta 5$ integrins as the primary homing receptor (Sugahara et al., Cancer Cell. 2009; 16(6):510-520). The receptors for LyP-1 and iRGD are specifically expressed in tissues activated by disease processes, such as atherosclerosis or cancer, and are not present at the surface of normal cells; p32 is particularly highly expressed in a subset of activated macrophages.

The tissue penetration is mediated by another receptor, neuropilin-1 (NRP-1) (or neuropilin-2 (NRP-2)(Roth et al., Oncogene. 2012; 31(33):3754-3763). LyP-1 (and iRGD) contains an NRP-binding motif, (R/K)XX(R/K), but this sequence is not active in the intact peptide (because it is not present at a free C-terminal end of the peptide). After the peptide has bound to the primary receptor, a cell surface protease cleaves it so that the KRTR sequence in LyP-1 becomes C-terminal and acquires the ability to bind to NRP-1 (Roth et al., Oncogene. 2012; 31(33):3754-3763). This phenomenon is referred to as the C-end Rule or CendR (Teesalu et al., Proc Natl Acad Sci USA. 2009; 106(38): 16157-16162). The binding of the truncated peptide to NRP-1 activates an endocytic bulk transport pathway, which can transport payloads coupled to the peptide, as well as co-administered compounds ("bystander" effect), through the vascular wall and deep into the target tissue (Hamzah et al., Proc Natl Acad Sci USA. 2011; 108(17):7154-7159; Sugahara et al., Science 2010; 328(5981):1031-1035; FIG. 9). LyP-1 specifically homes to aortic plaques in ApoE null mice kept on high-fat diet, and can take coupled payload into the plaques but not to other tissues, such as normal portions of the vasculature (Hamzah et al., Proc Natl Acad Sci USA. 2011; 108(17):7154-7159). The LyP-1 peptide does not home to any normal tissues in tumor-bearing or atherosclerotic mice, but is transiently detected in the kidney, which is the excretion route for peptides (and other small molecules) (Hamzah et al., Proc Natl Acad Sci USA. 2011; 108(17): 7154-7159; Laakkonen et al., Proc Natl Acad Sci USA. 2004; 101(25):9381-9386; Roth et al., Oncogene. 2012; 31(33):3754-3763).

Materials

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "analog" refers to a chemical compound with a structure similar to that of another (reference compound) but differing from it in respect to a particular component, functional group, atom, etc. As used herein, the term "derivative" refers to compounds which are formed from a parent compound by chemical reaction(s). These differences in suitable analogues and derivatives include, but are not limited to, replacement of one or more functional groups on the ring with one or more different functional groups or reacting one or more functional groups on the ring to introduce one or more substituents.

Numerical ranges disclosed in the present application of any type, disclose individually each possible number that such a range could reasonably encompass, as well as any sub-ranges and combinations of sub-ranges encompassed therein. A carbon range (i.e., $C_1$-$C_{10}$), is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed therein, such as $C_2$-$C_9$, $C_3$-$C_8$, $C_1$-$C_5$, etc.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

"Alkylaryl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

"Aryl", as used herein, refers to 5-, 6- and 7-membered aromatic, heterocyclic, fused aromatic, fused heterocyclic, biaromatic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described herein, for example, halogen, azide, alkyl, aralkyl, alkenyl, alkynyl, cycloalkyl, hydroxyl, alkoxyl, amino, nitro, nitrile, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "Ar" also includes polycyclic ring systems having two or more cyclic rings in which two or more carbons are common to two adjoining rings (the rings are "fused rings") where at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) where Y is absent or is H, O, ($C_{1-4}$)alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$)alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroatom" refers to any atom other than hydrogen or carbon.

The term "alkoxy" as used herein is an alkyl group bound through a single, terminal ether linkage; that is, an "alkoxy" group may be defined as —OR where R is alkyl as defined above. A "lower alkoxy" group is an alkoxy group containing from one to six carbon atoms.

The term "alkenyl group" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

The term "carboxylic acid" as used herein is represented by the formula —C(O)OH.

The term "aldehyde" as used herein is represented by the formula —C(O)H.

The term "keto group" as used herein is represented by the formula —C(O)R, where R is an alkyl, alkenyl, alkynyl, aryl, aralkyl, cycloalkyl, halogenated alkyl, or heterocycloalkyl group described above.

The term "carbonyl group" as used herein is represented by the formula C=O.

The term "ether" as used herein is represented by the formula AOA$^1$, where A and A$^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The term "sulfo-oxo group" as used herein is represented by the formulas —S(O)$_2$R, —OS(O)$_2$R, or, —OS(O)$_2$OR, where R can be hydrogen, an alkyl, alkenyl, alkynyl, aryl, aralkyl, cycloalkyl, halogenated alkyl, or heterocycloalkyl group described above.

As used herein, "alkylamine" refers to a linear or branched carbon chain where at least one of the carbon-carbon bonds is interrupted by a nitrogen atom of the formula NR, where R is defined below.

"Halogen", as used herein, refers to fluorine, chlorine, bromine, or iodine.

"Substituted", as used herein, means that the functional group contains one or more substituents attached thereon including, but not limited to, hydrogen, halogen, cyano, alkoxyl, alkyl, alkenyl, cycloalkyl, cycloalkenyl, aryl, heterocycloalkyl, heteroaryl, amine, hydroxyl, oxo, formyl, acyl, carboxylic acid (—COOH), —C(O)R', —C(O)OR', carboxylate (—COO—), primary amide (e.g., —CONH$_2$), secondary amide (e.g., —CONHR'), —C(O)NR'R", —NR'R", —NR'S(O)$_2$R", —NR'C(O)R", —S(O)$_2$R", —SR', and —S(O)$_2$NR'R", sulfinyl group (e.g., —SOR'), and sulfonyl group (e.g., —SOOR'); where R' and R" may each independently be hydrogen, alkyl, alkenyl, alkynyl, cycloalkyl, aryl, heterocycloalkyl and heteroaryl; where each of R' and R" is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl, or combinations thereof. In some instances, "substituted" also refers to one or more substitutions of one or more of the carbon atoms in a carbon chain (i.e., alkyl, alkenyl, cycloalkyl, cycloalkenyl, and aryl groups) which can be substituted by a heteroatom, such as, but not limited to, a nitrogen or oxygen.

As used herein, the term "leaving group," refers to a chemical fragment which can be displaced by a nucleophile. Exemplary leaving groups include halides such as chlorine, bromine, and iodine; sulfonyloxy ethers like mesylate, tosylate, and triflate; carboxylates such as trifluoromethyl acetate; and ionized heteroatoms such as $-O^+R_2$, $-S^+R_2$, and $-N^+R_3$.

As used herein, the term "protecting group," refers to a chemical fragment which can be used to deactivate a reactive functional group. The protecting group forms a covalent bond with the reactive functional group. The protecting group is removed under specific condition to regenerate the reactive functional group. Exemplary oxygen protecting groups include silyl ethers such as trimethylsilyl, tertbutyldimethylsilyl, triisopropylsilyl, and tertbutyldiphenylsilyl; esters such as acetate and benzoate; and ethers such as benzyl, methoxybenzyl, tetrahydropyranyl, triphenylmethyl, and methoxymethyl. Exemplary nitrogen protecting groups include carbamates such as tert-butoxycarbonyl, benzyloxycarbonyl, and 9-fluorenylmethyloxycarbonyl; amides such as acetamide, benzamide, trifluoroacetamide, and trichloroacetamide; phthalimides; amines such as benzyl and methoxybenzyl; and sulfonamides such as 4-methylphenylsulfonamide and nitrophenylsulfonamides.

"Pharmaceutically acceptable salt," as used herein, refer to derivatives of the compounds described herein where the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

"Purification," as used herein refers to the isolation, either completely or partially, of one or more selected reaction products. Complete isolation methods can include distillation and chromatographic purification, whereas examples of partial isolation include solvent washing and solvent exchange. Purification methods are known to those of skill in the art.

The disclosed compounds and substituent groups can, independently, possess two or more of the groups listed above. For example, if the compound is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

As used herein, the term "non-natural amino acid" refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

As used herein, the term "peptide" refers to a class of compounds composed of amino acids chemically bound together and is used broadly to mean peptides, proteins, fragments of proteins and the like. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

A. Compositions

Disclosed are compositions comprising a plaque-homing element, a CendR-activating element, and a plaque-inhibiting element. The plaque-homing element can be the same as, overlap with, be coupled to, or be conjugated to the CendR-activating element. The plaque-inhibiting element can be the same as, overlap with, be coupled to, be conjugated to, or be not covalently coupled or directly non-covalently associated with the plaque-homing element, the CendR-activating element, or both.

For example, some plaque-homing elements and some CendR-activating elements are amino acid sequences. This can allow the amino acid sequence consisting of the plaque-homing element to overlap the amino acid sequence that consists of the CendR-activating element. Alternatively the plaque-homing element can be a separate entity that does not overlap with the CendR-activating element. Thus, the amino acid sequence consisting of the plaque-homing element and the amino acid sequence that consists of the CendR-activating element can be in the same peptide. Finally, the plaque-homing element and the CendR-activating can be separate molecules even if both are embodied in amino acid sequences. These same options apply if the plaque-inhibiting element is an amino acid sequence and one or both of the plaque-homing element and CendR-activating element are amino acid sequences.

Plaque-homing elements, CendR-activating elements, and plaque-inhibiting elements, whether peptides or small molecule compounds, can also be coupled or noncovalently associated with each other, or not. Generally, the bystander effect of CendR activation allows components to be internalized into cells to be separate, uncoupled and unassociated with the CendR-activating element. Two or each of the plaque-homing element, CendR-activating element, and plaque-inhibiting element can be combined in or with a nanoparticle, such as a micelle or polymeric capsule. In the nanoparticle, the different elements can be the same as, overlap with, be coupled to, or be conjugated to the one or both of the other elements, or not. Combination of the elements in a nanoparticle makes it convenient to use different amounts or proportions of the different elements in the nanoparticle. For example, including multiple plaque-homing elements, CendR-activating elements, or both on the surface can increase the efficiency of homing, CendR activation, or both, with the result that a smaller amount or proportion of plaque-inhibiting element can be used. Generally, both the plaque-homing element and the CendR-activating element should be on the surface of the nanoparticle. Plaque-homing elements, CendR-activating elements, and plaque-inhibiting elements, whether peptides or small molecule compounds, can also be tethered together via linkers.

In some forms of the composition, one or more of the plaque-homing element, CendR-activating element, and plaque-inhibiting element can be a peptide. In some forms, one or more of the one or more plaque-homing element, CendR-activating element, and plaque-inhibiting element that is a peptide can conjugate to albumin in blood. In some forms, one or more of the one or more plaque-homing element, CendR-activating element, and plaque-inhibiting element that is a peptide can be conjugated to a lipid. In some forms, one or more of the plaque-homing element, CendR-activating element, and plaque-inhibiting element can be coupled to a lipid. In some forms, the composition is comprised in a micelle. For example, one or more of the components can be couple to a lipid and the component/lipid can then be formed into a micelle. Other components can be enclosed in the micelle or coupled to the first component, the same lipid, or to a different lipid.

In some forms, one or more of the one or more plaque-homing element, CendR-activating element, and plaque-inhibiting element that is a peptide can be conjugated to nanoparticle. In some forms, one or more of the plaque-homing element, CendR-activating element, and plaque-inhibiting element can be coupled to a nanoparticle.

In some forms of the composition, one or more of the plaque-homing element, CendR-activating element, and plaque-inhibiting element can be an extended blood half-life peptide. An extended blood half-life peptide is one that includes a feature that increases the half-life of the peptide in blood over the half-life in blood of the same peptide without that feature. In some forms, the extended blood half-life peptide is a peptide that can conjugate to albumin in blood. In some forms, the extended blood half-life peptide is a peptide conjugated to a lipid. In some forms, the extended blood half-life peptide is a stabilized peptide. A stabilized peptide is a peptide that is modified to make it less susceptible to proteolytic cleavage, such as by including reduced peptide bonds or N-methylated amino acids.

In some forms of the composition, the plaque-homing element, the CendR-activating element, and plaque-inhibiting elements are collectively comprised in an extended blood half-life LyP-1 peptide. In some forms, the extended blood half-life LyP-1 can comprise CCGNKRTRGC (SEQ ID NO: 19), CGNKRTRGC (SEQ ID NO: 1) tethered to a cysteine, CGNKRTRGC (SEQ ID NO: 1) conjugated to a lipid. In some forms, the extended blood half-life LyP-1 comprises a lipid coupled to CGNKRTRGC (SEQ ID NO:1).

The compositions can include other components as may be desired, such as labels and other therapeutic agents.

1. Plaque-Homing Elements

A plaque-homing element is a compound that can binds to and accumulate at atherosclerotic plaques. Generally, plaque-homing elements can specifically bind to a molecule present in plaques or accessible on the surface of one or more types of cells present in plaques. Homing generally involves selective or specific accumulation at a target site, tissue, cells, etc. (plaques in the case of plaque-homing elements) at a greater level than, or to the substantial exclusion of, other sites, tissues, cells, etc. Certain proteins more prevalent in plaques and so make preferred targets for plaque-homing elements. The preferred target for the disclosed plaque-homing elements is p32.

i. Peptides

Useful plaque-homing elements include peptides. Examples of plaque-homing peptides include CGNKRTRGC (SEQ ID NO: 1), CGQKRTRGC (SEQ ID NO:2), $CX_aRGX_bRSX_cC$ (SEQ ID NO:3), CKRGARSTC (SEQ ID NO:4), CKRGSRSTC (SEQ ID NO:5), CKRGNRSTC (SEQ ID NO:6), CREKA (SEQ ID NO:20), CRLTLTVRKC (SEQ ID NO:21), and DPRSFL (SEQ ID NO:22). Generally, plaque-homing peptides are able to bind a molecule accessible on the surface of plaques or cells in plaques. $X_a$, $X_b$, and $X_c$ independently can be any amino acid. $X_a$ is preferably K, V, T, R, A, or Q, more preferably is K or T, and most preferably K. $X_b$ is preferably A, S, G, N, T, or K, more preferably A, S, or N, and most preferably A. Xc is preferably T, S, K, A, V, R, L, or absent, more preferably T, S, or K, and most preferably T.

ii. Compounds

Useful plaque-homing elements include compounds. For example, disclosed are small molecule compounds that specifically bind p32. In some forms, the plaque-homing element can be a compound having the structure of Formula I:

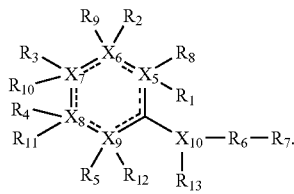

Formula I $X_5$, $X_6$, $X_7$, $X_8$, and $X_9$ can independently be C, N, S, or O. In some forms, at least one of $X_5$, $X_6$, $X_7$, $X_8$, and $X_9$ is C or N. In some forms, at least two of $X_5$, $X_6$, $X_7$, $X_8$, and $X_9$ are C or N. In some forms, at least three of $X_5$, $X_6$, $X_7$, $X_8$, and $X_9$ are C or N. In some forms, at least four of $X_5$, $X_6$, $X_7$, $X_8$, and $X_9$ are C or N. In some forms, all of $X_5$, $X_6$, $X_7$, $X_8$, and $X_9$ are C or N.

In some forms, at least one of $X_5$, $X_6$, $X_7$, $X_8$, and $X_9$ is N. In some forms, at least two of $X_5$, $X_6$, $X_7$, $X_8$, and $X_9$ are N. In some forms, at least three of $X_5$, $X_6$, $X_7$, $X_8$, and $X_9$ are N. In some forms, no more than one of $X_5$, $X_6$, $X_7$, $X_8$, and $X_9$ is N. In some forms, no more than two of $X_5$, $X_6$, $X_7$, $X_8$, and $X_9$ are N. In some forms, no more than three of $X_5$, $X_6$, $X_7$, $X_8$, and $X_9$ are N. In some forms, no more than four of $X_5$, $X_6$, $X_7$, $X_8$, and $X_9$ are N.

In some forms, at least one of $X_5$, $X_6$, $X_7$, $X_8$, and $X_9$ is C. In some forms, at least two of $X_5$, $X_6$, $X_7$, $X_8$, and $X_9$ are C. In some forms, at least three of $X_5$, $X_6$, $X_7$, $X_8$, and $X_9$ are C. In some forms, no more than one of $X_5$, $X_6$, $X_7$, $X_8$, and $X_9$ is C. In some forms, no more than two of $X_5$, $X_6$, $X_7$, $X_8$, and $X_9$ are C. In some forms, no more than three of $X_5$, $X_6$, $X_7$, $X_8$, and $X_9$ are C. In some forms, no more than four of $X_5$, $X_6$, $X_7$, $X_8$, and $X_9$ are C.

In some forms, at least one of $X_5$, $X_6$, $X_7$, $X_8$, and $X_9$ is O. In some forms, at least two of $X_5$, $X_6$, $X_7$, $X_8$, and $X_9$ are O. In some forms, none of $X_5$, $X_6$, $X_7$, $X_8$, and $X_9$ is O. In some forms, no more than one of $X_5$, $X_6$, $X_7$, $X_8$, and $X_9$ is O. In some forms, no more than two of $X_5$, $X_6$, $X_7$, $X_8$, and $X_9$ are O.

In some forms, at least one of $X_5$, $X_6$, $X_7$, $X_8$, and $X_9$ is S. In some forms, at least two of $X_5$, $X_6$, $X_7$, $X_8$, and $X_9$ are S. In some forms, none of $X_5$, $X_6$, $X_7$, $X_8$, and $X_9$ are S. In some forms, no more than one of $X_5$, $X_6$, $X_7$, $X_8$, and $X_9$ is S. In some forms, no more than two of $X_5$, $X_6$, $X_7$, $X_8$, and $X_9$ are S.

Valency in the ring bonds can be as required or allowed based on the ring atoms and the substituents on the ring bonds.

$R_1$, $R_2$, $R_3$, $R_4$, $R_5$ can independently be hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, or absent if valency requires. In some forms, at least one of $R_1$, $R_2$, $R_3$, $R_4$, and $R_5$ is substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl. $R_1$, $R_2$, $R_3$, $R_4$, and $R_5$ can be absent if valency of the ring atom requires.

In some forms, $R_1$, $R_2$, $R_3$, $R_4$, and $R_5$ can independently be hydrogen, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_1$, $R_2$, $R_3$, $R_4$, and $R_5$ can independently be hydrogen, $C_1$-$C_3$ alkyl, $C_1$-$C_3$ alkylene, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkoxy, $C_3$ alkylamino, $C_3$ alkylthio, $C_2$ alkyl, $C_2$ alkylene, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_1$, $R_2$, $R_3$, $R_4$, and $R_5$ can independently be hydrogen, $C_1$-$C_3$ alkyl, $C_1$-$C_3$ alkylene, $C_2$-$C_3$ alkenyl, $C_2$-$C_3$ alkynyl, $C_1$-$C_2$ alkyl, $C_1$-$C_2$ alkylene, $C_3$ alkyl, $C_3$ alkylene, $C_3$ alkenyl, $C_3$ alkynyl, $C_2$ alkyl, $C_2$ alkylene, $C_2$ alkenyl, $C_2$ alkynyl, $C_1$ alkyl, or $C_1$ alkylene. In some forms, $R_1$, $R_2$, $R_3$, $R_4$, and $R_5$ can independently be hydrogen, $C_1$-$C_3$ alkyl, $C_1$-$C_3$ alkylene, $C_1$-$C_2$ alkyl, $C_1$-$C_2$ alkylene, $C_3$ alkyl, $C_3$ alkylene, $C_2$ alkyl, $C_2$ alkylene, $C_1$ alkyl, or $C_1$ alkylene.

$R_8$, $R_9$, $R_{10}$, $R_{11}$, $R_{12}$, and $R_{13}$ can independently be absent, hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

In some forms, $R_8$, $R_9$, $R_{10}$, $R_{11}$, $R_{12}$, and $R_{13}$ can independently be absent, hydrogen, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_8$, $R_9$, $R_{10}$, $R_{11}$, $R_{12}$, and $R_{13}$ can independently be absent, hydrogen, $C_1$-$C_3$ alkyl, $C_1$-$C_3$ alkylene, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkoxy, $C_3$ alkylamino, $C_3$ alkylthio, $C_2$ alkyl, $C_2$ alkylene, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_8$, $R_9$, $R_{10}$, $R_{11}$, $R_{12}$, and $R_{13}$ can independently be absent, hydrogen, $C_1$-$C_3$ alkyl, $C_1$-$C_3$ alkylene, $C_2$-$C_3$ alkenyl, $C_2$-$C_3$ alkynyl, $C_1$-$C_2$ alkyl, $C_1$-$C_2$ alkylene, $C_3$ alkyl, $C_3$ alkylene, $C_3$ alkenyl, $C_3$ alkynyl, $C_2$ alkyl, $C_2$ alkylene, $C_2$ alkenyl, $C_2$ alkynyl, $C_1$ alkyl, or $C_1$ alkylene. In some forms, $R_8$, $R_9$, $R_{10}$, $R_{11}$, $R_{12}$, and $R_{13}$ can independently be absent, hydrogen, $C_1$-$C_3$ alkyl, $C_1$-$C_3$ alkylene, $C_1$-$C_2$ alkyl, $C_1$-$C_2$ alkylene, $C_3$ alkyl, $C_3$ alkylene, $C_2$ alkyl, $C_2$ alkylene, $C_1$ alkyl, or $C_1$ alkylene.

In some forms, $X_9$, $R_5$, and $R_{12}$ together can be absent, thus forming a 5-membered ring.

$X_{10}$ can be N, O, or S.

$R_6$ can be —$(CH_2)_n$— or —$(CH_2)_n$—$CHR_{14}$—$(CH_2)_m$—, or —$(CH_2)_n$—O—$(CH_2)_m$—, where n and m are independently 1, 2, 3, 4, 5, 6, 7, 8, 9, 10, and where $R_{14}$ is halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

In some forms n is less than 8. In some forms n is less than 7. In some forms n is less than 6. In some forms n is less than 5. In some forms n is less than 4. In some forms n is less than 3. In some forms n is less than 2. In some forms, n is at least 1. In some forms, n is at least 2. In some forms, n is at least 3. In some forms, n is at least 4. In some forms, n is at least 5. In some forms, n is at least 6. In some forms, n is at least 7.

In some forms m is less than 8. In some forms m is less than 7. In some forms m is less than 6. In some forms m is less than 5. In some forms m is less than 4. In some forms m is less than 3. In some forms m is less than 2. In some forms, m is at least 1. In some forms, m is at least 2. In some forms, m is at least 3. In some forms, m is at least 4. In some forms, m is at least 5. In some forms, m is at least 6. In some forms, m is at least 7.

In some forms n+m is less than 10. In some forms n+m is less than 9. In some forms n+m is less than 8. In some forms n+m is less than 7. In some forms n+m is less than 6. In some forms n+m is less than 5. In some forms n+m is less than 4. In some forms n+m is less than 3. In some forms, n+m is at least 2. In some forms, n+m is at least 3. In some forms, n+m is at least 4. In some forms, n+m is at least 5. In some forms, n+m is at least 6. In some forms, n+m is at least 7. In some forms, n+m is at least 8. In some forms, n+m is at least 9.

$R_7$ can be —$NR_{15}R_{16}$, where $R_{15}$ is hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl, and where $R_{16}$ is hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, or a group having the structure of Formula II:

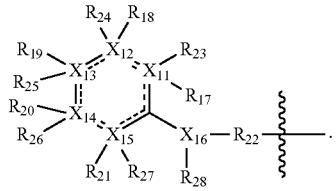

Formula II $X_{11}$, $X_{12}$, $X_{13}$, $X_{14}$, and $X_{15}$ can independently be C, N, S, or O. In some forms, at least one of $X_{11}$, $X_{12}$, $X_{13}$, $X_{14}$, and $X_{15}$ is C or N. In some forms, at least two of $X_{11}$, $X_{12}$, $X_{13}$, $X_{14}$, and $X_{15}$ are C or N. In some forms, at least three of $X_{11}$, $X_{12}$, $X_{13}$, $X_{14}$, and $X_{15}$ are C or N. In some forms, at least four of $X_{11}$, $X_{12}$, $X_{13}$, $X_{14}$, and $X_{15}$ are C or N. In some forms, all of $X_{11}$, $X_{12}$, $X_{13}$, $X_{14}$, and $X_{15}$ are C or N.

In some forms, at least one of $X_{11}$, $X_{12}$, $X_{13}$, $X_{14}$, and $X_{15}$ is N. In some forms, at least two of $X_{11}$, $X_{12}$, $X_{13}$, $X_{14}$, and $X_{15}$ are N. In some forms, at least three of $X_{11}$, $X_{12}$, $X_{13}$, $X_{14}$, and $X_{15}$ are N. In some forms, no more than one of $X_{11}$, $X_{12}$, $X_{13}$, $X_{14}$, and $X_{15}$ is N. In some forms, no more than two of $X_{11}$, $X_{12}$, $X_{13}$, $X_{14}$, and $X_{15}$ are N. In some forms, no more than three of $X_{11}$, $X_{12}$, $X_{13}$, $X_{14}$, and $X_{15}$ are N. In some forms, no more than four of $X_{11}$, $X_{12}$, $X_{13}$, $X_{14}$, and $X_{15}$ are N.

In some forms, at least one of $X_{11}$, $X_{12}$, $X_{13}$, $X_{14}$, and $X_{15}$ is C. In some forms, at least two of $X_{11}$, $X_{12}$, $X_{13}$, $X_{14}$, and $X_{15}$ are C. In some forms, at least three of $X_{11}$, $X_{12}$, $X_{13}$, $X_{14}$, and $X_{15}$ are C. In some forms, no more than one of $X_{11}$, $X_{12}$, $X_{13}$, $X_{14}$, and $X_{15}$ is C. In some forms, no more than two of $X_{11}$, $X_{12}$, $X_{13}$, $X_{14}$, and $X_{15}$ are C. In some forms, no more than three of $X_{11}$, $X_{12}$, $X_{13}$, $X_{14}$, and $X_{15}$ are C. In some forms, no more than four of $X_{11}$, $X_{12}$, $X_{13}$, $X_{14}$, and $X_{15}$ are C.

In some forms, at least one of $X_{11}$, $X_{12}$, $X_{13}$, $X_{14}$, and $X_{15}$ is O. In some forms, at least two of $X_{11}$, $X_{12}$, $X_{13}$, $X_{14}$, and $X_{15}$ are O. In some forms, none of $X_{11}$, $X_{12}$, $X_{13}$, $X_{14}$, and $X_{15}$ is O. In some forms, no more than one of $X_{11}$, $X_{12}$, $X_{13}$, $X_{14}$, and $X_{15}$ is O. In some forms, no more than two of $X_{11}$, $X_{12}$, $X_{13}$, $X_{14}$, and $X_{15}$ are O.

In some forms, at least one of $X_{11}$, $X_{12}$, $X_{13}$, $X_{14}$, and $X_{15}$ is S. In some forms, at least two of $X_{11}$, $X_{12}$, $X_{13}$, $X_{14}$, and $X_{15}$ are S. In some forms, none of $X_{11}$, $X_{12}$, $X_{13}$, $X_{14}$, and $X_{15}$ are S. In some forms, no more than one of $X_{11}$, $X_{12}$, $X_{13}$, $X_{14}$, and $X_{15}$ is S. In some forms, no more than two of $X_{11}$, $X_{12}$, $X_{13}$, $X_{14}$, and $X_{15}$ are S.

Valency in the ring bonds can be as required or allowed based on the ring atoms and the substituents on the ring bonds.

$R_{17}$, $R_{18}$, $R_{19}$, $R_{20}$, and $R_{21}$ can independently be hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, or absent if valency requires. In some forms, at least one of $R_{17}$, $R_{18}$, $R_{19}$, $R_{20}$, and $R_{21}$ can be substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl. $R_{17}$, $R_{18}$, $R_{19}$, $R_{20}$, and $R_{21}$ can be absent if valency of the ring atom requires.

In some forms, $R_{17}$, $R_{18}$, $R_{19}$, $R_{20}$, and $R_{21}$, can independently be hydrogen, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_{17}$, $R_{18}$, $R_{19}$, $R_{20}$, and $R_{21}$ can independently be hydrogen, $C_1$-$C_3$ alkyl, $C_1$-$C_3$ alkylene, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkoxy, $C_3$ alkylamino, $C_3$ alkylthio, $C_2$ alkyl, $C_2$ alkylene, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_{17}$, $R_{18}$, $R_{19}$, $R_{20}$, and $R_{21}$ can independently be hydrogen, $C_1$-$C_3$ alkyl, $C_1$-$C_3$ alkylene, $C_2$-$C_3$ alkenyl, $C_2$-$C_3$ alkynyl, $C_1$-$C_2$ alkyl, $C_1$-$C_2$ alkylene, $C_3$ alkyl, $C_3$ alkylene, $C_3$ alkenyl, $C_3$ alkynyl, $C_2$ alkyl, $C_2$ alkylene, $C_2$ alkenyl, $C_2$ alkynyl, $C_1$ alkyl, or $C_1$ alkylene. In some forms, $R_{17}$, $R_{18}$, $R_{19}$, $R_{20}$, and $R_{21}$ can independently be hydrogen, $C_1$-$C_3$ alkyl, $C_1$-$C_3$ alkylene, $C_1$-$C_2$ alkyl, $C_1$-$C_2$ alkylene, $C_3$ alkyl, $C_3$ alkylene, $C_2$ alkyl, $C_2$ alkylene, $C_1$ alkyl, or $C_1$ alkylene.

$R_{23}$, $R_{24}$, $R_{25}$, $R_{26}$, $R_{27}$, and $R_{28}$ can independently be absent, hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

In some forms, $R_{23}$, $R_{24}$, $R_{25}$, $R_{26}$, $R_{27}$, and $R_{28}$ can independently be absent, hydrogen, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_{23}$, $R_{24}$, $R_{25}$, $R_{26}$, $R_{27}$, and $R_{28}$ can independently be absent, hydrogen, $C_1$-$C_3$ alkyl, $C_1$-$C_3$ alkylene, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkoxy, $C_3$ alkylamino, $C_3$ alkylthio, $C_2$ alkyl, $C_2$ alkylene, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_{23}$, $R_{24}$, $R_{25}$, $R_{26}$, $R_{27}$, and $R_{28}$ can independently be absent, hydrogen, $C_1$-$C_3$ alkyl, $C_1$-$C_3$ alkylene, $C_2$-$C_3$ alkenyl, $C_2$-$C_3$ alkynyl, $C_1$-$C_2$ alkyl, $C_1$-$C_2$ alkylene, $C_3$ alkyl, $C_3$ alkylene, $C_3$ alkenyl, $C_3$ alkynyl, $C_2$ alkyl, $C_2$ alkylene, $C_2$ alkenyl, $C_2$ alkynyl, $C_1$ alkyl, or $C_1$ alkylene. In some forms, $R_{23}$, $R_{24}$, $R_{25}$, $R_{26}$, $R_{27}$, and $R_{28}$ can independently be absent, hydrogen, $C_1$-$C_3$ alkyl, $C_1$-$C_3$ alkylene, $C_1$-$C_2$ alkyl, $C_1$-$C_2$ alkylene, $C_3$ alkyl, $C_3$ alkylene, $C_2$ alkyl, $C_2$ alkylene, $C_1$ alkyl, or $C_1$ alkylene.

In some forms, $X_{15}$, $R_{21}$, and $R_{27}$ together can be absent, thus forming a 5-membered ring.

$X_{16}$ can be N, O, or S.

$R_{22}$ can be —$(CH_2)_j$— or —$(CH_2)_j$—$CHR_{29}$—$(CH_2)_k$—, or —$(CH_2)_j$—O—$(CH_2)_k$—, where j and k are independently 1, 2, 3, 4, 5, 6, 7, 8, 9, 10, and where $R_{29}$ is halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, or $C_1$-$C_{10}$ phosphonyl.

In some forms, the $X_5$ to $X_9$ ring can be:

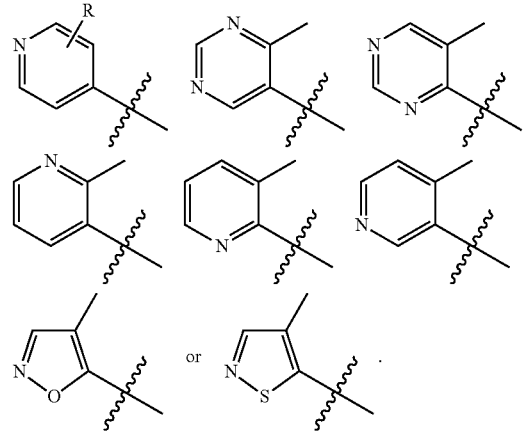

In some forms, —$X_{10}R_{13}$—$R_6$—$R_7$ can be:

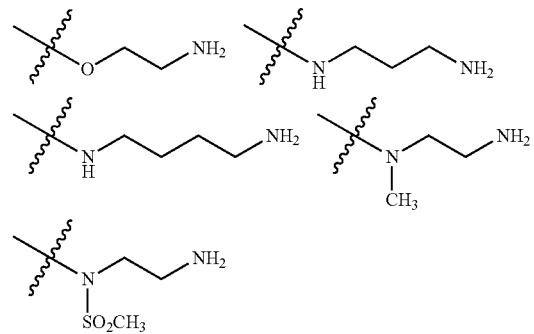

or any of these with the $NH_2$ replaced with:

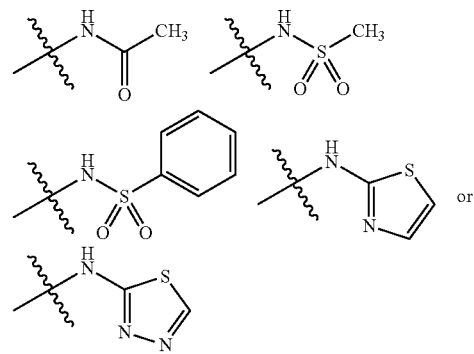

In some forms, $R_7$ can be:

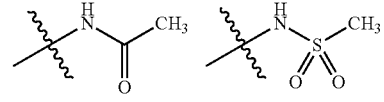

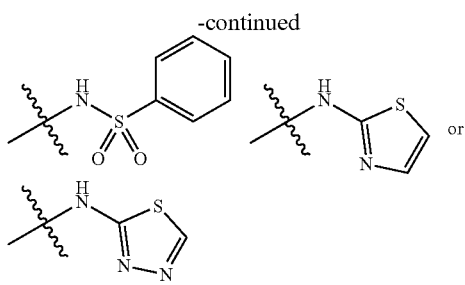

In some forms j is less than 8. In some forms j is less than 7. In some forms j is less than 6. In some forms j is less than 5. In some forms j is less than 4. In some forms j is less than 3. In some forms j is less than 2. In some forms, j is at least 1. In some forms, j is at least 2. In some forms, j is at least 3. In some forms, j is at least 4. In some forms, j is at least 5. In some forms, j is at least 6. In some forms, j is at least 7.

In some forms k is less than 8. In some forms k is less than 7. In some forms k is less than 6. In some forms k is less than 5. In some forms k is less than 4. In some forms k is less than 3. In some forms k is less than 2. In some forms, k is at least 1. In some forms, k is at least 2. In some forms, k is at least 3. In some forms, k is at least 4. In some forms, k is at least 5. In some forms, k is at least 6. In some forms, k is at least 7.

In some forms j+k is less than 10. In some forms j+k is less than 9. In some forms j+k is less than 8. In some forms j+k is less than 7. In some forms j+k is less than 6. In some forms j+k is less than 5. In some forms j+k is less than 4. In some forms j+k is less than 3. In some forms, j+k is at least 2. In some forms, j+k is at least 3. In some forms, j+k is at least 4. In some forms, j+k is at least 5. In some forms, j+k is at least 6. In some forms, j+k is at least 7. In some forms, j+k is at least 8. In some forms, j+k is at least 9.

In some forms, $R_{15}$ and $R_{16}$ can independently be hydrogen, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_{15}$ and $R_{16}$ can independently be hydrogen, $C_1$-$C_3$ alkyl, $C_1$-$C_3$ alkylene, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_3$ alkyl, $C_3$ alkylene, $C_3$ alkoxy, $C_3$ alkylamino, $C_3$ alkylthio, $C_2$ alkyl, $C_2$ alkylene, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

In some forms, $R_{15}$ and $R_{16}$ can independently be hydrogen, $C_1$-$C_3$ alkyl, $C_1$-$C_3$ alkylene, $C_2$-$C_3$ alkenyl, $C_2$-$C_3$ alkynyl, $C_1$-$C_2$ alkyl, $C_1$-$C_2$ alkylene, $C_3$ alkyl, $C_3$ alkylene, $C_3$ alkenyl, $C_3$ alkynyl, $C_2$ alkyl, $C_2$ alkylene, $C_2$ alkenyl, $C_2$ alkynyl, $C_1$ alkyl, or $C_1$ alkylene. In some forms, $R_{15}$ and $R_{16}$ can independently be hydrogen, $C_1$-$C_3$ alkyl, $C_1$-$C_3$ alkylene, $C_1$-$C_2$ alkyl, $C_1$-$C_2$ alkylene, $C_3$ alkyl, $C_3$ alkylene, $C_2$ alkyl, $C_2$ alkylene, $C_1$ alkyl, or $C_1$ alkylene.

In some forms, the plaque-homing compound can be a pharmaceutically acceptable salt or ester of the compound.

In some forms of the plaque-homing compound, one of $R_1$, $R_2$, $R_3$, $R_4$, or $R_5$ is $C_1$-$C_3$ alkyl, one of $R_1$, $R_2$, $R_3$, $R_4$, or $R_5$ is absent, and the remaining three of $R_1$, $R_2$, $R_3$, $R_4$, and $R_5$ are hydrogen. In some forms of the plaque-homing compound, one of $R_1$, $R_2$, $R_3$, $R_4$, or $R_5$ is $C_1$-$C_3$ alkyl, two of $R_1$, $R_2$, $R_3$, $R_4$, and $R_5$ are absent, and the remaining two of $R_1$, $R_2$, $R_3$, $R_4$, and $R_5$ are hydrogen. In some forms of the plaque-homing compound, two of $R_1$, $R_2$, $R_3$, $R_4$, and $R_5$ are independently $C_1$-$C_3$ alkyl, one of $R_1$, $R_2$, $R_3$, $R_4$, or $R_5$ is absent, and the remaining two of $R_1$, $R_2$, $R_3$, $R_4$, and $R_5$ are hydrogen. In some forms of the plaque-homing compound, two of $R_1$, $R_2$, $R_3$, $R_4$, and $R_5$ are independently $C_1$-$C_3$ alkyl, two of $R_1$, $R_2$, $R_3$, $R_4$, and $R_5$ are absent, and the remaining one of $R_1$, $R_2$, $R_3$, $R_4$, or $R_5$ is hydrogen. In some forms of the plaque-homing compound, one of $R_1$, $R_2$, $R_3$, $R_4$, or $R_5$ is $C_1$-$C_3$ alkyl, three of $R_1$, $R_2$, $R_3$, $R_4$, and $R_5$ are absent, and the remaining one of $R_1$, $R_2$, $R_3$, $R_4$, and $R_5$ is hydrogen. In some forms of the plaque-homing compound, two of $R_1$, $R_2$, $R_3$, $R_4$, and $R_5$ are independently $C_1$-$C_3$ alkyl, and the remaining three of $R_1$, $R_2$, $R_3$, $R_4$, and $R_5$ are absent.

In some forms of the plaque-homing compound, one of $R_8$, $R_9$, $R_{10}$, $R_{11}$, or $R_{12}$ is $C_1$-$C_3$ alkyl, one of $R_8$, $R_9$, $R_{10}$, $R_{11}$, or $R_{12}$ is absent, and the remaining three of $R_8$, $R_9$, $R_{10}$, $R_{11}$, and $R_{12}$ are hydrogen. In some forms of the plaque-homing compound, one of $R_8$, $R_9$, $R_{10}$, $R_{11}$, or $R_{12}$ is $C_1$-$C_3$ alkyl, two of $R_8$, $R_9$, $R_{10}$, $R_{11}$, and $R_{12}$ are absent, and the remaining two of $R_8$, $R_9$, $R_{10}$, $R_{11}$, and $R_{12}$ are hydrogen. In some forms of the plaque-homing compound, two of $R_8$, $R_9$, $R_{10}$, $R_{11}$, and $R_{12}$ are independently $C_1$-$C_3$ alkyl, one of $R_8$, $R_9$, $R_{10}$, $R_{11}$, or $R_{12}$ is absent, and the remaining two of $R_8$, $R_9$, $R_{10}$, $R_{11}$, and $R_{12}$ are hydrogen. In some forms of the plaque-homing compound, two of $R_8$, $R_9$, $R_{10}$, $R_{11}$, and $R_{12}$ are independently $C_1$-$C_3$ alkyl, two of $R_8$, $R_9$, $R_{10}$, $R_{11}$, and $R_{12}$ are absent, and the remaining one of $R_8$, $R_9$, $R_{10}$, $R_{11}$, or $R_{12}$ is hydrogen. In some forms of the plaque-homing compound, one of $R_8$, $R_9$, $R_{10}$, $R_{11}$, or $R_{12}$ is $C_1$-$C_3$ alkyl, three of $R_8$, $R_9$, $R_{10}$, $R_{11}$, and $R_{12}$ are absent, and the remaining one of $R_8$, $R_9$, $R_{10}$, $R_{11}$, and $R_{12}$ is hydrogen. In some forms of the plaque-homing compound, two of $R_8$, $R_9$, $R_{10}$, $R_{11}$, and $R_{12}$ are independently $C_1$-$C_3$ alkyl, and the remaining three of $R_8$, $R_9$, $R_{10}$, $R_{11}$, and $R_{12}$ are absent.

In some forms of the plaque-homing compound, one of $R_{17}$, $R_{18}$, $R_{19}$, $R_{20}$, or $R_{21}$ is $C_1$-$C_3$ alkyl, one of $R_{17}$, $R_{18}$, $R_{19}$, $R_{20}$, or $R_{21}$ is absent, and the remaining three of $R_{17}$, $R_{18}$, $R_{19}$, $R_{20}$, and $R_{21}$ are hydrogen. In some forms of the plaque-homing compound, one of $R_{17}$, $R_{18}$, $R_{19}$, $R_{20}$, or $R_{21}$ is $C_1$-$C_3$ alkyl, two of $R_{17}$, $R_{18}$, $R_{19}$, $R_{20}$, and $R_{21}$ are absent, and the remaining two of $R_{17}$, $R_{18}$, $R_{19}$, $R_{20}$, and $R_{21}$ are hydrogen. In some forms of the plaque-homing compound, two of $R_{17}$, $R_{18}$, $R_{19}$, $R_{20}$, and $R_{21}$ are independently $C_1$-$C_3$ alkyl, one of $R_{17}$, $R_{18}$, $R_{19}$, $R_{20}$, or $R_{21}$ is absent, and the remaining two of $R_{17}$, $R_{18}$, $R_{19}$, $R_{20}$, and $R_{21}$ are hydrogen. In some forms of the plaque-homing compound, two of $R_{17}$, $R_{18}$, $R_{19}$, $R_{20}$, and $R_{21}$ are independently $C_1$-$C_3$ alkyl, two of $R_{17}$, $R_{18}$, $R_{19}$, $R_{20}$, and $R_{21}$ are absent, and the remaining one of $R_{17}$, $R_{18}$, $R_{19}$, $R_{20}$, or $R_{21}$ is hydrogen. In some forms of the plaque-homing compound, one of $R_{17}$, $R_{18}$, $R_{19}$, $R_{20}$, or $R_{21}$ is $C_1$-$C_3$ alkyl, three of $R_{17}$, $R_{18}$, $R_{19}$, $R_{20}$, and $R_{21}$ are absent, and the remaining one of $R_{17}$, $R_{18}$, $R_{19}$, $R_{20}$, and $R_{21}$ is hydrogen. In some forms of the plaque-homing compound, two of $R_{17}$, $R_{18}$, $R_{19}$, $R_{20}$, and $R_{21}$ are independently $C_1$-$C_3$ alkyl, and the remaining three of $R_{17}$, $R_{18}$, $R_{19}$, $R_{20}$, and $R_{21}$ are absent.

In some forms of the plaque-homing compound, one of $R_{23}$, $R_{24}$, $R_{25}$, $R_{26}$, or $R_{27}$ is $C_1$-$C_3$ alkyl, one of $R_{23}$, $R_{24}$, $R_{25}$, $R_{26}$, or $R_{27}$ is absent, and the remaining three of $R_{23}$, $R_{24}$, $R_{25}$, $R_{26}$, and $R_{27}$ are hydrogen. In some forms of the plaque-homing compound, one of $R_{23}$, $R_{24}$, $R_{25}$, $R_{26}$, or $R_{27}$ is $C_1$-$C_3$ alkyl, two of $R_{23}$, $R_{24}$, $R_{25}$, $R_{26}$, and $R_{27}$ are absent, and the remaining two of $R_{23}$, $R_{24}$, $R_{25}$, $R_{26}$, and $R_{27}$ are hydrogen. In some forms of the plaque-homing compound, two of $R_{23}$, $R_{24}$, $R_{25}$, $R_{26}$, and $R_{27}$ are independently $C_1$-$C_3$ alkyl, one of $R_{23}$, $R_{24}$, $R_{25}$, $R_{26}$, or $R_{27}$ is absent, and the remaining two of $R_{23}$, $R_{24}$, $R_{25}$, $R_{26}$, and $R_{27}$ are hydrogen. In some forms of the plaque-homing compound, two of $R_{23}$, $R_{24}$, $R_{25}$, $R_{26}$, and $R_{27}$ are independently $C_1$-$C_3$ alkyl, two of $R_{23}$, $R_{24}$, $R_{25}$, $R_{26}$, and $R_{27}$ are absent, and the remaining one of $R_{23}$, $R_{24}$, $R_{25}$, $R_{26}$, or $R_{27}$ is hydrogen. In some forms of the plaque-homing compound, one of $R_{23}$, $R_{24}$, $R_{25}$, $R_{26}$, or $R_{27}$ is $C_1$-$C_3$ alkyl, three of $R_{23}$, $R_{24}$, $R_{25}$, $R_{26}$, and $R_{27}$ are absent, and the remaining one of $R_{23}$, $R_{24}$, $R_{25}$, $R_{26}$, and $R_{27}$ is hydrogen. In some forms of the plaque-homing compound, two of $R_{23}$, $R_{24}$, $R_{25}$, $R_{26}$, and $R_{27}$ are independently $C_1$-$C_3$ alkyl, and the remaining three of $R_{23}$, $R_{24}$, $R_{25}$, $R_{26}$, and $R_{27}$ are absent.

In some forms of the plaque-homing compound, one pair of $R_1$ and $R_8$, $R_2$ and $R_9$, $R_3$ and $R_{10}$, $R_4$ and $R_{11}$, or $R_5$ and $R_{12}$ are independently $C_1$-$C_3$ alkyl, the remaining four of $R_1$, $R_2$, $R_3$, $R_4$, and $R_5$ are hydrogen, and the remaining four of $R_8$, $R_9$, $R_{10}$, $R_{11}$, and $R_{12}$ are absent. In some forms of the plaque-homing compound, two pairs of $R_1$ and $R_8$, $R_2$ and $R_9$, $R_3$ and $R_{10}$, $R_4$ and $R_{11}$, and $R_5$ and $R_{12}$ are independently $C_1$-$C_3$ alkyl, the remaining three of $R_1$, $R_2$, $R_3$, $R_4$, and $R_5$ are hydrogen, and the remaining three of $R_8$, $R_9$, $R_{10}$, $R_{11}$, and $R_{12}$ are absent. In some forms of the plaque-homing compound, three pairs of $R_1$ and $R_8$, $R_2$ and $R_9$, $R_3$ and $R_{10}$, $R_4$ and $R_{11}$, and $R_5$ and $R_{12}$ are independently $C_1$-$C_3$ alkyl, the remaining two of $R_1$, $R_2$, $R_3$, $R_4$, and $R_5$ are hydrogen, and the remaining two of $R_8$, $R_9$, $R_{10}$, $R_{11}$, and $R_{12}$ are absent.

In some forms of the plaque-homing compound, one pair of $R_{17}$ and $R_{23}$, $R_{18}$ and $R_{24}$, $R_{19}$ and $R_{25}$, $R_{20}$ and $R_{26}$, or $R_{21}$ and $R_{27}$ are independently $C_1$-$C_3$ alkyl, the remaining four of $R_{17}$, $R_{18}$, $R_{19}$, $R_{20}$, and $R_{21}$ are hydrogen, and the remaining four of $R_{23}$, $R_{24}$, $R_{25}$, $R_{26}$, and $R_{27}$ are absent. In some forms of the plaque-homing compound, two pairs of $R_{17}$ and $R_{23}$, $R_{18}$ and $R_{24}$, $R_{19}$ and $R_{25}$, $R_{20}$ and $R_{26}$, and $R_{21}$ and $R_{27}$ are independently $C_1$-$C_3$ alkyl, the remaining three of $R_{17}$, $R_{18}$, $R_{19}$, $R_{20}$, and $R_{21}$ are hydrogen, and the remaining three of $R_{23}$, $R_{24}$, $R_{25}$, $R_{26}$, and $R_{27}$ are absent. In some forms of the plaque-homing compound, three pairs of $R_{17}$ and $R_{23}$, $R_{18}$ and $R_{24}$, $R_{19}$ and $R_{25}$, $R_{20}$ and $R_{26}$, and $R_{21}$ and $R_{27}$ are independently $C_1$-$C_3$ alkyl, the remaining two of $R_{17}$, $R_{18}$, $R_{19}$, $R_{20}$, and $R_{21}$ are hydrogen, and the remaining two of $R_{23}$, $R_{24}$, $R_{25}$, $R_{26}$, and $R_{27}$ are absent.

In some forms of the plaque-homing compound, one of $X_5$, $X_6$, $X_7$, $X_8$, or $X_9$ is N, and the other four of $X_5$, $X_6$, $X_7$, $X_8$, and $X_9$ are C. In some forms of the plaque-homing compound, two of $X_5$, $X_6$, $X_7$, $X_8$, and $X_9$ that are not adjacent are N, and the other three of $X_5$, $X_6$, $X_7$, $X_8$, and $X_9$ are C. In some forms of the plaque-homing compound, three of $X_5$, $X_6$, $X_7$, $X_8$, or $X_9$ that are not adjacent are N, and the other two of $X_5$, $X_6$, $X_7$, $X_8$, and $X_9$ are C.

In some forms of the plaque-homing compound, one of $X_{11}$, $X_{12}$, $X_{13}$, $X_{14}$, or $X_{15}$ is N, and the other four of $X_{11}$, $X_{12}$, $X_{13}$, $X_{14}$, and $X_{15}$ are C. In some forms of the plaque-homing compound, two of $X_{11}$, $X_{12}$, $X_{13}$, $X_{14}$, and $X_{15}$ that are not adjacent are N, and the other three of $X_{11}$, $X_{12}$, $X_{13}$, $X_{14}$, and $X_{15}$ are C. In some forms of the plaque-homing compound, three of $X_{11}$, $X_{12}$, $X_{13}$, $X_{14}$, or $X_{15}$ that are not adjacent are N, and the other two of $X_{11}$, $X_{12}$, $X_{13}$, $X_{14}$, and $X_{15}$ are C.

In some forms of the plaque-homing compound, one of $X_5$, $X_6$, $X_7$, $X_8$, or $X_9$ is N, one of $X_5$, $X_6$, $X_7$, $X_8$, or $X_9$ is S, and the remaining three of $X_5$, $X_6$, $X_7$, $X_8$, and $X_9$ are C. In some forms of the plaque-homing compound, two of $X_5$, $X_6$, $X_7$, $X_8$, and $X_9$ are N, one of $X_5$, $X_6$, $X_7$, $X_8$, or $X_9$ is S, and the remaining two of $X_5$, $X_6$, $X_7$, $X_8$, and $X_9$ are C. In some forms of the plaque-homing compound, three of $X_5$, $X_6$, $X_7$, $X_8$, and $X_9$ are N, and one of $X_5$, $X_6$, $X_7$, $X_8$, or $X_9$ is S.

In some forms of the plaque-homing compound, one of $X_{11}$, $X_{12}$, $X_{13}$, $X_{14}$, or $X_{15}$ is N, one of $X_{11}$, $X_{12}$, $X_{13}$, $X_{14}$, or $X_{15}$ is S, and the remaining three of $X_{11}$, $X_{12}$, $X_{13}$, $X_{14}$, and $X_{15}$ are C. In some forms of the plaque-homing compound, two of $X_{11}$, $X_{12}$, $X_{13}$, $X_{14}$, and $X_{15}$ are N, one of $X_{11}$, $X_{12}$, $X_{13}$, $X_{14}$, or $X_{15}$ is S, and the remaining two of $X_{11}$, $X_{12}$, $X_{13}$, $X_{14}$, and $X_{15}$ are C. In some forms of the plaque-homing compound, three of $X_{11}$, $X_{12}$, $X_{13}$, $X_{14}$, and $X_{15}$ are N, and one of $X_{11}$, $X_{12}$, $X_{13}$, $X_{14}$, or $X_{15}$ is S.

In some forms of the plaque-homing compound, one of $R_1$, $R_2$, $R_3$, $R_4$, or $R_5$ is $C_1$-$C_3$ alkyl, one of $R_1$, $R_2$, $R_3$, $R_4$, or $R_5$ is absent, the remaining three of $R_1$, $R_2$, $R_3$, $R_4$, and $R_5$ are hydrogen, $R_{15}$, $R_{16}$, and $R_{17}$ are hydrogen, $R_8$-$R_{12}$ are absent, one of $X_5$, $X_6$, $X_7$, $X_8$, or $X_9$ is N, the other four of $X_5$, $X_6$, $X_7$, $X_8$, and $X_9$ are C, $R_6$ is —$(CH_2)_n$—, n is 2-5, $R_7$ is —$NR_{15}R_{16}$, and $X_{10}$ is N.

In some forms of the plaque-homing compound, one of $R_1$, $R_2$, $R_3$, $R_4$, or $R_5$ is $C_1$-$C_3$ alkyl, two of $R_1$, $R_2$, $R_3$, $R_4$, and $R_5$ are absent, the remaining two of $R_1$, $R_2$, $R_3$, $R_4$, and $R_5$ are hydrogen, $R_{15}$, $R_{16}$, and $R_{17}$ are hydrogen, $R_8$-$R_{12}$ are absent, two of $X_5$, $X_6$, $X_7$, $X_8$, and $X_9$ that are not adjacent are N, the other three of $X_5$, $X_6$, $X_7$, $X_8$, and $X_9$ are C, $R_6$ is —$(CH_2)_n$—, n is 2-5, $R_7$ is —$NR_{15}R_{16}$, and $X_{10}$ is N.

In some forms of the plaque-homing compound, two of $R_1$, $R_2$, $R_3$, $R_4$, and $R_5$ are independently $C_1$-$C_3$ alkyl, one of $R_1$, $R_2$, $R_3$, $R_4$, or $R_5$ is absent, the remaining two of $R_1$, $R_2$, $R_3$, $R_4$, and $R_5$ are hydrogen, $R_{15}$, $R_{16}$, and $R_{17}$ are hydrogen, $R_8$-$R_{12}$ are absent, one of $X_5$, $X_6$, $X_7$, $X_8$, or $X_9$ is N, the other four of $X_5$, $X_6$, $X_7$, $X_8$, and $X_9$ are C, $R_6$ is —$(CH_2)_n$—, n is 2-5, $R_7$ is —$NR_{15}R_{16}$, and $X_{10}$ is N.

In some forms of the plaque-homing compound, two of $R_1$, $R_2$, $R_3$, $R_4$, and $R_5$ are independently $C_1$-$C_3$ alkyl, two of $R_1$, $R_2$, $R_3$, $R_4$, and $R_5$ are absent, the remaining one of $R_1$, $R_2$, $R_3$, $R_4$, or $R_5$ is hydrogen, $R_{15}$, $R_{16}$, and $R_{17}$ are hydrogen, $R_8$-$R_{12}$ are absent, two of $X_5$, $X_6$, $X_7$, $X_8$, and $X_9$ that are not adjacent are N, the other three of $X_5$, $X_6$, $X_7$, $X_8$, and $X_9$ are C, $R_6$ is —$(CH_2)_n$—, n is 2-5, $R_7$ is —$NR_{15}R_{16}$, and $X_{10}$ is N.

In some forms of the plaque-homing compound, one of $R_1$, $R_2$, $R_3$, $R_4$, or $R_5$ is $C_1$-$C_3$ alkyl, three of $R_1$, $R_2$, $R_3$, $R_4$, and $R_5$ are absent, the remaining one of $R_1$, $R_2$, $R_3$, $R_4$, and $R_5$ is hydrogen, $R_{15}$, $R_{16}$, and $R_{17}$ are hydrogen, $R_8$-$R_{12}$ are absent, three of $X_5$, $X_6$, $X_7$, $X_8$, or $X_9$ that are not adjacent are N, the other two of $X_5$, $X_6$, $X_7$, $X_8$, and $X_9$ are C, $R_6$ is —$(CH_2)_n$—, n is 2-5, $R_7$ is —$NR_{15}R_{16}$, and $X_{10}$ is N.

In some forms of the plaque-homing compound, two of $R_1$, $R_2$, $R_3$, $R_4$, and $R_5$ are independently $C_1$-$C_3$ alkyl, the remaining three of $R_1$, $R_2$, $R_3$, $R_4$, and $R_5$ are absent, $R_{15}$, $R_{16}$, and $R_{17}$ are hydrogen, $R_8$-$R_{12}$ are absent, three of $X_5$, $X_6$, $X_7$, $X_8$, or $X_9$ that are not adjacent are N, the other two of $X_5$, $X_6$, $X_7$, $X_8$, and $X_9$ are C, $R_6$ is —$(CH_2)_n$—, n is 2-5, $R_7$ is —$NR_{15}R_{16}$, and $X_{10}$ is N.

In some forms of the plaque-homing compound, $R_7$ is a group having the structure of Formula II, $R_1$, $R_4$, $R_5$, $R_8$-$R_{12}$, $R_{17}$, $R_{20}$, $R_{21}$, and $R_{23}$-$R_{27}$ are absent, $R_3$, $R_{10}$, $R_{19}$, and $R_{25}$ are independently $C_1$-$C_3$ alkyl, $R_2$, $R_{13}$, $R_{18}$, and $R_{28}$ are hydrogen, $R_6$ is —$(CH_2)_n$—, n is 1, $X_5$, $X_{10}$, $X_{11}$, and $X_{16}$ are N, $X_6$, $X_7$, $X_{12}$, and $X_{13}$ are C, $X_8$ and $X_{14}$ are S, $X_9$ and $X_{15}$ are absent, $R_{22}$ is —$(CH_2)_j$—, and j is 1.

In some forms of the plaque-homing compound, $R_1$ is —$CH_3$, $R_2$, $R_4$, $R_5$, $R_{15}$, $R_{16}$, and $R_{17}$ are hydrogen, $R_3$ and $R_8$-$R_{12}$ are absent, $R_6$ is —$(CH_2)_n$—, n is 2, $R_7$ is —$NR_{15}R_{16}$, $R_{15}$ and $R_{16}$ are hydrogen, $X_5$, $X_6$, $X_8$, and $X_9$ are C, and $X_7$ and $X_{10}$ are N.

In some forms of the plaque-homing compound, $R_7$ is a group having the structure of Formula II, $R_1$, $R_4$, $R_5$, $R_8$-$R_{12}$, $R_{17}$, $R_{20}$, $R_{21}$, and $R_{23}$-$R_{27}$ are absent, $R_3$, $R_{10}$, $R_{19}$, and $R_{25}$ are —$CH_3$, $R_2$, $R_{13}$, $R_{18}$, and $R_{28}$ are hydrogen, $R_6$ is —$(CH_2)_n$—, n is 1, $X_5$, $X_{10}$, $X_{11}$, and $X_{16}$ are N, $X_6$, $X_7$, $X_{12}$, and $X_{13}$ are C, $X_8$ and $X_{14}$ are S, $X_9$ and $X_{15}$ are absent, $R_{22}$ is —$(CH_2)_j$—, and j is 1.

In some forms, $R_1$, $R_2$, $R_3$, $R_4$, $R_5$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{23}$, $R_{24}$, $R_{25}$, $R_{26}$, $R_{27}$, $R_{28}$, and $R_{29}$ can independently be absent, hydrogen, halogen, azide, hydroxyl, amino, thiol, oxo, phosphate, nitro, nitrile, imino, amido, phosphonate, phosphinate, silyl, ether, ketone, aldehyde, ester, heterocyclyl, —$CF_3$, —CN, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, or absent if valency requires, wherein at least one of $R_1$, $R_2$, $R_3$, $R_4$, and $R_5$ is substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, $C_1$-$C_9$ alkyl, $C_1$-$C_9$ alkylene, $C_2$-$C_9$ alkenyl, $C_2$-$C_9$ alkynyl, $C_1$-$C_9$ alkoxy, $C_1$-$C_9$ alkylamino, $C_1$-$C_9$ alkylthio, $C_1$-$C_9$ carbonyl, $C_1$-$C_9$ carboxyl, $C_1$-$C_9$ amido, $C_1$-$C_9$ sulfonyl, $C_1$-$C_9$ sulfonic acid, $C_1$-$C_9$ sulfamoyl, $C_1$-$C_9$ sulfoxide, $C_1$-$C_9$ phosphoryl, $C_1$-$C_9$ phosphonyl, $C_1$-$C_8$ alkyl, $C_1$-$C_8$ alkylene, $C_2$-$C_8$ alkenyl, $C_2$-$C_8$ alkynyl, $C_{1-8}$ alkoxy, $C_1$-$C_8$ alkylamino, $C_1$-$C_8$ alkylthio, $C_1$-$C_8$ carbonyl, $C_1$-$C_8$ carboxyl, $C_1$-$C_8$ amido, $C_1$-$C_8$ sulfonyl, $C_1$-$C_8$ sulfonic acid, $C_1$-$C_8$ sulfamoyl, $C_1$-$C_8$ sulfoxide, $C_1$-$C_8$ phosphoryl, $C_1$-$C_8$ phosphonyl, $C_1$-$C_7$ alkyl, $C_1$-$C_7$ alkylene, $C_2$-$C_7$ alkenyl, $C_2$-$C_7$ alkynyl, $C_1$-$C_7$ alkoxy, $C_1$-$C_7$ alkylamino, $C_1$-$C_7$ alkylthio, $C_1$-$C_7$ carbonyl, $C_1$-$C_7$ carboxyl, $C_1$-$C_7$ amino, $C_1$-$C_7$ amido, $C_1$-$C_7$ sulfonyl, $C_1$-$C_7$ sulfonic acid, $C_1$-$C_7$ sulfamoyl, $C_1$-$C_7$ sulfoxide, $C_1$-$C_7$ phosphoryl, $C_1$-$C_7$ phosphonyl, $C_1$-$C_6$ alkyl, $C_1$-$C_6$ alkylene, $C_2$-$C_6$ alkenyl, $C_2$-$C_6$ alkynyl, $C_1$-$C_6$ alkoxy, $C_1$-$C_6$ alkylamino, $C_1$-$C_6$ alkylthio, $C_1$-$C_6$ carbonyl, $C_1$-$C_6$ carboxyl, $C_1$-$C_6$ amido, $C_1$-$C_6$ sulfonyl, $C_1$-$C_6$ sulfonic acid, $C_1$-$C_6$ sulfamoyl, $C_1$-$C_6$ sulfoxide, $C_2$-$C_6$ phosphoryl, $C_2$-$C_6$ phosphonyl, $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_5$ carbonyl, $C_1$-$C_5$ carboxyl, $C_1$-$C_5$ amido, $C_1$-$C_5$ sulfonyl, $C_1$-$C_5$ sulfonic acid, $C_1$-$C_5$ sulfamoyl, $C_1$-$C_5$ sulfoxide, $C_1$-$C_5$ phosphoryl, $C_1$-$C_5$ phosphonyl, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_{10}$ sulfonyl, $C_0$-$C_{10}$ sulfonic acid, $C_0$-$C_{10}$ sulfamoyl, $C_0$-$C_{10}$ sulfoxide, $C_0$-$C_{10}$ phosphoryl, $C_0$-$C_{10}$ phosphonyl, $C_0$-$C_9$ sulfonyl, $C_0$-$C_9$ sulfonic acid, $C_0$-$C_9$ sulfamoyl, $C_0$-$C_9$ sulfoxide, $C_0$-$C_9$ phosphoryl, $C_0$-$C_9$ phosphonyl, $C_0$-$C_8$ sulfonyl, $C_0$-$C_8$ sulfonic acid, $C_0$-$C_8$ sulfamoyl, $C_0$-$C_8$ sulfoxide, $C_0$-$C_8$ phosphoryl, $C_0$-$C_8$ phosphonyl, $C_0$-$C_7$ sulfonyl, $C_0$-$C_7$ sulfonic acid, $C_0$-$C_7$ sulfamoyl, $C_0$-$C_7$ sulfoxide, $C_0$-$C_7$ phosphoryl, $C_0$-$C_7$ phosphonyl, $C_0$-$C_6$ sulfonyl, $C_0$-$C_6$ sulfonic acid, $C_0$-$C_6$ sulfamoyl, $C_0$-$C_6$ sulfoxide, $C_0$-$C_6$ phosphoryl, $C_0$-$C_6$ phosphonyl, $C_0$-$C_5$ sulfonyl, $C_0$-$C_5$ sulfonic acid, $C_0$-$C_5$ sulfamoyl, $C_0$-$C_5$ sulfoxide, $C_0$-$C_5$ phosphoryl, $C_0$-$C_5$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_{10}$ carbonyl, $C_{10}$ carboxyl, $C_{10}$ amido, $C_{10}$ sulfonyl, $C_{10}$ sulfonic acid, $C_{10}$ sulfamoyl, $C_{10}$ sulfoxide, $C_{10}$ phosphoryl, $C_{10}$ phosphonyl, $C_9$ alkyl, $C_9$ alkylene, $C_9$ alkenyl, $C_9$ alkynyl, $C_9$ alkoxy, $C_9$ alkylamino, $C_9$ alkylthio, $C_9$ carbonyl, $C_9$ carboxyl, $C_9$ amido, $C_9$ sulfonyl, $C_9$ sulfonic acid, $C_9$ sulfamoyl, $C_9$ sulfoxide, $C_9$ phosphoryl, $C_9$ phosphonyl, $C_8$ alkyl, $C_8$ alkylene, $C_8$ alkenyl, $C_8$ alkynyl, $C_8$ alkoxy, $C_8$ alkylamino, $C_8$ alkylthio, $C_8$ carbonyl, $C_8$ carboxyl, $C_8$ amido, $C_8$ sulfonyl, $C_8$ sulfonic acid, $C_8$ sulfamoyl, $C_8$ sulfoxide, $C_8$ phosphoryl, $C_8$ phosphonyl, $C_7$ alkyl, $C_7$ alkylene, $C_7$ alkenyl, $C_7$ alkynyl, $C_7$ alkoxy, $C_7$ alkylamino, $C_7$ alkylthio, $C_7$ carbonyl, $C_7$ carboxyl, $C_7$ amido, $C_7$ sulfonyl, $C_7$ sulfonic acid, $C_7$ sulfamoyl, $C_7$ sulfoxide, $C_7$ phosphoryl, $C_7$ phosphonyl, $C_6$ alkyl, $C_6$ alkylene, $C_6$ alkenyl, $C_6$ alkynyl, $C_6$ alkoxy, $C_6$ alkylamino, $C_6$ alkylthio, $C_6$ carbonyl, $C_6$ carboxyl, $C_6$ amido, $C_6$ sulfonyl, $C_6$ sulfonic acid, $C_6$ sulfamoyl, $C_6$ sulfoxide, $C_6$ phosphoryl, $C_6$ phosphonyl, $C_5$ alkyl, $C_5$ alkylene, $C_5$ alkenyl, $C_5$ alkynyl, $C_5$ alkoxy, $C_5$ alkylamino, $C_5$ alkylthio, $C_5$ carbonyl, $C_5$ carboxyl, $C_5$ amido, $C_5$ sulfonyl, $C_5$ sulfonic acid, $C_5$ sulfamoyl, $C_5$ sulfoxide, $C_5$ phosphoryl, $C_5$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

In some forms, $R_1$, $R_2$, $R_3$, $R_4$, $R_5$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{23}$, $R_{24}$, $R_{25}$, $R_{26}$, $R_{27}$, $R_{28}$, and $R_{29}$ can independently be absent, hydrogen, or substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_9$ alkyl, $C_1$-$C_9$ alkylene, $C_2$-$C_9$ alkenyl, $C_2$-$C_9$ alkynyl, $C_1$-$C_9$ alkoxy, $C_1$-$C_9$ alkylamino, $C_1$-$C_9$ alkylthio, $C_1$-$C_8$ alkyl, $C_1$-$C_8$ alkylene, $C_2$-$C_8$ alkenyl, $C_2$-$C_8$ alkynyl, $C_1$-$C_8$ alkoxy, $C_1$-$C_8$ alkylamino, $C_1$-$C_8$ alkylthio, $C_1$-$C_7$ alkyl, $C_1$-$C_7$ alkylene, $C_2$-$C_7$ alkenyl, $C_2$-$C_7$ alkynyl, $C_1$-$C_7$ alkoxy, $C_1$-$C_7$ alkylamino, $C_1$-$C_7$ alkylthio, $C_1$-$C_6$ alkyl, $C_1$-$C_6$ alkylene, $C_2$-$C_6$ alkenyl, $C_2$-$C_6$ alkynyl, $C_1$-$C_6$ alkoxy, $C_1$-$C_6$ alkylamino, $C_1$-$C_6$ alkylthio, $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

The term "homing molecule" as used herein, means any molecule that selectively homes in vivo to specific cells or specific tissue in preference to normal tissue. Similarly, the term "homing peptide" or "homing peptidomimetic" means a peptide that selectively homes in vivo to specific cells or specific tissue in preference to normal tissue. It is understood that a homing molecule that selectively homes in vivo to specific cells or specific tissue or can exhibit preferential homing to specific cells or specific tissue.

By "selectively homes" is meant that, in vivo, the homing molecule binds preferentially to the target as compared to non-target. For example, the homing molecule can bind preferentially to tumors, as compared to non-tumors. Selective homing to, for example, atherosclerotic plaques generally is characterized by at least a two-fold greater localization within plaques, as compared to non-plaque cells and tissues. A homing molecule can be characterized by, for example, 5-fold, 10-fold, 20-fold or more preferential localization to the target as compared to one or more non-targets. For example, a homing molecule can be characterized by, for example, 5-fold, 10-fold, 20-fold or more preferential localization to atherosclerotic plaques as compared to non-plaque cells and tissues. As another example, a homing molecule can be characterized by, for example, 5-fold, 10-fold, 20-fold or more preferential localization to atherosclerotic plaques as compared to non-plaque cells and tissues. Thus, it is understood that, in some cases, a homing molecule homes, in part, to one or more normal organs in addition to homing to the target tissue. Selective homing can also be referred to as targeting. The molecules, proteins, cells, tissues, etc. that are targeted by homing molecules can be referred to as targeted molecules, proteins, cells, tissues, etc.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces. This binding can occur in addition to that binding which occurs with the CendR-activating element.

2. CendR-Activating Elements

CendR-activating elements are compounds and compositions that activate the CendR pathway. The CendR pathway was discovered as a cell-internalizing system triggered by binding of certain peptides to a cell surface receptor. These peptides have a C-terminal element as a defining feature that signals highly efficient internalization of phage and free peptides into cells. This internalization phenomenon has been named the "C-end rule" or "CendR." The CendR pathway can be used for passage of compositions of interest from the vasculature and their spread into tissue. The C-terminal element can cause spread of compositions from the vasculature (and thus can be spread into tumor tissue from an intravenous injection, for example). CendR-activating elements can also be used to mediate passage of compositions of interest through other CendR-capable membranes, such as mucous membranes and the blood-brain barrier. As used herein, "tissue penetration" and "penetration of tissue" refer to passage into or through a tissue beyond or through the outer or a first layer of cells or through a tissue membrane. Such passage or penetration through tissue (which can also be referred to as extravasation and tissue penetration) can be a function of, for example, cell internalization and passage between cells in the tissue. Throughout this application, when the term "tissue penetration" is used, it is understood that such penetration can also extend to other barriers and CendR-capable membranes found throughout the body, such as the blood brain barrier.

In some forms, the CendR-activating element can bind to NRP-1, NRP-2, or both. In some forms, the CendR-activating element can be a peptide or a small molecule compound. Small molecule compounds that bind to NRP-1, NRP-2, or both can activate the CendR pathway. Such compounds can be used as CendR-activating elements.

Useful forms of CendR-activating elements are CendR elements. CendR elements are amino acid sequences with a C-terminal element as a defining feature that signals highly efficient internalization of phage and free peptides into cells. Unlike the known cell-penetrating peptides, the CendR internalizing element is position-dependent—it is inactive when present in positions other than the C-terminus of the peptide. Another distinguishing feature is that the CendR element is stereo-specific; that is, CendR elements composed of D-amino acids are inactive. A latent CendR peptide can be activated by cleavage by, for example, the appropriate proteolytic enzyme to expose, for example, a C-terminal arginine, lysine, or lysine-glycine. Throughout the application, when the term "CendR element" or "C-terminal element" is used, it is used to describe a C-terminal arginine, a C-terminal lysine, or a C-terminal lysine-glycine pair, where glycine is at the furthest C-terminal position. In other words, in the case where a lysine is on the C terminus end, the CendR element can remain functional with a glycine on the C terminus side of the lysine. However, it is not necessary to have glycine on the end in order for the lysine residue to be functional as a C-terminal element, so that lysine can be present without glycine and still be functional. The converse is not true, however, in that glycine cannot function as a C-terminal element without the presence of lysine adjacent to it. Arginine does not require either lysine or glycine to function as a C-terminal element, as long as it remains in the furthest C-terminal position. Such CendR elements can be referred to as type 1 CendR elements.

The term "CendR element" or "C-terminal element" can also be used to describe a C-terminal histidine and amino acid sequences having the sequence $X_1X_2X_3X_4$, where $X_1$ can be R, K or H, where $X_4$ can be R, K, H, or KG, and where $X_2$ and $X_3$ can each be, independently, any amino acid. Such CendR elements can be referred to as type 2 CendR elements. The $X_2$ and $X_3$ amino acids can be selected for specific purposes. For example, $X_2$, $X_3$, or both can be chosen to form all or a portion of a protease recognition sequence. This would be useful, for example, to specify or enable cleavage of a peptide having the CendR element as a latent or cryptic CendR element that is activated by cleavage following the $X_4$ amino acid. Examples of such amino acid choices are shown in Tables 1 and 2. The $X_1$, $X_2$ and $X_3$ amino acids can also be selected, for example, to recruit additional proteins to NRP-1 molecules at the cell surface. This can be applied, for example, to modulate the selectivity and internalization and/or tissue penetration potency of CendR elements (and the compositions, conjugates, proteins, and peptides containing CendR elements). The $X_2$ and $X_3$ amino acids can also be selected to prevent protease cleavage within the $X_1$-$X_4$ motif. Optionally, certain amino acids can also be excluded from use for $X_2$, $X_3$, or both. For example, if desired, G and D can be excluded from simultaneous use as $X_2$ and $X_3$, respectively. Some type 2 CendR elements can also be described as (R/K/H)XX(R/K/H) (SEQ ID NO:24) and (R/K/H)XXKG (SEQ ID NO:25). As used herein, amino acids enclosed in parentheses and separated by slashes are alternative amino acids for that amino acid position. Thus, for example, the sequence XX(R/K) refers to XXR and XXK as alternatives.

Examples of CendR elements include XX(R/K/H), XX(R/K), XX(R/H), XX(K/H), XXR, XXK, XXH, XXKG, RXX(R/K/H), RXX(R/K), RXX(R/H), RXX(K/H), RXXR, RXXK, RXXH, RXXKG, KXX(R/K/H), KXX(R/K), KXX(R/H), KXX(K/H), KXXR, KXXK, KXXH, KXXKG, HXX(R/K/H), HXX(R/K), HXX(R/H), HXX(K/H), HXXR, HXXK, HXXH, HXXKG, (R/K/H)XXR, (R/K)XXR, (R/H)XXR, (K/H)XXR, RXXR, KXXR, HXXR, (R/K/H)XXK, (R/K)XXK, (R/H)XXK, (K/H)XXK, RXXK, KXXK, HXXK, (R/K/H)XXH, (R/K)XXH, (R/H)XXH, (K/H)XXH, RXXH, KXXH, HXXH, (R/K/H)XXKG, (R/K)XXKG, (R/H)XXKG, (K/H)XXKG, RXXKG, KXXKG, and HXXKG.

In some forms, the CendR-activating element can be CGNKRTRGC (SEQ ID NO:1), CGQKRTRGC (SEQ ID NO:2), GNKRTR (SEQ ID NO:7), $CX_aRGX_bRSX_cC$ (SEQ ID NO:3), CKRGARSTC (SEQ ID NO:4), CKRGSRSTC (SEQ ID NO:5), CKRGNRSTC (SEQ ID NO:6), CKRGAR (SEQ ID NO:9), CKRGSR (SEQ ID NO: 10), CKRGNR (SEQ ID NO: 11), $CX_aRGX_bR$ (SEQ ID NO:13), KRGAR (SEQ ID NO:14), KRGSR (SEQ ID NO:15), KRGNR (SEQ ID NO:16), $RGX_bR$ (SEQ ID NO:12), $X_aRGX_bR$ (SEQ ID NO:17), or RPARPAR (SEQ ID NO:18).

A CendR element that can be internalized into a cell can be referred to as an internalization CendR element. A CendR element that can penetrate tissue can be referred to as a penetrating CendR element. A CendR element that can be internalized into a cell and that can penetrate tissue can be referred to as an internalization and penetrating CendR element. Unless the context clearly indicates otherwise, reference to "CendR element" refers to any of these, either individually, collectively, or in any combination.

As used herein, "CendR composition" refers to a composition that comprises a CendR element. The CendR element can be, for example, active, activatable, or blocked. For example, the CendR composition can comprise a protein or peptide comprising an amino acid sequence that comprises a CendR element where the amino acid sequence is at the C-terminal end of the protein or peptide.

As used herein, "activatable CendR element" refers to a CendR element having a molecule, moiety, nanoparticle, compound or other composition covalently coupled to the CendR element, such as to the terminal carboxyl group of the C-terminal element, where the molecule, moiety, nanoparticle, compound or other composition can block internalization and/or tissue penetration of the CendR composition, conjugate, molecule, protein, peptide, etc. and where the molecule, moiety, nanoparticle, compound or other composition can be removed (to expose the terminal carboxy group, for example). For example, the activatable CendR element can be on the C-terminal end of the peptide, and can prevent the CendR element from being internalized and/or from penetrating tissue.

The molecule, nanoparticle, moiety, compound or other composition covalently coupled to the CendR element in an activatable CendR element can be referred to as the "blocking group." For example, the blocking group can be coupled to the terminal carboxyl group of the C-terminal arginine or lysine or other C-terminal amino acid of the CendR element, to the C-terminal amino acid of the CendR element, or to an amino acid of the CendR element other than the C-terminal amino acid. The blocking group can also be coupled, or associated with a part of a CendR composition, conjugate, molecule, protein, peptide, etc. other than the CendR element so long as it can prevent the CendR element from being internalized and/or from penetrating tissue.

A CendR composition comprising an activatable CendR element can be referred to as an activatable CendR composition. A CendR molecule comprising an activatable CendR element can be referred to as an activatable CendR molecule. A CendR conjugate comprising an activatable CendR element can be referred to as an activatable CendR conjugate. A CendR protein comprising an activatable CendR element can be referred to as an activatable CendR protein. A CendR peptide comprising an activatable CendR element can be referred to as an activatable CendR peptide.

The CendR element sequence being blocked by the blocking group in an activatable CendR element can be referred to as a latent or cryptic CendR element. The latent or cryptic CendR element of an activatable CendR element can be considered an "exposable" CendR element since activation of the activatable CendR element results in exposure of the CendR element at the free C-terminal end of the peptide or protein having the CendR element. A free C-terminal end or free C terminus of a peptide is the free carboxyl group at the terminal amino acid of the peptide.

An activatable CendR element can be blocked from internalization into a cell, from tissue penetration, or both. Generally, an activatable CendR element will be blocked from both internalization into a cell and penetration of tissue. Such activatable CendR elements can be referred to as activatable internalization and penetrating CendR elements. However, some activatable CendR elements could be blocked only from tissue penetration or only from internalization into a cell. Such activatable CendR elements can be referred to as activatable internalization CendR elements (for CendR elements that are blocked only from internalization into a cell) or as activatable internalization and penetrating CendR elements (for CendR elements that are blocked only from penetration of tissue). Generally, internalization CendR elements that are activatable will be activatable internalization CendR elements. Similarly, penetrating CendR elements that are activatable generally will be activatable penetrating CendR elements. Internalization and penetrating CendR elements that are activatable will be activatable internalization and penetrating CendR elements.

Removal of the blocking group will allow the CendR element to be internalized into a cell, penetrate tissue, or both.

The cleavable bond of an activatable CendR element can be cleaved in any suitable way. For example, the cleavable bond can be cleaved enzymatically or non-enzymatically. For enzymatic cleavage, the cleaving enzyme can be supplied or can be present at a site where the CendR element is delivered, homes, travels or accumulates. For example, the enzyme can be present in proximity to a cell to which the CendR element is delivered, homes, travels, or accumulates. For non-enzymatic cleavage, the CendR element can be brought into contact with a cleaving agent, can be placed in cleaving conditions, or both. A cleaving agent is any substance that can mediate or stimulate cleavage of the cleavable bond. A non-enzymatic cleaving agent is any cleaving agent except enzymes. Cleaving conditions can be any solution or environmental conditions that can mediate or stimulate cleavage of the cleavable bond. For example, some labile bonds can be cleaved in acid conditions, alkaline conditions, in the presence of a reactive group, etc. Non-enzymatic cleaving conditions are any cleaving conditions except the presence of enzymes. Non-agent cleaving conditions are any cleaving conditions except the presence of cleaving agents.

A "protease-activatable CendR element" (or "protease-activated CendR element") refers to an activatable CendR element where the blocking group is coupled to the CendR element via a peptide bond and where the peptide bond can be cleaved by a protease. Cleavage of this peptide bond in a protease-activatable CendR element makes the CendR element capable of internalization into a cell and/or of tissue penetration. In one example, the blocking group can be coupled to the CendR element via a cleavable or labile bond. The cleavable bond can be cleaved by, for example, an enzyme or a chemical compound. Cleavage or 'labilization' bond in an activatable CendR element makes the CendR element capable of internalization into a cell and/or of tissue penetration. Such cleavage or 'labilization' can be referred to as activation of the CendR element. A protease-activatable CendR element is a form of activatable CendR element.

Proteolysis that uncovers a C-terminal element can serve as a switch that triggers the internalization signal. Various compositions can be internalized through this mechanism. For example, homing molecule-mediated accumulation can occur at a target site with cell type-specific proteolysis that exposes a C-terminal element which allows for highly specific homing systems with target-triggered internalization. This protease-controllable internalization system can be useful in engineering compositions with functions such as cell type-specific and/or tissue type-specific uptake and the ability to spread the compositions in tissues.

CendR elements are further described in U.S. Patent Application Publication 2009-0226372, which is hereby incorporated by reference in its entirety, and specifically for its description of the form, structure, and use of CendR elements and peptides.

3. Plaque-Inhibiting Elements

Plaque-inhibiting elements are compounds or compositions that can inhibit, reduce, or prevent atherosclerotic plaques, that can inhibit, reduce, or prevent increase in atherosclerotic plaques, or combinations thereof. Numerous compounds and compositions are known that act as plaque-inhibiting elements and these can be adapted and used in the disclosed compositions as plaque-inhibiting elements. In some forms, the plaque-inhibiting element can be a peptide or a small molecule compound. In some forms, the plaque-inhibiting element can promote apoptosis of a cell in which it is internalized. In some forms, the plaque-inhibiting element can bind p32.

In some forms, the plaque-inhibiting element can be CGNKRTRGC (SEQ ID NO:1), CGQKRTRGC (SEQ ID NO:2), CKRGARSTC (SEQ ID NO:4), CKRGSRSTC (SEQ ID NO:5), or CKRGNRSTC (SEQ ID NO:6).

In some forms, the plaque-inhibiting element can be antiinflammatory agents/cytokines (e.g. AZ876, 3-(3-(2-chloro-3-trifluoromethylbenzyl-2,2diphenylethylamino) proproxy), phenylacetic acid (GW3965), 25-Hydroxycholesterol (HI 015), 22(R)-hydroxycholesterol (H9384), 22(S)-hydroxycholesterol (H5884), N,N-dimethyl-3~hydroxycholenamide (DMHCA), T0901317 [N-(2,2,2,-trifluoro-ethyl)-N-[4-(2,2,2,-trifluoro-1hydroxy-1-trifluoromethyl-ethyl)-phenyl]benzenesulfonamide], hypocholamide, etc.), HMGCoA reductase inhibitors (atorvastatin, Atorvastatin, Amlodipine Besylate, Cerivastatin, Fluvastatin, Lovastatin, Mevastatin, Pitavastatin, Pravastatin, Rosuvastatin, Simvastatin, etc.), RNA, DNA, chemotherapeutic compounds, chemical or biologic inhibitors of inflammatory cytokines, their receptors, or their signaling intermediates, or combinations thereof.

Additional examples of plaque-inhibiting compounds include doxorubicin, 2-aminochromone (U-86983, Upjohn and Pharmacia) (U-86), cytarabine, vincristine, dalteparin sodium, cyclosporine A, colchicines, etoposide, sirolimus, paclitaxel, ceramide, cilostazol, clodronate, pamidronate, alendronate, ISA-13-1, AG-1295, AGL-2043, dexamethasone, everolimus, ABT-578, tacrolimus (FK506), estradiol, lantrunculinD, cytochalasin A, dexamethasone, zotarolimus, angiopeptin, bisphosphonates, estrogen, angiopeptin, ROCK inhibitors, PDGF inhibitors, MMP inhibitors, statins, and well as combinations of these therapies (e.g., a combination of zotarolimus and dexamethasone), as well as any therapeutic disclosed in Circ Res 2003 Apr. 18; 92(7):e62-9. Epub 2003 Mar. 27; J Pharm Sci 1998 October; 87(10): 1229-34; Int J Nanomedicine 2007; 2(2): 143-61; and Atherosclerosis 2002 February; 160(2):259-71.

4. Additional Aspects

In some forms, the CendR-activating element and the plaque-inhibiting element are not covalently coupled or non-covalently associated with each other. In some forms, the CendR peptide and the plaque-inhibiting element are not covalently coupled or non-covalently associated with each other.

As used herein, reference to components (such as a CendR-activating element and a plaque-inhibiting element) as being "not covalently coupled" means that the components are not connected via covalent bonds (for example, that the CendR-activating element and the plaque-inhibiting element are not connected via covalent bonds). That is, there is no continuous chain of covalent bonds between, for example, the CendR-activating element and the plaque-inhibiting element. Conversely, reference to components (such as a CendR-activating element and a cargo composition) as being "covalently coupled" means that the components are connected via covalent bonds (for example, that the CendR-activating element and the cargo composition are connected via covalent bonds). That is, there is a continuous chain of covalent bonds between, for example, the CendR-activating element and the cargo composition. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as a CendR-activating element and a plaque-inhibiting element) as not being "non-covalently associated" means that there is no direct or indirect non-covalent association between the components. That is, for example, no atom covalently coupled to a CendR-activating element is involved in a non-covalent bond with an atom covalently coupled to a plaque-inhibiting element. Within this meaning, a CendR-activating element and a plaque-inhibiting element can be together in a composition where they are indirectly associated via multiple intervening non-covalent bonds while not being non-covalently associated as that term is defined herein. For example, a CendR-activating element and a plaque-inhibiting element can be mixed together in a carrier where they are not directly non-covalently associated. A CendR-activating element and a plaque-inhibiting element that are referred to as not indirectly non-covalently associated cannot be mixed together in a continuous composition. Reference to components (such as a CendR-activating element and a plaque-inhibiting element) as not being "directly non-covalently associated" means that there is no direct non-covalent association between the components (an indirect non-covalent association may be present). Reference to components (such as a CendR-activating element and a plaque-inhibiting element) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

The CendR-activating element and the plaque-inhibiting element can be administered to the subject simultaneously. The CendR-activating element and the plaque-inhibiting element can be administered to the subject in a single composition comprising the CendR-activating element and the plaque-inhibiting element. The CendR-activating element and the plaque-inhibiting element can be administered to the subject in separate compositions. The CendR-activating element and the plaque-inhibiting element can be administered to the subject at different times. The CendR-activating element and the plaque-inhibiting element can be administered to the subject in separate compositions. The CendR-activating element and the plaque-inhibiting element can be administered to the subject by separate routes. In some forms, the CendR-activating element and the plaque-inhibiting element are not bound to each other. The cell, tissue, or both can be exposed to the CendR-activating element and the plaque-inhibiting element by administering the CendR-activating element and the plaque-inhibiting element to the subject. The CendR-activating element and the plaque-inhibiting element can be administered to the subject simultaneously. The CendR-activating element and the plaque-inhibiting element can be administered to the subject in a single composition comprising the CendR-activating element and the plaque-inhibiting element. Such a composition can be administered alone or in combination with any other component, such as those disclosed herein. For example, the CendR/plaque-inhibiting element can be administered or used together with one or more other CendR components, one or more other plaque-inhibiting elements, one or more plaque-inhibiting elements, or any combination of these. The CendR-activating element can be in a composition comprising the CendR-activating element and any other component, such as those disclosed herein. For example, the CendR composition can further comprise one or more plaque-homing elements, one or more other CendR components, one or more plaque-inhibiting elements, or any combination of these.

The disclosed peptides can have a length of up to 10, 20, 30, 40, 50, 100, 150, 200, 250, 300, 400, 500, 1000 or 2000 residues. In some forms, the disclosed peptides can have a length of at least 7, 8, 9, 10, 15, 20, 25, 30, 40, 50, 60, 70, 80, 90, 100 or 200 residues. In some forms, the disclosed peptides can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

It is understood that there are numerous amino acid and peptide analogs which can be incorporated into the disclosed plaque-homing elements, CendR-activating elements, and plaque-inhibiting elements. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —CH$_2$NH—, —CH$_2$S—, —CH$_2$—CH$_2$—, —CH═CH— (cis and trans), —COCH$_2$—, —CH(OH) CH$_2$—, and —CHH$_2$SO. These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH$_2$NH—, CH$_2$CH$_2$—); Spatola et al. Life Sci 38:1243-1249 (1986) (—CH$_2$H$_2$—S); Hann J. Chem. Soc Perkin Trans. I 307-314 (1982) (—CH—CH—, cis and trans); Almquist et al. J. Med. Chem. 23:1392-1398 (1980) (—COCH$_2$—); Jennings-White et al. Tetrahedron Lett 23:2533 (1982) (—COCH$_2$—); Szelke et al. European Appln, EP 45665 CA (1982): 97:39405 (1982) (—CH(OH) CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides as long as activity is preserved. Cysteine residues can be used to cyclize or attach two or more peptides together. This can be beneficial to constrain peptides into particular conformations (Rizo and Gierasch Ann. Rev. Biochem. 61:387 (1992), incorporated herein by reference).

The disclosed compositions can also include, for example, an accessory peptide, an accessory peptide, an accessory molecule, a cargo composition, or combinations thereof. Additional compounds having separate functions can be added to the composition. Such polyfunctional conjugates have at least two functions conferred by different portions of the composition and can, for example, display anti-angiogenic activity or pro-apoptotic activity in addition to selective homing activity.

Association of the components of the disclosed compositions can be aided or accomplished via molecules, conjugates and/or compositions. Where such molecules, conjugates and/or compositions are other than plaque-homing elements, CendR-activating elements and plaque-inhibiting elements, they can be referred to herein as linkers. Such linkers can be any molecule, conjugate, composition, etc. that can be used to associate components of the disclosed compositions. Generally, linkers can be used to associate plaque-homing elements, CendR-activating elements and plaque-inhibiting elements to each other and/or to other molecules and components. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components on the composition. For example, linkers of fibrous form are useful for increasing the number of components per composition or per a given area of the composition. Similarly, linkers having a branching form are useful for increasing the number of components per composition or per a given area of the composition. Linkers can also have a branching fibrous form.

Linkers of different lengths can be used to bind the disclosed plaque-homing elements, CendR-activating elements and plaque-inhibiting elements to each other and/or to other molecules and components. A flexible linker can function well even if relatively short, while a stiffer linker can be longer to allow effective exposure and density. The length of a linker can refer to the number of atoms in a continuous covalent chain between the attachment points on the components being linked or to the length (in nanometers, for example) of a continuous covalent chain between the attachment points on the components being linked. Unless the context clearly indicates otherwise, the length refers to the shortest continuous covalent chain between the attachment points on the components being linked not accounting for side chains, branches, or loops. Due to flexibility of the linker, all of the linkers may not have same distance from the component. Thus linkers with different chain lengths can make the resulting composition more effective (by increasing density, for example). Branched linkers bearing multiple components also allow attachment of more than one component at a given site of the surface molecule. Useful lengths for linkers include at least, up to, about, exactly, or between 3, 4, 5, 6, 7, 8, 9, 10, 15, 20, 25, 30, 35, 40, 45, 50, 60, 70, 80, 90, and 100 atoms. Useful lengths for linkers include at least, up to, about, exactly, or between 10, 15, 20, 25, 30, 35, 40, 45, 50, 60, 70, 80, 90, and 100 nanometers. Any range of these lengths and all lengths between the listed lengths are specifically contemplated.

Hydrophilic or water-solubility linkers can increase the mobility of the attached components. Examples of water-soluble, biocompatible polymers which can serve as linkers include, but are not limited to polymers such polyethylene glycol (PEG), polyethylene oxide (PEO), polyvinyl alcohol, polyhydroxyethyl methacrylate, polyacrylamide, and natural polymers such as hyaluronic acid, chondroitin sulfate, carboxymethylcellulose, and starch. Useful forms of branched tethers include star PEO and comb PEO. Star PEO can be formed of many PEO "arms" emanating from a common core.

Polyethylene glycols (PEGs) are simple, neutral polyethers which have been given much attention in biotechnical and biomedical applications (Milton Harris, J. (ed) "Poly(ethylene glycol) chemistry, biotechnical and biomedical applications" Plenum Press, New York, 1992). PEGs are soluble in most solvents, including water, and are highly hydrated in aqueous environments, with two or three water molecules bound to each ethylene glycol segment; this hydration phenomenon has the effect of preventing adsorption either of other polymers or of proteins onto PEG-modified surfaces. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes. Appropriate molecular weights for PEG linkers used in the disclosed compositions can be from about 120 daltons to about 20 kilodaltons. For example, PEGs can be at least, up to, about, exactly, or between 100, 150, 200, 250, 300, 350, 400, 450, 500, 600, 700, 800, 900, 1000, 1200, 1400, 1500, 1600, 1800, 2000, 2500, 3000, 3500, 4000, 4500, 5000, 5500, 6000, 6500, 7000, 7500, 8000, 8500, 9000, 9500, 10,000, 20,000, 30,000, 40,000, and 50,000 daltons. Any range of these masses and all masses between the listed masses are specifically contemplated. PEGs are usually available as mixtures of somewhat heterogeneous masses with a stated average mass (PEG-5000, for example).

The disclosed compositions can be produced using any suitable techniques. Many techniques, reactive groups, chemistries, etc. for linking components of the types disclosed herein are known and can be used with the disclosed components and compositions.

Protein crosslinkers that can be used to crosslink the plaque-homing elements, CendR-activating elements and plaque-inhibiting elements to each other and/or to other molecules, elements, moieties, etc. are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy) ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of the disclosed compositions, such as the plaque-homing elements, CendR-activating elements and plaque-inhibiting elements, can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the component. The reaction can be performed, for example, in aqueous solution at room temperature for 4 hours. This coupling chemistry can be used to couple components of the compositions.

Components of the disclosed compositions, such as the plaque-homing elements, CendR-activating elements and plaque-inhibiting elements, can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., Pharm. Rev. 53, 283-318 (2001)). The particles can have surface modifications, for example, for reticuloendothelial system avoidance (PEG) and homing (homing molecules), endosome escape (pH-sensitive peptide; for example, Pirollo et al., Cancer Res. 67, 2938-43 (2007)), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery.

The disclosed peptides can have additional N-terminal, C-terminal, or intermediate amino acid sequences, e.g., amino acid linkers or tags. The term "amino acid linker" refers to an amino acid sequences or insertions that can be used to connect or separate two distinct peptides, polypeptides, or polypeptide fragments, where the linker does not otherwise contribute to the essential function of the composition. The term "amino acid tag" refers to a distinct amino acid sequence that can be used to detect or purify the provided polypeptide, wherein the tag does not otherwise contribute to the essential function of the composition. The disclosed peptides can further have deleted N-terminal, C-terminal or intermediate amino acids that do not contribute to the essential activity of the peptides and polypeptides.

Plaque-homing elements, CendR-activating elements, plaque-inhibiting elements and other components can be directly or indirectly covalently bound to each other and/or to other components by any functional group (e.g., amine, carbonyl, carboxyl, aldehyde, alcohol). For example, one or more amine, alcohol or thiol groups on the components can be reacted directly with isothiocyanate, acyl azide, N-hydroxysuccinimide ester, aldehyde, epoxide, anhydride, lactone, or other functional groups incorporated onto the plaque-homing elements, CendR-activating elements, plaque-inhibiting elements, or other components. Schiff bases formed between the amine groups on the components and aldehyde groups on other components can be reduced with agents such as sodium cyanoborohydride to form hydrolytically stable amine links (Ferreira et al., J. Molecular Catalysis B: Enzymatic 2003, 21, 189-199). Plaque-homing elements, CendR-activating elements, plaque-inhibiting elements and other components can be coupled to each other and/or to other components by, for example, the use of a heterobifunctional silane linker reagent, or by other reactions that activate functional groups on either the components.

Useful modes for linking plaque-homing elements, CendR-activating elements, and plaque-inhibiting elements to each other and/or to other components include heterobifunctional linkers or spacers. Such linkers can have both terminal amine and thiol reactive functional groups for reacting amines on components with sulfhydryl groups, thereby coupling the components in an oriented way. These linkers can contain a variable number of atoms. Examples of such linkers include, but are not limited to, N-Succinimidyl 3-(2-pyridyldithio)propionate (SPDP, 3- and 7-atom spacer), long-chain-SPDP (12-atom spacer), (Succinimidyloxycarbonyl-a-methyl-2-(2-pyridyldithio) toluene) (SMPT, 8-atom spacer), Succinimidyl-4-(N-maleimidomethyl)cyclohexane-1-carboxylate) (SMCC, 11-atom spacer) and Sulfosuccinimidyl-4-(N-maleimidomethyl)cyclohexane-1-carboxylate, (sulfo-SMCC, 11-atom spacer), m-Maleimidobenzoyl-N hydroxysuccinimide ester (MBS, 9-atom spacer), N-(g-maleimidobutyryloxy)succinimide ester (GMBS, 8-atom spacer), N-(g-maleimidobutyryloxy) sulfosuccinimide ester (sulfo-GMBS, 8-atom spacer), Succinimidyl 6-((iodoacetyl) amino) hexanoate (SIAX, 9-atom spacer), Succinimidyl 6-(6-(((4-iodoacetyl)amino)hexanoyl)amino)hexanoate (SI-AXX, 16-atom spacer), and p-nitrophenyl iodoacetate (NPIA, 2-atom spacer). One ordinarily skilled in the art also will recognize that a number of other coupling agents or links, with different number of atoms, may be used.

Hydrophilic spacer atoms can be incorporated into linkers to increase the distance between the reactive functional groups. For example, polyethylene glycol (PEG) can be incorporated into sulfo-GMBS. Hydrophilic molecules such as PEG have also been shown to decrease non-specific binding (NSB) and increase hydrophilicity of surfaces when covalently coupled. PEG can also be used as the primary linker material.

Free amine groups of components can also be attached to plaque-homing elements, CendR-activating elements, plaque-inhibiting elements, and other components containing reactive amine groups via homobifunctional linkers. Linkers such as dithiobis(succinimidylpropionate) (DSP, 8-atom spacer), disuccinimidyl suberate (DSS, 8-atom spacer), glutaraldehyde (4-atom spacer), Bis[2-(succinimidyloxycarbonyloxy)ethyl]sulfone (BSOCOES, 9-atom spacer), all requiring high pH, can be used for this purpose. Examples of homobifunctional sulfhydryl-reactive linkers include, but are not limited to, 1,4-Di-[3'-2'-pyridyldithio) propion-amido]butane (DPDPB, 16-atom spacer) and Bis-maleimidohexane (BMH, 14-atom spacer).

When it is desirable to achieve high coupling density, additional amino groups can be added to the surface molecules (such as commercially obtained SPIO) as follows: First, to crosslink the particles before the amination step, add 3 ml of the colloid (~10 mgFe/ml in double-distilled water) to 5 ml of 5M NaOH and 2 ml of epichlorohydrin (Sigma, St. Louis, Mo.). Agitate the mixture for 24 hours at room temperature to promote interaction between the organic phase (epichlorohydrin) and aqueous phase (dextran-coated particle colloid) in order to remove excess epichlorohydrin, and dialyze the reacted mixture against double-distilled water for 24 hours using a dialysis cassette (10,000 Da cutoff, Pierce, Rockford Ill.). Add amino groups to the surface of the particles as follows: add 0.02 ml of concentrated ammonium hydroxide (30%) to 1 ml of colloid (~10 mg Fe/ml). Agitate the mixture at room temperature for 24 hours. Dialyze the reacted mixture against double-distilled water for 24 hours. To further rinse the particles, trap the colloid on a MACS® Midi magnetic separation column (Miltenyi Biotec, Auburn Calif.), rinse with PBS three times, and elute from the column with 1 ml PBS.

The composition can further comprise a co-composition. The co-composition can comprise a therapeutic agent. The co-composition can comprise a detection agent. The co-composition can comprise a carrier, vehicle, or both. The co-composition can comprise, for example, a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

The composition can further comprise a cargo composition. The cargo composition can comprise a therapeutic agent. The cargo composition can comprise a detection agent. The cargo composition can comprise a carrier, vehicle, or both. The cargo composition can comprise, for example, a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

In some forms, the disclosed compounds can be pharmaceutically acceptable nontoxic ester, amide, and salt derivatives of the disclosed compounds containing a carboxylic acid moiety. In some forms, the disclosed compounds can be pharmaceutically acceptable esters, amides, and salts of the disclosed compounds. Pharmaceutically acceptable salts can be prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In some forms, the reaction can be conducted in water, alone or in combination with an inert, water-miscible organic solvent, at a temperature of from about 0° C. to about 100° C. such as at room temperature. The molar ratio of the disclosed compounds to base used can be chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below- and accordingly can serve as prodrugs. Generally, these derivatives will be lower alkyl esters such as methyl, ethyl, and the like. Amide derivatives —(CO)$NH_2$, —(CO)NHR and —(CO)$NR_2$, where R is an alkyl group, can be prepared by reaction of the carboxylic acid-containing compound with ammonia or a substituted amine.

B. Nanoparticles

The disclosed composition can also include a carrier for the composition and/or for different components of the composition. Useful carriers include nanoparticles. The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohoms, nano-onions, nanorods, nanoropes and quantum dots. A nanoparticle can produce a detectable signal, for example, through absorption and/or emission of photons (including radio frequency and visible photons) and plasmon resonance.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

In some forms, the nanoparticles can have an average or mean diameter of no greater than about 1000 nanometers (nm), such as no greater than about any of 900, 800, 700, 600, 500, 400, 300, 200, and 100 nm. In some forms, the average or mean diameters of the nanoparticles can be no greater than about 200 nm. In some forms, the average or mean diameters of the nanoparticles can be no greater than about 150 nm. In some forms, the average or mean diameters of the nanoparticles can be no greater than about 100 nm. In some forms, the average or mean diameter of the nanoparticles can be about 20 to about 400 nm. In some forms, the average or mean diameter of the nanoparticles can be about 40 to about 200 nm. In some embodiments, the nanoparticles are sterile-filterable.

The nanoparticles can be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

Plaque-homing elements, CendR-activating elements, plaque-inhibiting elements, and other components can be bound to carrier proteins. Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some forms, the carrier protein is non-blood protein, such as casein, α-lactalbumin, and β-lactoglobulin. The carrier proteins may either be natural in origin or synthetically prepared. Preferably, the linkage occurs in the subject's blood after administration of the composition. In some forms, the carrier comprises albumin, such as human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, JAMA 237:355-360, 460-463 (1977)) and Houser et al., Surgery, Gynecology and Obstetrics, 150:811-816 (1980)) and in conjunction with exchange transfusion in the treatment of neonatal hyperbilirubinemia (see, e.g., Finlayson, Seminars in Thrombosis and Hemostasis, 6:85-120 (1980)). Other albumins are contemplated, such as bovine serum albumin. Use of such non-human albumins could be appropriate, for example, in the context of use of these compositions in non-human mammals, such as the veterinary (including domestic pets and agricultural context).

Carrier proteins (such as albumin) in the composition generally serve as a carrier for the hydrophobic cargo molecules, i.e., the carrier protein in the composition makes the cargo molecules more readily suspendable in an aqueous medium or helps maintain the suspension as compared to compositions not comprising a carrier protein. This can avoid the use of toxic solvents (or surfactants) for solubilizing the cargo molecules, and thereby can reduce one or more side effects of administration of the cargo molecules into an individual (such as a human). Thus, in some embodiments, the disclosed composition can be substantially free (such as free) of surfactants, such as Cremophor (including Cremophor EL® (BASF)). In some forms, the composition can be substantially free (such as free) of surfactants. A composition is "substantially free of Cremophor" or "substantially free of surfactant" if the amount of Cremophor or surfactant in the composition is not sufficient to cause one or more side effect(s) in an individual when the composition is administered to the individual.

The amount of carrier protein in the disclosed compositions will vary depending on other components in the composition. In some forms, the plaque-homing element, CendR-activating element, and/or plaque-inhibiting element can comprise a carrier protein in an amount that is sufficient to stabilize the element in an aqueous suspension, for example, in the form of a stable colloidal suspension (such as a stable suspension of nanoparticles). In some embodiments, the carrier protein is in an amount that reduces the sedimentation rate of the composition in an aqueous medium. For particle-containing compositions, the amount of the carrier protein also depends on the size and density of nanoparticles.

Methods of making nanoparticle compositions are known in the art. For example, nanoparticles containing components can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1. For example, the hydrophobic carrier molecules can be dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells.

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. These MLVs were first described by Bangham, et al., J Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 μm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposome are oligolamellar vesicles ("OLVs"), which have a large center compartment surrounded by several peripheral lipid layers. These vesicles, having a diameter of 2-15 μm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

"Micelle" as used herein refers to a structure comprising an outer lipid monolayer. Micelles can be formed in an aqueous medium when the Critical Micelle Concentration (CMC) is exceeded. Small micelles in dilute solution at approximately the critical micelle concentration (CMC) are generally believed to be spherical. However, under other conditions, they may be in the shape of distorted spheres, disks, rods, lamellae, and the like. Micelles formed from relatively low molecular weight amphiphile molecules can have a high CMC so that the formed micelles dissociate rather rapidly upon dilution. If this is undesired, amphiphile molecules with large hydrophobic regions can be used. For example, lipids with a long fatty acid chain or two fatty acid chains, such as phospholipids and sphingolipids, or polymers, specifically block copolymers, can be used.

Polymeric micelles have been prepared that exhibit CMCs as low as $10^{-6}$ M (molar). Thus, they tend to be very stable while at the same time showing the same beneficial characteristics as amphiphile micelles. Any micelle-forming polymer presently known in the art or as such may become known in the future may be used in the disclosed compositions and methods. Examples of micelle-forming polymers include, without limitation, methoxy poly(ethylene glycol)-b-poly(ε-caprolactone), conjugates of poly(ethylene glycol) with phosphatidyl-ethanolamine, poly(ethylene glycol)-b-polyesters, poly(ethylene glycol)-b-poly(L-aminoacids), poly(N-vinylpyrrolidone)-b1-poly(orthoesters), poly(N-vinylpyrrolidone)-b-polyanhydrides and poly(N-vinylpyrrolidone)-b-poly(alkyl acrylates).

Micelles can be produced by processes conventional in the art. Examples of such are described in, for example, Liggins (Liggins, R. T. and Burt, H. M., "Polyether-polyester diblock copolymers for the preparation of paclitaxel loaded polymeric micelle formulations." Adv. Drug Del. Rev. 54: 191-202, (2002)); Zhang, et al. (Zhang, X. et al., "Development of amphiphilic dibiock copolymers as micellar carriers of taxol." Int. J. Pharm. 132: 195-206, (1996)); and Churchill (Churchill, J. R., and Hutchinson, F. G., "Biodegradable amphipathic copolymers." U.S. Pat. No. 4,745,160, (1988)). In one such method, polyether-polyester block copolymers, which are amphipathic polymers having hydrophilic (polyether) and hydrophobic (polyester) segments, are used as micelle forming carriers.

Another type of micelle can be formed using, for example, AB-type block copolymers having both hydrophilic and hydrophobic segments, as described in, for example, Tuzar (Tuzar, Z. and Kratochvil, P., "Block and graft copolymer micelles in solution.", Adv. Colloid Interface Sci. 6:201-232, (1976)); and Wilhelm, et al. (Wilhelm, M. et al., "Poly(styrene-ethylene oxide) block copolymer micelle formation in water: a fluorescence probe study.", Macromolecules 24: 1033-1040 (1991)). These polymeric micelles are able to maintain satisfactory aqueous stability. These micelles, in the range of approximately <200 nm in size, are effective in reducing non-selective RES scavenging and show enhanced permeability and retention.

Further, U.S. Pat. No. 5,929,177 to Kataoka, et al. describes a polymeric molecule which is usable as, inter alia, a drug delivery carrier. The micelle is formed from a block copolymer having functional groups on both of its ends and which comprises hydrophilic/hydrophobic segments. The polymer functional groups on the ends of the block copolymer include amino, carboxyl and mercapto groups on the α-terminal and hydroxyl, carboxyl group, aldehyde group and vinyl group on the ω-terminal. The hydrophilic segment comprises polyethylene oxide, while the hydrophobic segment is derived from lactide, lactone or (meth)acrylic acid ester.

Further, for example, poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hr, or a temperature as high as 190° C. can be used if the reaction is carried out for only about 2 hr.

As another example, N-isopropylacrylamide ("IPAAm") (Kohjin, Tokyo, Japan) and dimethylacrylamide ("DMAAm") (Wako Pure Chemicals, Tokyo, Japan) can be used to make hydroxyl-terminated poly(IPAAm-co-DMAAm) in a radical polymerization process, using the method of Kohori, F. et al. (1998). (Kohori, F. et al., "Preparation and characterization of thermally Responsive block copolymer micelles comprising poly(N-isopropylacrylamide-b-D,L-lactide)." J. Control. Rel. 55: 87-98, (1998)). The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori, F. et al. (1999). (Kohori, F. et al., "Control of adriamycin cytotoxic activity using thermally responsive polymeric micelles composed of poly(N-isopropylacrylamide-co-N,N-dimethylacrylamide)-b-poly(D,L-lacide).-", Colloids Surfaces B: Biointerfaces 16: 195-205, (1999)).

Examples of block copolymers from which micelles can be prepared are found in U.S. Pat. No. 5,925,720, to Kataoka, et al., U.S. Pat. No. 5,412,072 to Sakarai, et al., U.S. Pat. No. 5,410,016 to Kataoka, et al., U.S. Pat. No. 5,929,177 to Kataoka, et al., U.S. Pat. No. 5,693,751 to Sakurai, et al., U.S. Pat. No. 5,449,513 to Yokoyama, et al., WO 96/32434, WO 96/33233 and WO 97/0623, the contents of all of which are incorporated by reference. Modifications thereof which are prepared by introducing thereon a suitable functional group (including an ethyleneically unsaturated polymerizable group) are also examples of block copolymers from which micelles of the present invention are preferably prepared. Preferable block copolymers are those disclosed in the above-mentioned patents and or international patent publications. If the block copolymer has a sugar residue on one end of the hydrophilic polymer segment, as in the block copolymer of WO 96/32434, the sugar residue should preferably be subjected to Malaprade oxidation so that a corresponding aldehyde group may be formed.

Lipids are synthetically or naturally-occurring molecules which includes fats, waxes, sterols, prenol lipids, fat-soluble vitamins (such as vitamins A, D, E and K), glycerolipids, monoglycerides, diglycerides, triglycerides, glycerophospholipids, sphingolipids, phospholipids, fatty acids monoglycerides, saccharolipids and others. Lipids can be hydrophobic or amphiphilic small molecules; the amphiphilic nature of some lipids allows them to form structures such as monolayers, vesicles, micelles, liposomes, bi-layers or membranes in an appropriate environment, i.e., aqueous environment. Any of a number of lipids can be used as amphiphile molecules, including amphipathic, neutral, cationic, and anionic lipids. Such lipids can be used alone or in combination, and can also include bilayer stabilizing components such as polyamide oligomers (see, e.g., U.S. Pat.

No. 6,320,017, "Polyamide Oligomers", by Ansell), peptides, proteins, detergents, lipid-derivatives, such as PEG coupled to phosphatidylethanolamine and PEG conjugated to ceramides (see, U.S. Pat. No. 5,885,613). In a preferred embodiment, cloaking agents, which reduce elimination of liposomes by the host immune system, can also be included, such as polyamide-oligomer conjugates, e.g., ATTA-lipids, (see, U.S. patent application Ser. No. 08/996,783, filed Feb. 2, 1998) and PEG-lipid conjugates (see, U.S. Pat. Nos. 5,820,873, 5,534,499 and 5,885,613).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

Cationic lipids, carry a net positive charge at physiological pH, can readily be used as amphiphile molecules. Such lipids include, but are not limited to, N,N-dioleyl-N,N-dimethylammonium chloride ("DODAC"); N-(2,3-dioleyloxy) propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3.beta.-(N—(N',N'-dimethylaminoethane)-carbamoyl)cholesterol ("DC-Chol"), N-(1-(2,3-dioleyloxy)propyl)-N-2-(sperminecarboxamido) ethyl)-N,N-dimethyl-ammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids can be used as amphiphile molecules and include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Amphiphatic lipids can also be suitable amphiphile molecules. "Amphipathic lipids" refer to any suitable material, wherein the hydrophobic portion of the lipid material orients into a hydrophobic phase, while the hydrophilic portion orients toward the aqueous phase. Such compounds include, but are not limited to, fatty acids, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lyso-phosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols. Zwitterionic lipids are a form of amphiphatic lipid.

Sphingolipids are fatty acids conjugated to the aliphatic amino alcohol sphingosine. The fatty acid can be covalently bond to sphingosine via an amide bond. Any amino acid as described above can be covalently bond to sphingosine to form a sphingolipid. A sphingolipid can be further modified by covalent bonding through the α-hydroxyl group. The modification can include alkyl groups, alkenyl groups, alkynyl groups, aromatic groups, heteroaromatic groups, cyclyl groups, heterocyclyl groups, phosphonic acid groups. Non-limiting examples of shingolipids are N-acylsphingosine, N-Acylsphingomyelin, Forssman antigen.

Saccharolipids are compounds that contain both fatty acids and sugars. The fatty acids are covalently bonded to a sugar backbone. The sugar backbone can contain one or more sugars. The fatty acids can bond to the sugars via either amide or ester bonds. The sugar can be any sugar base. The fatty acid can be any fatty acid as described elsewhere herein. The provided compositions can comprise either natural or synthetic saccharolipids. Non-limiting saccharolipids are UDP-3-O-(β-hydroxymyristoyl)-GlcNAc, lipid IV A, Kdo2-lipid A.

Examples of lipids useful for conjugation to the disclosed peptides, compounds, and compositions include, for example, dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

C. Mixtures

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

Methods

Disclosed are methods of treating atherosclerosis in a subject by administering one or more of the disclosed compositions. In some forms, the subject is at risk of atherosclerosis. In some forms, the subject has atherosclerosis. Also disclosed are methods of making the disclosed compositions.

Also disclosed are methods of identifying and methods of assessing compounds that can bind p32, can bind NRP-1, NRP-2, or both, can inhibit atherosclerotic plaques, or a combination. Also disclosed are methods of identifying and methods of assessing compounds that can home to or target plaques, can activate the CendR pathway, can promote the CendR bystander effect, can inhibit atherosclerotic plaques, or a combination.

A. Methods of Assessing and Making

The disclosed peptides can be made using any suitable technique. Many techniques are known and can be used to make the disclosed peptides. For example, peptides can be synthesized with an automatic microwave assisted peptide synthesizer (Liberty; CEM, Matthews, N.C.) using standard solid-phase Fmoc/t-Bu chemistry with 2-(1H-7-azabenzotriazol-1-yl)-1,1,3,3-tetramethyl uronium hexafluorophosphate methanaminium (Anaspec, Inc., San Jose, Calif.) as the coupling reagent. During synthesis, the peptides were labeled with 5(6)-carboxyfluorescein (FAM) (Sigma-Aldrich, St. Louis, Mo.) with a 6-aminohexanoic acid spacer separating the dye from the sequence. The peptides were cleaved from the resin using 95% trifluoroacetic acid (Sigma-Aldrich, St. Louis, Mo.) with 2.5% water and tri-isiopropylsilane (Sigma-Aldrich, St. Louis, Mo.). Subsequent purification by High Performance Liquid Chromatography (Gilson Inc., Middleton, Wis.) gave peptides with >90% purity.

Nanoworms (NWs) coated with peptides can be prepared, for example, as described by Agemy et al., Blood. 116 (2010) 2847-2856, or Park et al., Small. 5 (2009) 694-700. Aminated nanoworms can be pegylated with, for example, maleimide-5KPEG-NHS (JenkemTechnology, City, China). The aminated nanoworms can be pegylated with, for example, maleimide-5KPEG-NHS (JenkemTechniology, China). Peptides can be conjugated to nanoparticles through a thioether bond between a cysteine thiol from the peptide sequence and the maleimide on the functionalized particles.

Peptides useful for systemic treatment to inhibit plaque formation can be identified and assessed by, for example, testing in an ApoE null-based atherosclerosis model. Peptides useful for systemic treatment with the peptide alone (with no drug attached to it) can also be identified and assessed by, for example, testing in an ApoE null-based atherosclerosis model. For example, high efficacy peptides can be identified and assessed using such models. The disclosed peptides are based on three approaches to increase in vivo peptide efficacy. The first approach identifies peptides that have a higher affinity for p32 than LyP-1. The TT1 peptide is an example of such a peptide. The second approach prolongs the blood half-life of the peptide by having the peptide form a disulfide bond to albumin in the blood stream. The third approach is to make the peptide both long-circulating and multivalent by coupling it to nanoparticles. These approaches have been used in other systems (Agemy et al., Proc Natl Acad Sci USA. 2011; 108(42): 17450-17455; Ruoslahti, Adv Mater. 2012; 24(28):3747-3756). Any one or any combination of approaches can be used for the disclosed peptides.

Testing shows that TT1 homes to plaques as well as or better than LyP-1. For the test, ApoE null mice that have been kept on a high-fat diet can be intravenously injected with 100 μg of the FAM-labeled peptides. One hour later, the mice can be perfused through the heart under anesthesia, and tissues were collected. Accumulation of FAM-labeled peptides can be visualized with UV excitation. Atherosclerotic aortas can be sectioned at the aortic root level, and examined by confocal microscopy. Detection of FAM-LyP-1 and FAM-TT1 signal inside plaques indicates successful homing, whereas a control peptide does not accumulate in the plaques. CD31 staining can be used to visualize the endothelium over the plaque. This can show peptides that home to and penetrate into plaque tissue as well as or better than LyP-1. This assay can be used to identify or assess any peptide for use in homing to and treating atherosclerosis. Such results can also be assessed or confirmed by quantitative comparison.

Figure 13A:
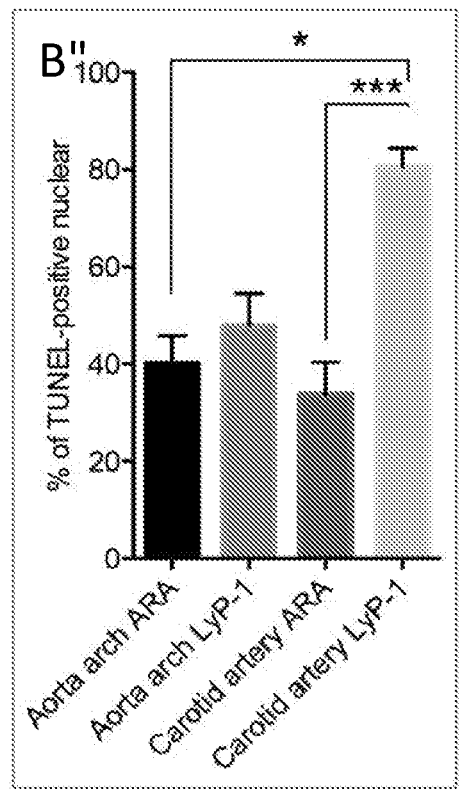
FIGS. 13A and 13B are graphs showing apoptosis in plaques. ApoE null mice with aortic and carotid plaque were intravenously injected with LyP-1 or control (ARA) peptide (200 µg of peptide), and aortas and carotid arteries were collected 3 and 24 h later. The tissues were sectioned and stained with CD68 antibody to label plaque macrophages, and with a TUNEL kit to detect apoptotic cells. (A) Quantitative comparison of percentage of nuclei positive for TUNEL staining in the two types of plaques. (B) Macrophages positive for TUNEL staining after control (ARA) and LyP-1 treatment. Quantification of the 24-h TUNEL data. N=3; *, P<0.05; ***, P<0.005. She et al., Arteriosclerosis, thrombosis, and vascular biology. 2016; 36(1):49-59.
Figure 13B:
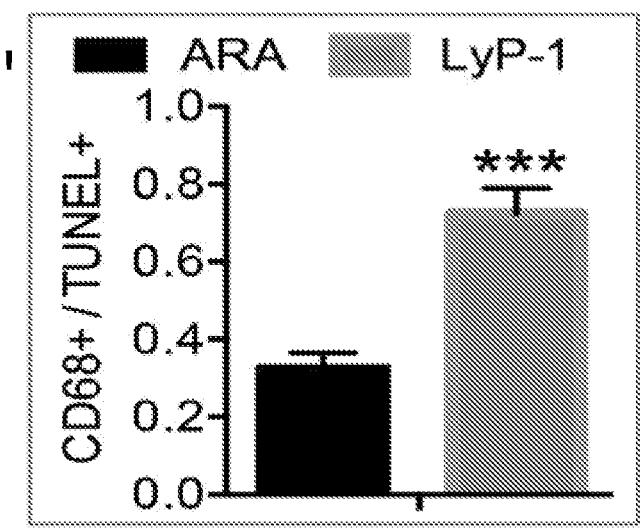

The disclosed peptides can also be identified or assessed for their effect on macrophage apoptosis in plaques. An example of such analysis is shown in FIG. 13. Briefly, ApoE null mice with aortic and carotid plaque can be intravenously injected with LyP-1 or control (ARA) peptide (200 μg of peptide), and aortas and carotid arteries collected 3 and 24 h later. The tissues can be sectioned and stained with CD68 antibody to label plaque macrophages and with a TUNEL kit to detect apoptotic cells. The appearance of staining, the quantification of staining, or both can be used to identify the effect on macrophages.

The blood half-life of the disclosed peptides can increased by designing the peptides to bind albumin in the blood. For example, an unpaired cysteine included in the peptide or tethered to the peptide can bond to albumin and thereby be protected in the blood. The free sulfhydryl forms a disulfide bond with a reactive sulfhydryl in albumin, and the peptide will subsequently circulate as a peptide-albumin complex, which reduces filtration of the peptide into the urine. The circulation time of a cyclic peptide similar to LyP-1 was increased by including an unpaired cysteine attached through a linker (Pang et al., J Control Release. 2014b; 175:48-53). The half-life typically increases from 10 min to 3 hours (Pang et al., J Control Release. 2014b; 175:48-53; Pang et al., J Control Release. 2014b; 175:48-53). The synthesis of 3-cysteine cyclic peptides, such LyP-1, can be accomplished routinely (Karmali et al., Nanomedicine: nanotechnology, biology, and medicine. 2009; 5(1):73-82; Sugahara et al., Cancer Cell. 2009; 16(6):510-520).

The blood half-life of the disclosed peptides can also increased by displaying the peptides on nanoparticles. Nanoparticles displaying the disclosed peptides on their surface can be prepared by, for example, coupling the peptides to lipid-tailed PEG via a cysteine incorporated into the peptide or tethered to the peptide. The peptide-lipid-tailed PGA can then spontaneously assembles into a micelle that displays the peptides on their surface. Synthesized and characterized of such micelles can be accomplished using known techniques (Karmali et al., Nanomedicine: nanotechnology, biology, and medicine. 2009; 5(1):73-82; She et al., ACS Nano. 2014; 8(10): 10139-10149). Peptide-displaying micelles are of particular interest since they include two features to increase efficacy: prolonged circulation time and multivalent presentation.

The bystander effect allows compositions that can deliver a greater therapeutic effect of a therapeutic compound with the same or even a lower dose of the therapeutic compound. For example, the LXR agonist GW3965 is a promising drug that has been shown to reduce plaque (Feig et al., J Clinical Investigation. 2010; 120(12):4415-4424; Joseph et al., Proc Natl Acad Sci USA. 2002; 99(11):7604-7609). Unfortunately, GW3965 has some serious systemic side effects that tend to negate its positive effects on plaque (Grefhorst et al., J Biol Chem. 2002; 277(37):34182-34190). By administering GW3965 together with a plaque-homing peptide or compound and a CendR-activating peptide or compound (or a peptide or compound that has both activities, such as LyP-1), this drug can be made active in plaque at a dose that minimizes the side effects. Moreover, in the case of LyP-1 (which has plaque-inhibiting activity), the different modes of action of GW3965 and LyP-1 could produce increased therapeutic effect.

The bystander effect can be assessed by using Evans Blue accumulation in plaques with and without co-injection of a peptide or compound to be assessed (Pang et al., Nat Commun. 2014a; 5:4904; Pang et al., J Control Release. 2014b; 175:48-53; Sugahara et al., Science 2010; 328 (5981):1031-1035). Evans Blue binds to albumin in vivo, so these results relate to the extravasation of albumin. Enhancement in Evans Blue accumulation by a factor of 3 would indicate a bystander effect similar to that of iRGD in tumors.

CendR pathway activation works best if the co-injected compound has its own affinity for tor the target tissue because that drives the accumulation at the target, once the CendR pathway has provided access. For example, GW3965 has its own nuclear receptor in plaque cells and so receptor binding may amplify the bystander effect of the CendR-activating element. This can be assessed by, for example, co-administering a plaque-inhibiting element and a CendR-activating element and comparing extravasation observed with the plaque-inhibiting element co-administered with PBS or an inert peptide (ARA). Mass spectrometry can be used to quantify the drug in plaques and in major organs at various time points after administration.

The bystander effect can also be assessed using animal models. For example, ApoE null mice kept on a high-fat diet can be intravenously injected with 100 µmol of a labeled peptide or compound. An hour later, the mice are perfused through the heart under anesthesia, and organs collected, sectioned and examined by confocal microscopy. Strong fluorescence seen inside plaque in a cross-section of the aorta from the peptide- or compound-injected mice, but not in the aortas of mice injected with a control peptide (such as FAM-ARALPSQRSR-NH$_2$; ARA; SEQ ID NO:23), control compound, or vehicle alone (PBS), indicates effective extravasation.

Enhanced delivery of drugs to plaques can also be accomplished by conjugated delivery (combining the plaque-homing, CendR-activating, and plaque-inhibiting functions in a single conjugate. For example, the plaque-homing element and plaque-inhibiting element can be attached or incorporated into a nanoparticle. Iron oxide and protein cage nanoparticles, for example, can be delivered to plaques (Hamzah et al., Proc Natl Acad Sci USA. 2011; 108(17):7154-7159). As a more specific example, GW3965 can be encapsulated in micelles.

Plaque can be measured by quantitation of en face aorta lesion area (She et al., Circulation research. 2009; 104(10): 1160-1168). In this assessment, the entire mouse aorta is dissected from the proximal ascending aorta to the bifurcation of the iliac artery under a dissecting microscope (Mullick et al., J Clin Invest. 2005; 115(11):3149-3156). The adventitial fat is removed, the aorta is opened longitudinally, pinned flat onto black dissecting wax and stained with, for example, Sudan IV. Images of the aortas are taken at, for example, a fixed magnification using, for example, a Nikon DXM1200 Color CCD 12 megapixel camera. The results can be reported as percentage of the total aortic area that contains lesions. Histological examination and quantification of lesion volume can be performed on aorta sections at the aortic sinus level. Carotid artery plaque area can be quantified directly on tissue sections. These measurements focus on a sensitive and invariant location for measuring lesion severity (Mullick et al., J Experimental Medicine. 2008; 205(2):373-383; Mullick et al., J Clin Invest. 2005; 115(11):3149-3156). Macrophages in plaques can be assessed by staining for CD 11b and CD68 (Hamzah et al., Proc Natl Acad Sci USA. 2011; 108(17):7154-7159).

The atherosclerosis data can be analyzed by the unpaired t-test (for normally distributed values, as common with aortic sinus lesion volume) or the non-parametric Mann-Whitney rank sum test (for non-normally distributed values, as common with aortic lesion area percent). ANOVA or the non-parametric Kruskal-Wallis ANOVA on Ranks can be used to determine if differences among multiple (greater than 2) groups (1-factor ANOVA) with multiple treatments (2-factor ANOVA) exist with the treatment. For each data set, a Normality Test (P>0.05) and an Equal Variance Test (P>0.05) can be performed to identity normally distributed data. If either test fails, the non-parametric test can be performed. Pearson product moment correlations can be performed to measure the strength of associations between measures of lesion burden and disease risk. Statistical analysis can be done with the use of, for example, the SigmaStat 3.00 (SPSS, Inc.). A value of p<0.05 is considered significant. The power calculations are based on previous experiments (Glass and Witztum, Cell. 2001; 104(4):503-516; She et al., Arteriosclerosis, thrombosis, and vascular biology. 2016; 36(1):49-59).

Compounds that can bind p32 can be identified by, for example, screening a library of compounds for competitive binding with a known p32 binder, such as LyP-1 peptide or compounds #008 or #989. Similarly, compounds that can bind NRP-1, NRP-2, or both, can be identified by, for example, screening a library of compounds for competitive binding with a known NRP-1/NRP-2 binder, such as CREKA peptide, LyP-1 peptide, or RPARPAR peptide. Use of a peptide or compound that is known to home to plaques is preferred. Such competitive binding assays (examples of which are described in the examples) can focus hit compounds on those that bind to the target in a functionally important location. Such assays can also be used to guide and assess structure activity relationship (SAR) of any hit compounds and their variants.

The disclosed compounds can be readily synthesized using techniques generally known to synthetic organic chemists.

B. Administration

The compositions can comprise, and/or can be administered in vivo in, a pharmaceutically acceptable carrier. By "pharmaceutically acceptable" is meant a material that is not biologically or otherwise undesirable, i.e., the material can be administered to a subject, along with the plaque-homing element, CendR-activating element, and plaque-inhibiting element, without causing any undesirable biological effects or interacting in a deleterious manner with any of the other components of the pharmaceutical composition in which it is contained. The carrier would naturally be selected to minimize any degradation of the plaque-homing element, CendR-activating element, and plaque-inhibiting element and to minimize any adverse side effects in the subject, as would be well known to one of skill in the art. The materials can be in solution, suspension (for example, incorporated into microparticles, liposomes, or cells).

The compositions can be used therapeutically in combination with a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

The preparation can be administered to a subject or organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to a subject or organism.

Herein the term "active ingredient" refers to the preparation accountable for the biological effect. For example, plaque-homing element, CendR-activating elements, and plaque-inhibiting elements that have a biological effect can be considered active ingredients.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist."

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

In one aspect, the compounds described herein can be administered to a subject comprising a human or an animal including, but not limited to, a mouse, dog, cat, horse, bovine or ovine and the like, that is in need of alleviation or amelioration from a recognized medical condition.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need of treatment of atherosclerosis or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

Any of the disclosed compounds, peptides, or compositions can be used therapeutically in combination with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

For homing to cells and tissue, particularly suitable routes of administration include parenteral, either local or systemic. For example, particularly suitable routes of administration for homing to cells and tissues include intravenous, injection, infusion, intraarterial, intramuscular, intratumoral, peritumoral, intracerebral, intraventricular, intracerebroventricular, intracardiac, subcutaneous, intraosseous, intradermal, intrathecal, intraperitoneal, intravesical, intramedullar, intraocular, intracranial, intracisternal, epidural, peridural, and intravitreal. The disclosed compositions can be used in and with any other procedure. For example, the disclosed compositions can be administered as part of HIPEC therapy. In HIPEC a heated sterile solution containing a composition of interest is continuously circulated throughout the peritoneal cavity.

Pharmaceutical compositions can be manufactured by processes well known in the art, e.g., by means of conventional mixing, dissolving, granulating, dragee-making, levigating, emulsifying, encapsulating, entrapping or lyophilizing processes.

The compounds, compositions, and pharmaceutical compositions described herein can be administered to the subject in a number of ways depending on whether local or systemic treatment is desired, and on the area to be treated. Thus, for example, a compound or pharmaceutical composition described herein can be administered orally. Any suitable route of administration can be used for the disclosed compositions. Routes of administration can, for example, include topical, enteral, local, systemic, or parenteral. For example, administration can be intratumoral, peritumoral, epicutaneous, inhalational, enema, conjunctival, eye drops, ear drops, alveolar, nasal, intranasal, vaginal, intravaginal, transvaginal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc. Parenteral administration, if used, is generally characterized by injection. Injectables can be prepared in conventional forms, either as liquid solutions or suspensions, solid forms suitable for solution or suspension in liquid prior to injection, or as emulsions. Another approach for parenteral administration involves use of a slow release or sustained release system such that a constant dosage is maintained.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Toxicity of peptide, compounds, and compositions can be assessed for toxicity. Useful factors for assessing toxicity include body weight, serum cholesterol and triglyceride, and weight of liver and spleen. Liver and kidney functions can be monitored by blood tests. There have been no differences between LyP-1 and control groups after two months of continuous LyP-1 peptide administration, which indicates that LyP-1 treatment is non-toxic.

EXAMPLES

Example 1: Identification and Characterization of p32-Binding Compounds

Cell surface p32 is upregulated in tumors and atherosclerotic plaques and has been widely used as a receptor for systemic delivery of payloads. In this example, a p32-binding peptide was used in a fluorescence polarization-based high-throughput screening of a 50,000-compound chemical library to identify p32-binding compounds. The screen revealed a panel of compounds that bind p32 with low micromolar affinity. Among the hits identified in the screen, two compounds were shown to specifically bind to p32 in multiple assays. One of these compounds was chosen for an in vivo study. Nanoparticles surface-functionalized with this compound specifically adhered to surfaces coated with recombinant p32 and, when injected intravenously, homed to p32-expressing breast tumors in mice. This compound is an example of p32-targeted affinity ligands.

Targeted drug delivery into tumors remains a major goal in cancer drug development. The aim is to achieve effects similar to topical drug administration: high tumor accumulation and reduction of drug burden in non-target tissues. Drug selectivity can be improved by coupling a drug to a targeting moiety such as an antibody, aptamer, or peptide. Such synaphic (affinity-based) targeting relies on overexpression of specific receptor molecules in a systemically accessible compartment of the chosen target tissue (Ruoslahti et al., J. Cell Biol. 188 (2010) 759-768).

LyP-1 (CGNKRTRGC; SEQ ID NO: 1) is a widely used tumor-homing peptide originally identified by in vivo phage display (Laakkonen et al., Nat. Med. 8 (2002) 751-755). This peptide homes to tumors by binding to p32, a mitochondrial protein that is expressed on the surface of tumor endothelial cells (blood and lymphatic), tumor cells, and tumor macrophages (Laakkonen et al., Nat. Med. 8 (2002) 751-755; Fogal et al., Cancer Res. 68 (2008) 7210-7218). LyP-1 has been used for targeting of drugs and nanoparticles in breast cancer (Karmali et al., Nanomedicine-Nanotechnology Biology and Medicine. 5 (2009) 73-82; Park et al., Proc. Natl. Acad. Sci. U.S.A. 107 (2010) 981-986) and metastatic tumors in lymph nodes (Luo et al., Int. J. Pharm. 385 (2010) 150-156; Yan et al., J. Controlled Release. 157 (2012) 118-125). Interestingly, LyP-1 has a pro-apoptotic/cytotoxic activity on cultured malignant cells and it inhibits growth of certain breast tumor xenografts in vivo (Laakkonen et al., Proc. Natl. Acad. Sci. U.S.A. 101 (2004) 9381-9386). LyP-1 peptide has applications beyond tumor targeting—it also homes to atherosclerotic plaques, penetrates into their interior (Hamzah et al., Proc. Natl. Acad. Sci. U.S.A. 108 (2011) 7154-7159), and reduces aortic plaque in atherosclerotic mice in long-term administration of the peptide to the mice (U.S. Patent Application Publication No. 2013/0115167). LyP-1 thus serves as a prototype and model for other peptides that have similar properties and can produce similar effects.

Peptides are useful for targeted delivery of drugs in vivo, but ligand compounds also have advantages as an alternative. While peptides have to be administered parenterally and are susceptible to degradation by blood and tissue proteases (Pernot et al., Expert Opin. Drug Metab. Toxicol. 7 (2011) 793-802), compounds can generally be delivered orally and are generally more stable in blood than peptides. The stability of peptides can be improved without loss of activity by modifications such as introduction of reduced peptide bonds or N-methylated amino acids (Chatterjee et al., Angewandte Chemie-International Edition. 52 (2013) 254-269). A methylated version of the tumor-homing peptide CREKA circulates longer and homes to tumors more effectively than the unmodified peptide (Zanuy et al., J Phys Chem B. 113 (2009) 7879-7889; Agemy et al., Blood. 116 (2010) 2847-2856; Zanuy et al., J. Comput. Aided Mol. Des. 27 (2013) 31-43). There are also some low molecular weight affinity ligands, such as folate (Leamon et al., Drug Discov.

Today. 6 (2001) 44-51) and cobalamin (Waibel et al., Cancer Res. 68 (2008) 2904-2911) that are not peptides. Such alternatives to peptide ligands may have advantages such as greater stability and potential to be orally active (Friedman et al., Curr. Pharm. Des. 19 (2013) 6315-6329; Thomas et al., Expert Opinion on Drug Metabolism & Toxicology. 2 (2006) 591-608).

1. Materials and Methods i. Peptides and Proteins

Peptides were synthesized as previously described (Karmali et al., Nanomed.-Nanotechnol. Biol. Med., 10.1016/j.nano.2008.07.007). Briefly, peptides were synthesized using Fmoc/t-Bu chemistry on a microwave assisted automated peptide synthesizer (Liberty, CEM Corporation). Peptides were purified by HPLC using 0.1% TFA in acetonitrile-water mixtures to 90%-95% purity and validated by Q-TOF mass spectral analysis. Fluorescent peptides were synthesized by using 5(6)-carboxyfluorescein (FAM) with 6-aminohexanoic acid spacer to keep the fluorescent dye further away from the peptide. Proteins p32 and NRP-1 were obtained from Sanford-Burnham Medical Research Institute (SBMRI) Protein Production and Analysis Facility (La Jolla, Calif.).

ii. Phage Binding Assay

The binding of individual phage to p32 was verified using ELISA-type of phage binding assay. 96-well plates (Corning Life Sciences, Tewksbury, Mass., USA) were coated with 100 µL of 5 g/mL p32 in PBS at 4° C. overnight, washed 3 times with 200 µL of PBST (PBS+0.05% Tween-20), blocked with 200 µL of 0.5% bovine serum albumin (BSA) in PBST for 1 h at 37° C., and washed 3 times with PBST. Phages ($1.11*10^8$ pfu in 100 µL PBST) were added to p32-coated/BSA-blocked wells, the plate was incubated at 4° C. overnight, and washed 3 times with PBST. Subsequently, the plates were incubated with 100 µL in-house prepared polyclonal rabbit anti-T7 antibody diluted 1:1000 in PBST for 1 h at 4° C., and washed 3 times with washing buffer. Horseradish peroxidase (HRP)-labeled anti-rabbit IgG (Sigma-Aldrich) was diluted 1:1000 in PBS, and 100 µL was added to the wells, followed by 1 h incubation at 4° C. and washing 3 times. Next, 100 µL of OPD silver and gold substrate (Sigma-Aldrich) was added to the wells and incubated at room temperature until visible color was observed (<30 min). The reaction was stopped by adding 50 µL of 1M $H_2SO_4$, and the plate was read at 492 nm (Varioskan Flash, Thermo Scientific, Waltham, Mass., USA).

iii. Fluorescence Polarization Assay

Figure 5:
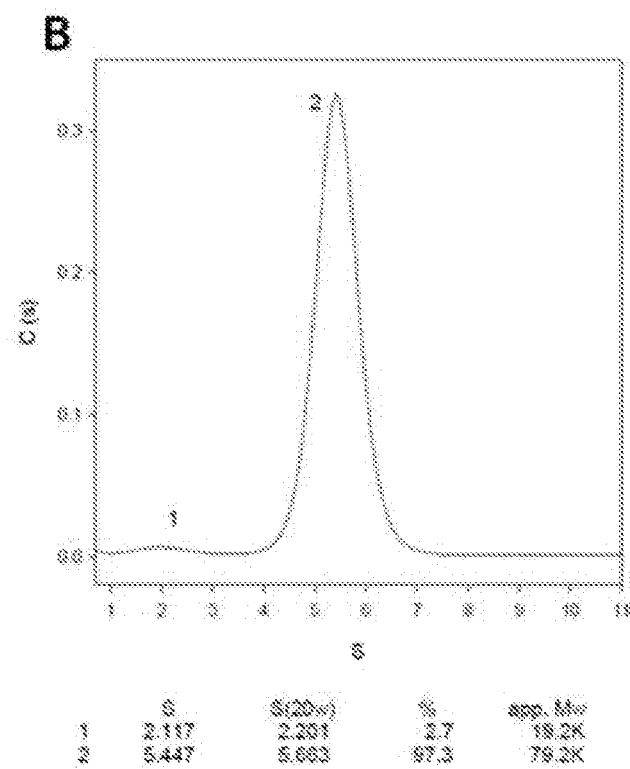
FIG. 5 is a graph of sedimentation velocity of oligomerized p32 protein. Sedimentation velocity assay that allows determination of the multimeric state of proteins demonstrated that similarly to the native p32 protein, recombinant p32 is present predominantly (>97%) as a trimer with sedimentation coefficient of 5.447 and apparent molecular weight of complex 79.2 kDa.

Fluorescence polarization (FP)-based assay was used for solution-based screening of compound libraries for p32 binding compounds. FP assays have been used in high-throughput screening in drug discovery process since mid-1990's (Owicki, Journal of Biomolecular Screening, 10.1177/108705710000500501). In FP assay, peptide conjugated with a fluorescent label (fluorescein-AM, FAM) is excited with polarized light. Free peptide in solution rotates fast and the polarization of emitted light differs from excitation plane, which is observed as low polarization. 6×-His-Tagged p32 was expressed in Rosetta-gami-2 cells (Novagen). The protein was purified by IMAC using HIS-select resin (Sigma) with an imidizole gradient from 20-300 mM and eluted fractions were analyzed on analytical SDS-PAGE. When peptide binds to larger molecules, such as receptor protein, the rotation decreases significantly and emitted light becomes highly polarized (FIG. 5). Fluorescence polarization is given as milli-polarization (mP) value, which is obtained from equation (1):

$$mP=1000*(S-P)/(S+P), \quad (Eq. 1)$$

where S is fluorescence parallel to excitation plane and P is fluorescence perpendicular to excitation plane (Lea and Simeonov, Expert Opinion on Drug Discovery, 10.1517/17460441.2011.537322).

The assay was initially set up in 20 µl well volume in 384 well plate (Corning Life Sciences), and measurements were carried out using PheraStar FS plate reader (BMG LABTECH, Ortenberg, Germany) in quadruplicate. Peptide and protein stock solutions were diluted to desired concentration with assay buffer (50 mM BIS-TRIS pH 7.4, 0.05% Tween20, 1 mM DTT). FAM-labeled peptides were protected from light during the experiment to avoid photobleaching. Optimal concentration of fluorescein (FAM) labeled-peptides for the assay was determined by measuring the limit of detection (LOD), signal-to-background ratio (S/B), and stability of mP value over series of peptide concentrations. In the binding assay, the concentration of FAM-peptide was kept constant, and the FP was measured over the range of target protein concentrations. The peptide dissociation constant ($K_D$) was obtained by fitting the binding curve into Michaelis-Menten kinetics in GraphPad Prism-software (GraphPad Software, Inc., CA, USA). The specificity of the binding assay was verified by the displacement assay, in which FAM-labeled peptide was competed off from the target protein by titrating the unlabeled peptides up to 100 µM. Specificity of the peptide was further verified by testing the peptide binding to b1b2 domain of NRP-1 (Vander Kooi et al., Proc. Natl. Acad. Sci. U.S.A., 10.1073/pnas.0700043104; Teesalu et al., Proc Natl Acad Sci USA. 2009; 106(38): 16157-16162).

iv. High-Throughput Screening

Fluorescence polarization assay was transferred to 1536-well plate format using volumes and concentrations listed in Table 1.

TABLE 1

Volumes and final concentrations of the reagents used in high-throughput fluorescence polarization screening of chemical compound library.

| | Volume | Final concentration |
|---|---|---|
| FAM-peptide | 1.5 µL | 10 nM |
| p32 protein | 1.5 µL | 6 µM |
| Library compounds | 37.5 nL | 25 µM |

The detailed screening protocol including negative and positive controls is as follows.

Screening Protocol and Plate Layout

FAM-TT-1 and p32 solutions are prepared just before experiment, and stored on ice during the screen; the peptide is shielded from light.

1. Dispense 37.5 nL DMSO into columns 1-4 and 45-48 of assay plate (Corning #3724)
2. Dispense 1.5 µL of assay buffer (50 mM BIS-TRIS pH 7.4, 0.05% Tween 20, 1 mM DTT) into columns 1-4
3. Dispense 1.5 µL of p32 protein (12 µM) into columns 5-48
4. Dispense 37.5 nL of compounds (2 mM) into columns 5-44
5. Spin plate
6. Incubate 20 min
7. Dispense 1.5 µL FAM-TT-1 peptide (20 nM) into all columns 8. Shake plate and spin plate
9. Incubate 25 min
10. Read plate on PheraStar FS
Assay Plate Diagram

| Columns 1 to 4 | Columns 5 to 44 | Columns 45 to 48 |
| --- | --- | --- |
| DMSO + Buffer + FAM-TT1 | p32 + Compounds + FAM-TT1 | DMSO + p32 + FAM-TT1 |

Chemical library of ~50,000 compounds from ChemBridge (San Diego, Calif.) was screened in High-Throughput Screening Facility at Conrad Prebys Center for Chemical Genomics (Sanford-Burnham Medical Research Institute, La Jolla, Calif.). The screening was performed using fully integrated automatic system using Stäubli TX90XL robotic arm (Pfaffikon, Swizerland), Labcyte Echo 555 acoustic dispenser (Sunnyvale, Calif.), Multidrop Combi reagent dispenser (Thermo Scientific, Waltham, Mass.), HighRes Pintool transfer device with ultrasonic bath (HighRes Biosolutions, Woburn, Mass.), Velocity 11 VSpin centrifuge (Agilent Technologies, Santa Clara, Calif.), and PheraStar FS plate reader (BMG LABTECH). The binding of at 25 μM library compounds to p32 protein was studied by their ability to displace FAM-TT1 from p32 protein. Peptide and protein were diluted immediately prior to screening, kept on ice during screening, and FAM-peptide was protected from light throughout the experiment.

v. Evaluation of Concentration-Dependence and Specificity of the Hit Compounds

Results of the high-throughput screen were confirmed in dose response tests. 8.25 μM to 100 μM dilutions of the compounds that displaced FAM-peptide from p32 were used in competition with FAM-peptide as described in previous section. Specificity of the hit compounds was verified by examining their binding to a different protein, b1b2 domain of NRP-1 (Vander Kooi et al., Proc. Natl. Acad. Sci. U.S.A, 10.1073/pnas.0700043104). Experimental method for NRP-1 b1b2 was developed and validated similarly to p32, using FAM-RPARPAR peptide as a known peptide ligand for NRP-1. The displacement of FAM-RPARPAR from NRP-1 protein by the hit compounds was studied in 384-well format, as described above.

vi. Phage Binding and Inhibition Assay

The ability to inhibit TT1-phage binding to p32 protein was used as a secondary assay to verify the hit compounds. The competition assay was based on the phage binding assay described above with minor modifications. ELISA plates were coated with 2.5 μg/mL p32, incubated with phages (1.11*$10^8$ pfu in 100 μL PBST) and 100 μM hit compounds at 4° C. overnight, and followed by antibody incubation and chromogenic reaction. Negative controls included DMSO at concentration it was used to dissolve the hit compounds.

vii. NMR Samples and Data Acquisition

All the NMR experiments were carried out on a Bruker Avance 700 spectrometer equipped with a TCI cryoprobe at T=293 K. For structure determinations, the peptide concentration was 100 μM in the NMR buffer in presence of 150 μM of $ZnCl_2$. One-dimensional (1D) 1H spectra were acquired with a spectral width of 8417.51 Hz, relaxation delay 1.0 s, 8 k data points for acquisition and 16 k for transformation.

viii. Silver Nanoparticle Functionalization with #4014008 and Binding Silver Nanoparticles to Immobilized p32

Silver nanoparticles (AgNPs) with CF555 dye-labeled neutravidin coatings (555-Ag-NA) were prepared as described in Pang et al. 2014, with the difference that AgNPs were synthesized by citrate reduction (Lee and Meisel, J. Phys. Chem., 10.1021/j100214a025) with a core size of ~30 nm Ag rather than polyvinylpyrrolidone reduction. An extinction of $1\times10^{10}$ M-1 cm-1 at the 405 nm Ag plasmon peak was used to quantify the concentration of AgNPs. A biotinylated form of the #4014008 compound was prepared by reacting amine-reactive sulfo-NHS-LC-Biotin (Pierce Cat#21335) with six-fold molar excess of the free amine containing #4014008 in DMSO. The unpurified biotinylated product was loaded into the 555-Ag-NA, washed by centrifugation and brought up in PBS containing 0.05% Tween 20 (PBST). The resulting #4014008-555-Ag-NA (401-Ag for short) was added to wells having pre-immobilized protein, either p32 or hexahistidine-tagged control protein N3A (His-control). Wells were prepared by incubating 96-well high-binding titer plates (ELISA) with 5 μg/mL protein in PBS overnight at 4° C. followed by blocking with 1% bovine serum albumin in PBS for 1 h at room temperature, and washing three times with PBST. After incubation with nanoparticles at room temperature for 3 h, the wells were washed 3× with PBST and imaged by epifluorescence microscopy with a 20× objective (Leica DMIRE2). The number of particles per field of view was then thresholded to remove the uniform background fluorescence and the number of nanoparticle dots was quantified by ImageJ (command: Analyze Particles).

ix. Preparation of Iron Oxide Nanoworms.

NWs were prepared as previously described (Agemy et al., Proc. Natl. Acad. Sci. U.S.A, 10.1073/pnas.1114518108). Aminated NWs were pegylated with maleimide-SK-PEG-NHS (JenKem Technology). #4014008 compound was conjugated to the nanoparticles through a thioether bond. The compound was modified to have a fluorescein and a cysteine thiol to aid the Michael addition between the compound and the maleimide-functionalized particles.

x. In Vivo Homing of Iron Oxide Nanoworms.

Animal experimentation was performed according to the procedures approved by the Animal Research Committee at the Sanford-Burnham Medical Research Institute, San Diego. To generate breast tumors BALB/c nude mice were orthotopically injected with MCF10CA1a into the mammary fat pad with $2\times10^6$ cells suspended in 100 μl of PBS. Mice bearing orthotopic breast tumors were used for homing experiments when the tumors reached 0.5-1 cm in size. FAM labeled #4014008-NWs were injected into the tail vein (7.5 mg of iron per kilogram of body weight), the animals were euthanized 5-6 hours after the injection by cardiac perfusion with PBS under anesthesia, and organs were dissected and analyzed for particle homing.

xi. Immunofluorescence and Immunohistochemistry.

Tissues from mice injected with nanoparticles were fixed in 4% paraformaldehyde overnight at 4° C., cryoprotected in 30% sucrose overnight, and frozen in optimal cutting temperature (OCT) embedding medium.

For immunostaining, 7 m thick tissue sections were first incubated for 1 hour at room temperature with 10% serum from the species in which the secondary antibody was generated, followed by incubation with the primary antibody overnight at 4° C. The following antibodies were used: rat monoclonal anti-mouse CD31 (1:50; BD Pharmingen) and rabbit p32 (1:250; Millipore). The primary antibodies were detected with Alexa 594 goat anti-rat and 594 goat anti-rabbit secondary antibodies (1:1000; Molecular Probes). Each staining experiment included sections stained only with secondary antibodies as negative controls. Nuclei were counterstained with DAPI diamidino-2-phenylindole (5 mg/ml; Molecular Probes). The sections were mounted in gel/mount mounting medium (Biomeda) and viewed under a LSM 710 NLO Multiphoton Laser Point Scanning Confocal Microscope (Zeiss).

2. Results and Discussion

Figure 1C:
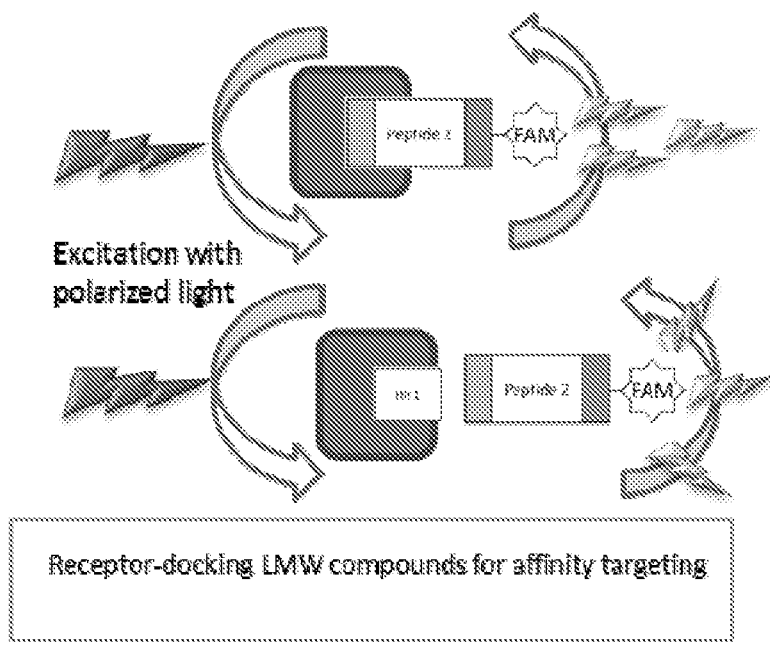

A fluorescence polarization (FP)-based assay was used to identify low molecular weight mimics of p32-binding homing peptides. Fluorescence polarization (FP)-based assays are solution-based, homogeneous techniques requiring no immobilization or separation of reaction components (Owicki et al., Journal of Biomolecular Screening. 5 (2000) 297-306; Lea et al., Expert Opinion on Drug Discovery. 6 (2011) 17-32) (FIG. 1C). Recombinant 6x-His-tagged p32 was used as a target. According to sedimentation velocity analysis the recombinant 6x-His-tagged p32 was in the expected trimeric form (Jha et al., European Journal of Biochemistry. 269 (2002) 298-306). The CKRGARSTC peptide (designated TT1), which showed the strongest binding to p32 among the screened peptides (Paasonen et al., Chembiochem. 2016 Apr. 11; 17(7):570-575), was chosen for the FP-based screening of compound libraries.

Figure 2A:
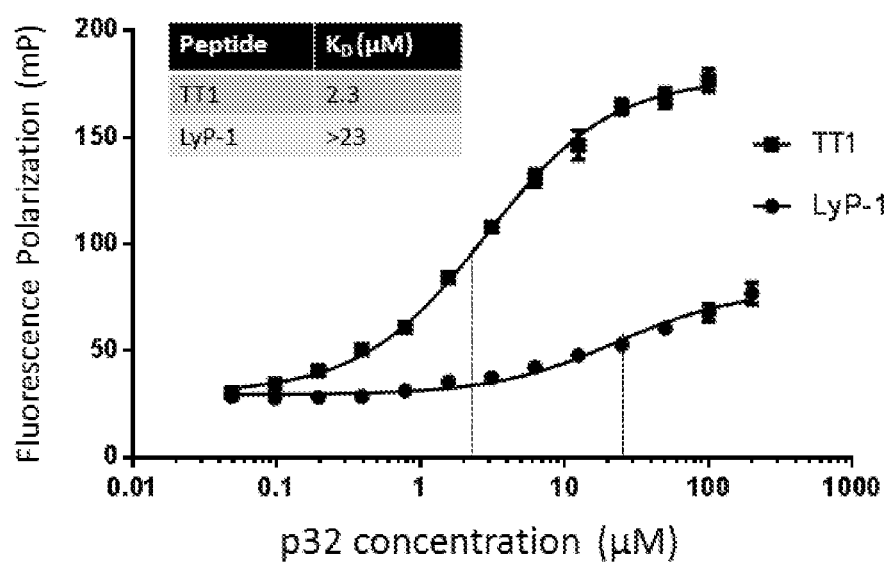
FIGS. 2A-2D are graphs showing FP- and phage binding-based validation of p32 binding peptides and hit compounds. (A) Fluorescence polarization (FP) measurement of binding affinity of FAM-LyP-1 and FAM-TT1 peptides to p32 protein and dissociation constants ($K_D$) based on binding curves fitted on Michaelis-Menten kinetics. Measurements were performed with PheraStar FS plate reader (BMG Labtech, Ortenberg, Germany) on 384-well plate. (B) Affinity of the 7 hit compounds in dose-dependent (8.25 μM to 100 μM) inhibition of FAM-TT1 binding to p32 in FP assay. (C) Assessment of hit compound binding to a non-target secondary protein, NRP-1, to determine the specificity of the hit compounds in FP assay. A known NRP-1 binding peptide, RPARPAR (SEQ ID NO:18), was used as a control. (D) Effect of the hit compounds on the TT1 phage binding to p32 protein. TT1 phage binding to p32 in the presence of 100 μM hit compounds was determined in ELISA-type of binding assay. Each data point presents average±S.D., n=4.
Figure 6:
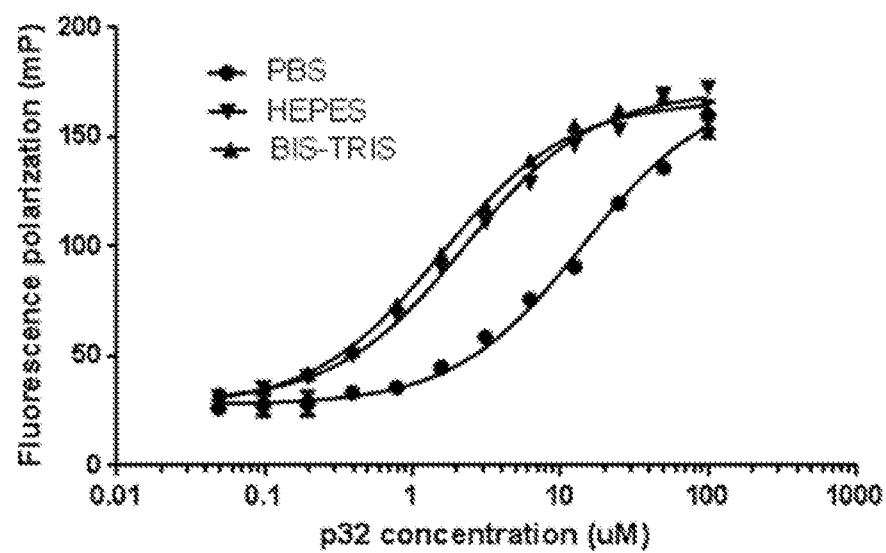
FIG. 6 is a graph showing the effect of buffer solution on interaction of TT1 and p32. The binding affinity of FAM-labeled TT1 to p32 was studied in different assay buffers: in PBS, HEPES, and BIS-TRIS, respectively. The binding was measured by fluorescence polarization (FP) and observed as increased FP value. Binding constants ($K_D$) were calculated by fitting the binding curves into Michaelis-Menten kinetics. Each data point presents average±S.D., n=4-6.

The composition of binding buffer had profound influence on TT1-p32 binding; the $K_d$ in phosphate buffered saline (PBS) was considerably higher (14 μM) than in BIS-TRIS or HEPES buffers (2.3 μM and 1.6 μM, respectively), suggesting that the higher salt concentration in PBS decreases peptide binding (FIG. 2A, FIG. 6). TT1 binds to p32 even in its linear form, which can be generated in the reducing buffer used in the screening (Paasonen et al., Chembiochem. 2016 Apr. 11; 17(7):570-575).

Figure 7:
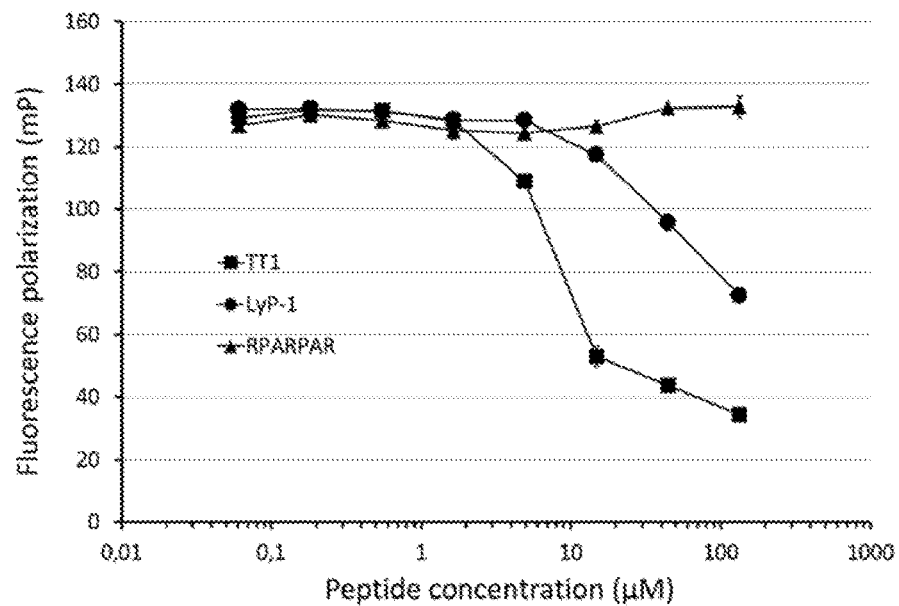
FIG. 7 is a graph showing specificity of the FAM-TT1 binding to p32. Dislocation of FAM-TT1 from p32 with unlabeled peptides was studied to check the specificity of TT1-p32 interaction. FAM-TT1 and p32 were incubated together with unlabeled TT1 and LyP-1, and unlabeled RPARPAR peptide, respectively. Unlabeled TT1 dislocated FAM-TT1 from p32. Known p32 binding peptide, LyP-1, dislocated FAM-TT1 at high concentrations. RPARPAR peptide did not dislocate FAM-TT1, suggesting specific binding of FAM-TT1 to p32. Each data point presents average±S.D., n=4-6.
Figure 8:
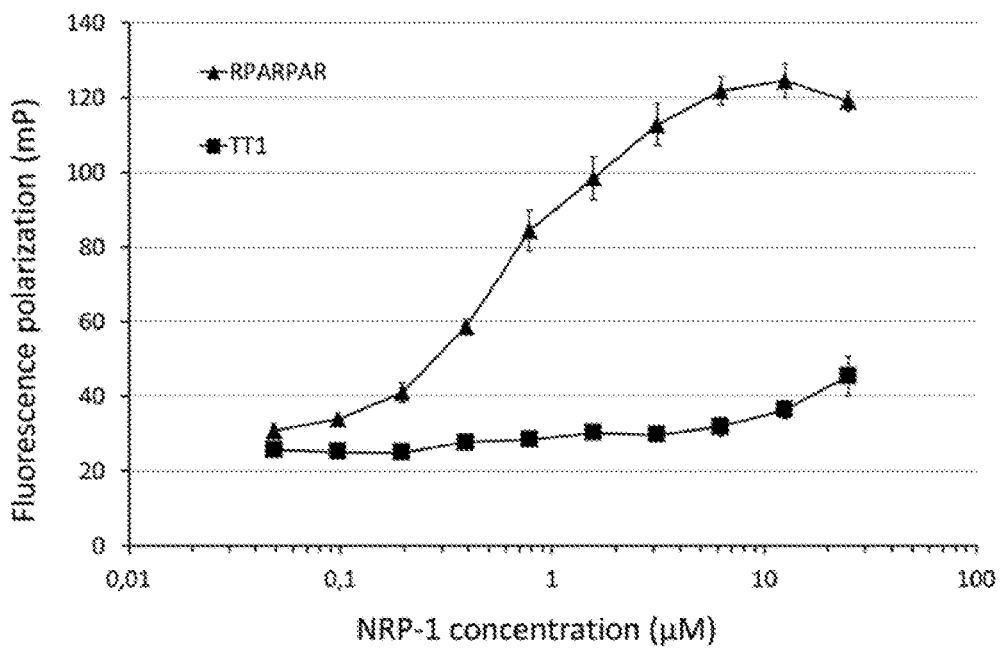
FIG. 8 is a graph showing specificity of TT1 binding. Specificity of TT1 was further evaluated by measuring the binding of FAM-TT1 to recombinant non-target protein, b1b2 domain of neuropilin-1 (NRP-1). The binding was studied by fluorescence polarization. FAM-TT1 did not show binding to NRP-1, where known NRP-1 binding peptide, RPARPAR, showed strong affinity to NRP-1. Each data point presents average±S.D., n=4-6.

FAM-TT1 binding to p32 was inhibited in a dose-dependent manner by unlabeled TT1 and LyP-1, but not by the RPARPAR peptide. RPARPAR binds to NRP-1, a receptor with specificity somewhat similar to that of p32, as both proteins favor positively charged ligands (Teesalu et al., Proc. Natl. Acad. Sci. U.S.A. 106 (2009) 16157-16162) (FIG. 7). The specificity of the TT1-p32 interaction was further demonstrated by lack of binding of TT1 to b1b2 domain of NRP-1 (FIG. 8). Thus, TT1 interaction with p32 is specific, and the mutual inhibition of the binding of one peptide by the other indicates that TT1 and LyP-1 bind to the same site on the p32 protein.

Figure 2B:
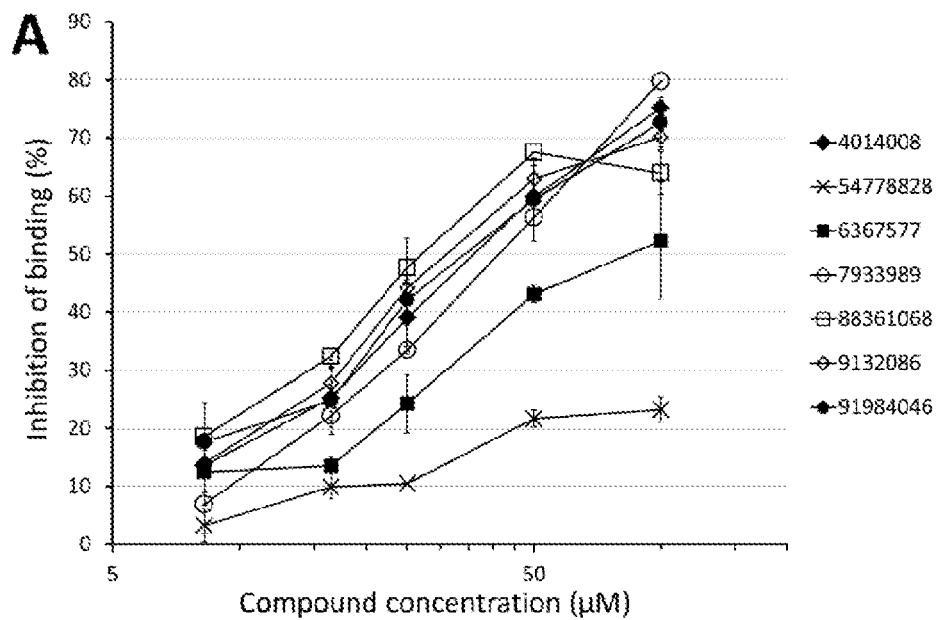

After establishing and validating the FP assay, a library of 50,000 compounds (Sanford-Burnham Medical Research Institute, San Diego, USA) was screened in 1536-well format for molecules capable of inhibiting the interaction of TT1 peptide with p32. The compounds in this library have been selected to provide 2D diversity for extensive pharmacophore coverage for primary screening and to offer the most attractive features found in lead- and drug-like compounds. The screening led to identification of 7 hit compounds (Table 2) that at 100 μM concentration caused greater than 20% inhibition of the TT1-p32 interaction. Six out of the 7 compounds showed dose-dependent inhibition of FAM-TT1 binding to p32 (FIG. 2B). At the highest concentration used (100 μM), the inhibition ranged from 50 to 80%. Compound #54778828 was only marginally active, and was not studied further. Compound #6367577 was less effective than the other active compounds.

TABLE 2

Hit Compounds

| Inhibition % | Compound ID | Name | MW | LogP | PSA | H Bond Donor | H Bond Acceptor | Rotatable Bond |
|---|---|---|---|---|---|---|---|---|
| 40.5 | 7933989 | (5,5-dimethyl-4,5-dihydro-1,3-thiazol-2-yl){2-[(5,5-dimethyl-4,5-dihydro-1,3- | 286 | 0.97 | 48.8 | 2 | 2 | 5 |
| 39.5 | 6367577 | 7-hydroxy-8-methyl-4-(trifluoromethyl)-2H-chromen-2-one | 244 | 3.02 | 50.4 | 1 | 3 | 0 |
| 30.8 | 88361068 | 1-{3-amino-6-[4-methyl-2-(1H-pyrazol-1-yl)phenyl]pryazin-2-yl}pyrrolidin-3- | 336 | 2.6 | 93.1 | 2 | 4 | 3 |
| 29.9 | 4014008 | N-(3-methylpyridin-4-yl)ethane-1,2-diamine | 151 | 0.93 | 50.9 | 2 | 2 | 3 |
| 29.4 | 54778828 | 4-{3-[1-(3-pyridinylmethyl)-4-piperidinyl]-1-pyrrolidinyl}-2-pyrimidinami | 338 | 2.08 | 71.2 | 1 | 4 | 4 |
| 22.5 | 91984046 | 3-(3,4-difluorophenyl)-5-methyl-4,5,6,7-tetrahydroisoxazolo[4,5- | 250 | 2.14 | 29.3 | 0 | 3 | 1 |
| 20.7 | 9132086 | 2-methyl-6-(2-thienyl)-6,7-dihydro[1,2,4]triazolo[5,1-b]quinazolin-8(5H)-one | 284 | 1.89 | 60.2 | 0 | 4 | 1 |

Compound #7933989

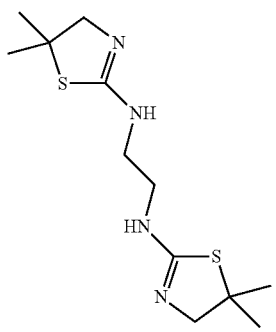

Compound #6367577

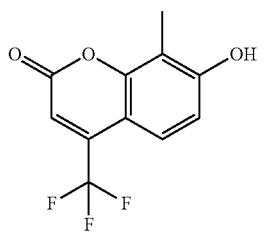

Compound #88361068

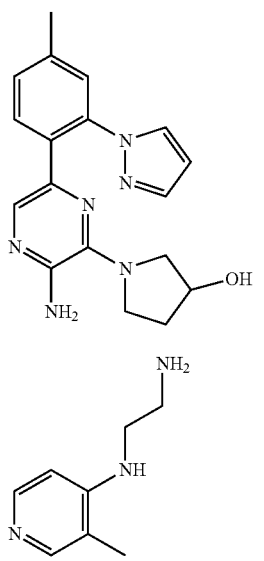

Compound #4014008

Compound #54778828

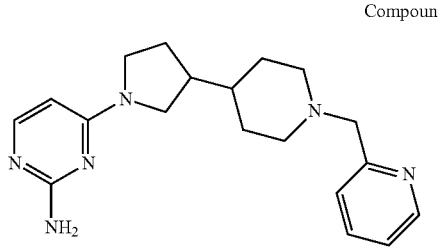

Compound #91984046

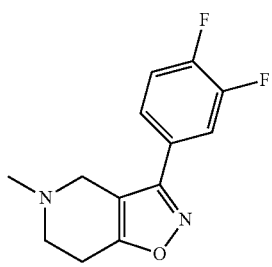

Compound #9132086

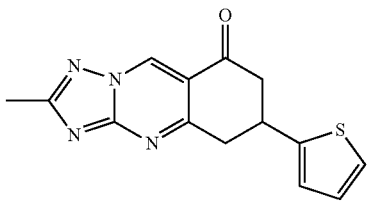

Figure 2C:
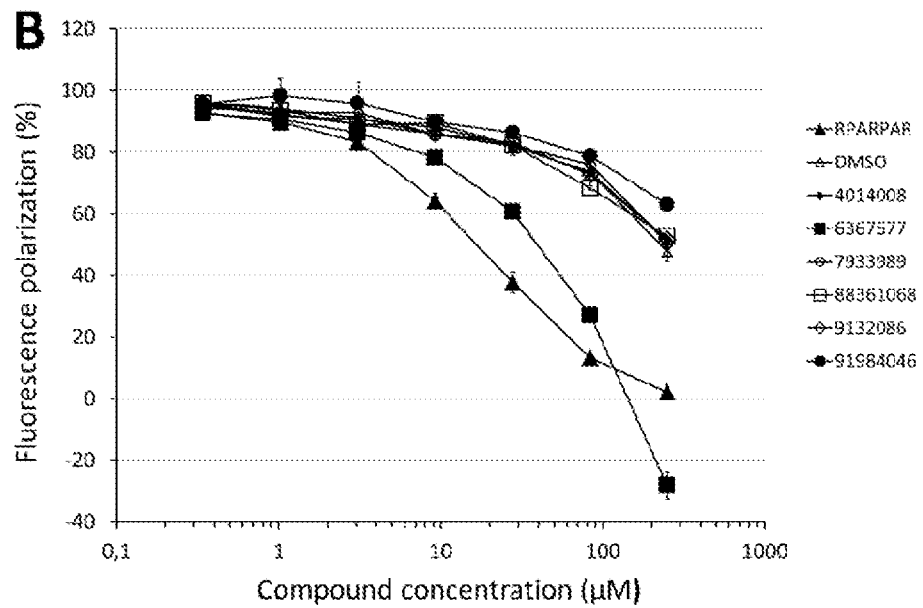

An assay based on the binding of the RPARPAR peptide to NRP-1 was then used to study the effect of the 6 active compounds on a different, but somewhat similar peptide-protein interaction. Compounds #4014008, #9132086, #88361068, and #7933989 had no effect in this assay. The polarization decrease seen at the highest compound concentrations was no greater than that caused by the DMSO solvent (FIG. 2C). The FP level in the presence of compound #6367577 at the highest concentration had a negative value, indicating that the compound itself is a fluorophore. Therefore, compound #6367577 was excluded from further studies.

Figure 2D:
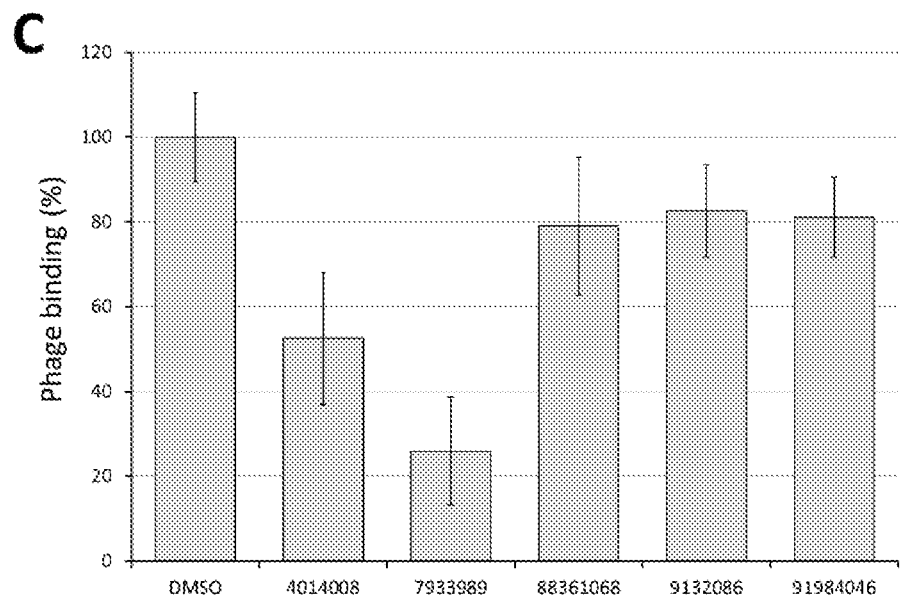
Figure 3A:
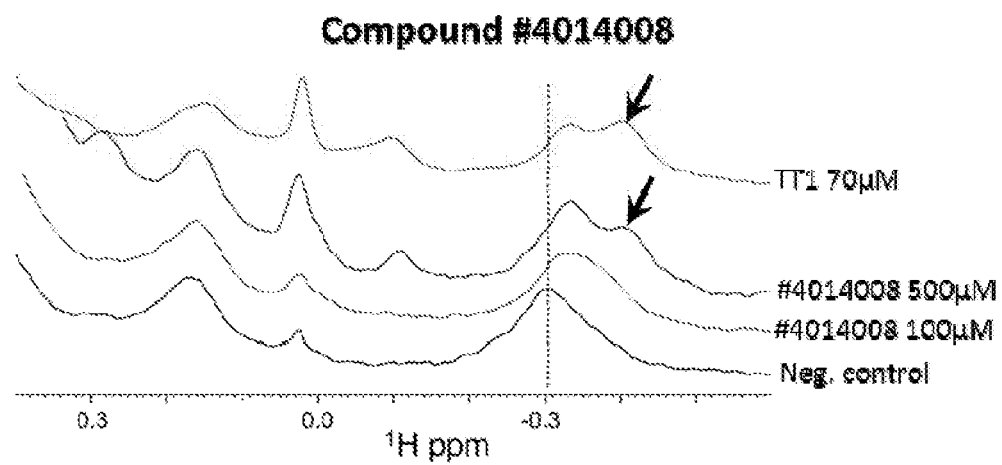
FIGS. 3A and 3B are graphs showing NMR based evaluation of binding of compounds 4014008 and 7933989 to P32 protein. The ID $^1$H-aliph spectra of 5 μM P32 in the absence (bottom) and presence of compounds #4014008 (A) and #7933989 (B) at 100 μM (second from bottom) and 500 μM (second from top) were collected. As a control, the spectrum of p32 in the presence of the known peptide binder, TT1 at 70 μM, was also collected (top). In presence of both compounds there is a shift in the peak at around −0.3 ppm (dashed line) and the concomitant appearance of a shoulder peak (indicated by arrows) similar to what is observed in presence of the reference peptide TT1.
Figure 3B:
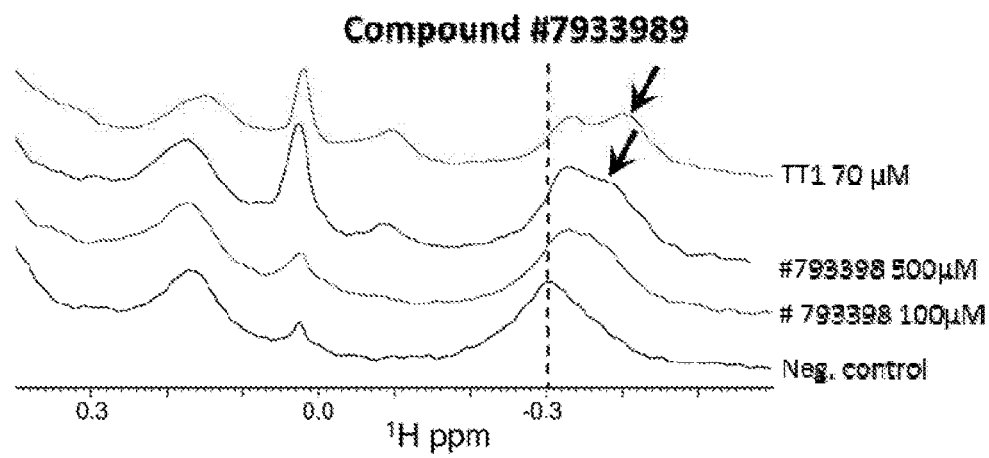

Inhibition of TT1 phage binding to p32 was used to confirm the activity of the remaining 5 compounds. At 100 μM, compounds #4014008 and #7933989 inhibited TT1 phage binding to p32 by 50% and 75%, respectively (FIG. 2D). This agreed with the results of the FP assay measuring TT1 binding to p32 (FIG. 3A), where #4014008 showed 75% and #7933989 80% inhibition. Compounds #88361068, #9132086, and #91984046 inhibited TT1 phage binding to p32 only by 20%, whereas in the FP assay had given 65% to 75% inhibition (FIG. 2A). Peptides are displayed on the T7 bacteriophage at about 200 copies per particle (Teesalu et al., Methods Enzymol. 503 (2012) 35-56) and the multivalent phage binding to immobilized p32 is likely to be less susceptible to inhibition by a free competitor than the TT1 binding to p32. Thus, the affinity of these latter 3 compounds for p32 may be low. NMR analysis was used to further confirm interaction of p32 with the most active 2 compounds, #4014008 and #7933989. The TT1 peptide was used as a control. Under the same experimental conditions, the TT1 peptide caused significant perturbations in the 1D $^1$H-aliphatic spectra (Barile et al., Chem. Rev. 114 (2014) 4749-4763) with 5 μM p32 concentration. Both compounds #4014008 and #7933989 caused similar perturbations indicating binding to p32 similar to that of TT1 (FIG. 3).

Figure 4A:
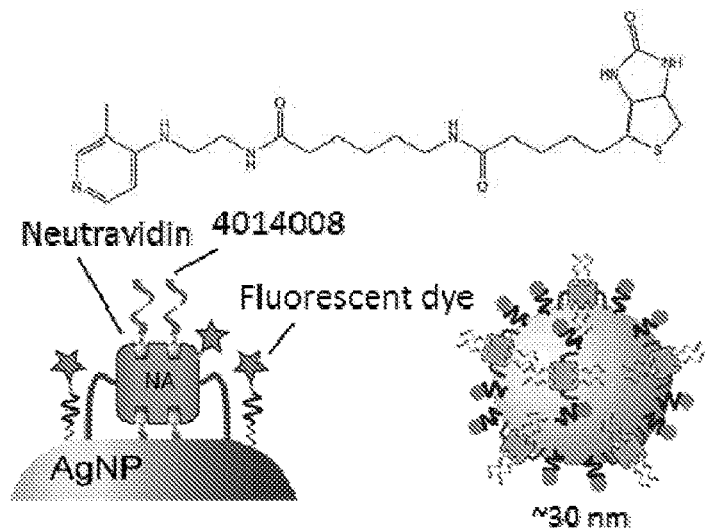
FIGS. 4A, 4B, and 4C show nanoparticles functionalized with #4014008 bind to p32 protein. (A) Diagram of the compound coupled to fluorescent silver nanoparticles. (B) The coupled compound showed specific binding toward plate well bound p32 protein, relative to wells having a non-target control protein N3A. Increased concentration of silver nanoparticles caused a dose-dependent increase in fluorescent signal due to nanoparticle binding to the surface of the well. (C) Diagram and structure of FAM-#4014008-NW.
Figure 4B:
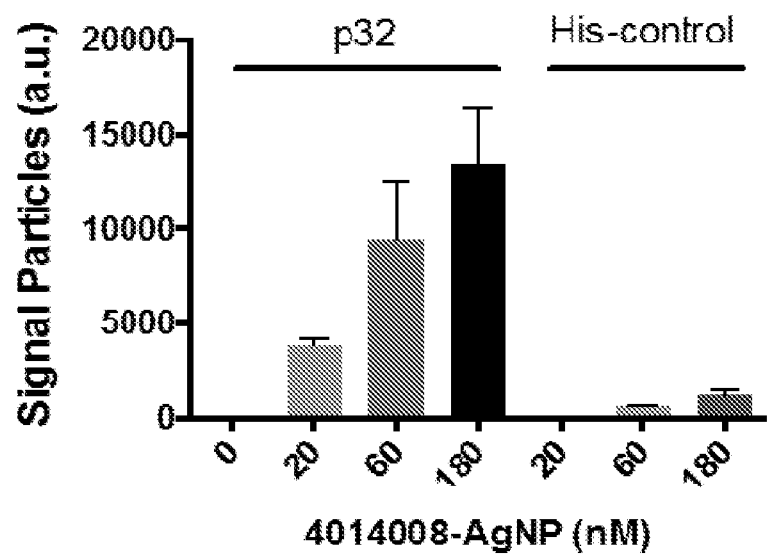

The data described above indicate that compounds #4014008 and #7933989 interact specifically with the homing peptide-binding site on the p32 protein and represent affinity ligands for p32-directed payload delivery. Compound #401008 was chosen for further studies. #4014008 is also appealing as lead molecule; its structure lends itself to SAR studies and an amine group in the compound provides a readily available coupling group. Silver nanoparticles (AgNP) coated with neutravidin (Braun et al., Nature Materials. 13 (2014) 904-911) and functionalized with biotinylated compound #4014008 (FIG. 4A) showed specific in vitro binding to immobilized recombinant p32 protein (FIG. 4B). In contrast, the #4014008AgNPs showed only background binding to a non-target recombinant protein.

Figure 4C:
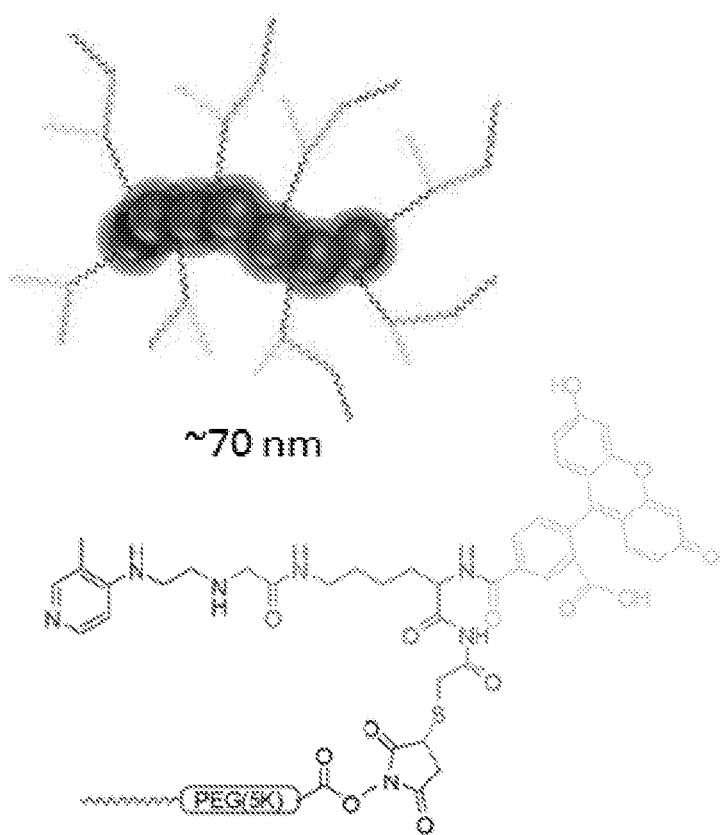

Iron oxide nanoparticles, dubbed "nanoworms" (NWs), were used to evaluate #4014008 as an in vivo targeting ligand (FIG. 4C). These paramagnetic nanoparticles are PEGylated to achieve long blood half-life, and have more effective targeting properties than spherical nanoparticles because of their elongated shape (Agemy et al., Blood. 116 (2010) 2847-2856; Park et al., Small. 5 (2009) 694-700). MCF10Ca1A breast tumor cells express cell surface p32 in vitro and p32-binding peptides home to orthotopic MCF10Ca1A xenograft tumors (Agemy et al., Molecular Therapy. 21 (2013) 2195-2204). NWs functionalized with #4014008 showed robust homing to the blood vessels in MCF10Ca1A tumors. The pattern was similar to what was seen with TT1-NWs. Specifically, confocal imaging of tissue sections of MCF10Ca1A breast tumors from mice injected with FAM-TT1-IONW or with FAM-##4014008-IONW were produced. FAM labeled TT1-NWs were injected into the tail vein (7.5 mg of iron per kilogram of body weight) of tumor-bearing mice. The mice were euthanized 5-6 hours after the injection by cardiac perfusion with PBS under anesthesia, and organs were dissected and analyzed for particle homing.

Among normal tissues, some #4014008-NW uptake was seen in organs of the reticuloendothelial system (liver and spleen), which non-specifically scavenge nanoparticles, and in the lungs, but not in other organs studied. Confocal imaging of tissue sections of control organs from MCF10Ca1A breast tumor-bearing mice injected with FAM-##4014008-IONW was performed. Some nanoparticle uptake was seen in the liver and spleen. MCF10Ca1A breast tumor xenografts express abundant p32 in blood vessels, and p32 immunoreactivity showed overlap with NW signal. These studies show that functionalization with #4014008 renders nanoparticles selective for p32 binding in vitro and in vivo.

The #401008 compound reproduced the critical properties of the peptides: p32 binding, homing to tumors, and ability to deliver payload to tumors. The demonstration that the p32 receptor can be accessed with a drug-like compound has important implications. First, it shows that the functionality of a peptide used for tumor delivery can be reproduced in small molecule compounds. This can provide the homing functionality of the peptide in a small molecule compound, which has the features of a small molecule compound and lacks some of the challenges of a peptide therapeutic. For example, the sensitivity of peptides to proteolytic degradation is avoided with a small molecule compound. Second, small molecule homing compounds can be used to make synaphically targeted drugs that are orally active. Lastly, the compounds identified through the peptide screening can have useful biological activities beyond homing. Peptides that bind to proteins generally bind at binding pockets for compounds that modify the activity of the protein (Ruoslahti et al., Adv Mater. 24 (2012) 3747-3756). As such, they are likely to have inherent biological activities. Two examples are the integrin-binding RGD peptides, probably the most frequently used peptide motif in the design of tumor-targeting drugs and nanoparticles (Ruoslahti et al., Adv Mater. 24 (2012) 3747-3756) and the p32-binding peptide LyP-1 (Laakkonen et al., Proc. Natl. Acad. Sci. U.S.A. 101 (2004) 9381-9386). RGD peptides inhibit integrin activity and drugs based on RGD are in the clinic and in clinical trials. LyP-1 inhibits tumor growth (Laakkonen et al., Proc. Natl. Acad. Sci. U.S.A. 101 (2004) 9381-9386) and atherosclerotic plaque development (U.S. Patent Application Publication No. 2013/0115167). The chemical compounds modeled after the p32-binding peptides can have similar capabilities.

Abbreviations Used

AgNP Silver nanoparticles
BSA Bovine serum albumin
DAPI Diamidino-2-phenylindole
DTT Dithiothreitol
ELISA Enzyme-linked immunosorbent assay
FAM 5(6)-carboxyfluorescein
FP Fluorescence polarization
HPLC High pressure liquid chromatography
$K_d$ Dissociation constant
NMR Nuclear magnetic resonance
NRP-1 Neuropilin-1 (NRP-1)
NW Iron oxide nanoworms
PBS Phosphate buffered saline
PBST Phosphate buffered saline with 10% Tween20
PEG Polyethylene glycol
Q-TOF Quadrupole time-of-flight
TFA Trifluoro acetic acid Example 2: Analysis of p32-Binding Peptides and Compounds While the original results were obtained with the LyP-1 peptide, the peptide TT1 binds to p32 with a higher affinity than LyP-1 (2.3 µM vs 23 µM) and homes to plaques more effectively than LyP-1. TT1 was identified by screening a phage library for peptides that bind to purified p32 protein (Paasonen et al., Chembiochem. 2016 Apr. 11; 17(7):570-575). Like LyP-1, TT1 is a 9-amino acid cyclic peptide with a cryptic CendR sequence for target tissue penetration (a cryptic CendR sequence is one that is not present at a free C-terminal end of the peptide). LyP-1 and TT1 inhibit one another's binding to p32, indicating that the two peptides bind to the same site on p32. Briefly, ApoE null mice that had been kept on a high-fat diet were intravenously injected with 100 µg of the FAM-labeled peptides. One hour later, the mice were perfused through the heart under anesthesia, and tissues were collected. Accumulation of FAM-labeled peptides was visualized with UV excitation. Atherosclerotic aortas were sectioned at the aortic root level, and examined by confocal microscopy. FAM-LyP-1 and FAM-TT1 signal was seen inside plaques, whereas a control peptide does not accumulate in the plaques. CD31 staining was used to visualize the endothelium over the plaque. This shows that TT1-peptide homes to and penetrates into plaque tissue as well as or better than LyP-1.

Figure 10:
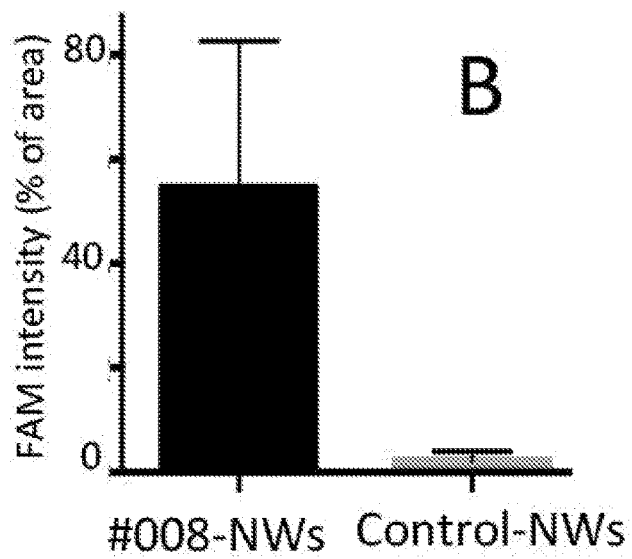
FIG. 10 is a graph of nanoparticles functionalized with compound #008 homing to tumors and atherosclerotic plaques. Orthotopic MCF10Ca1Abreast tumors from mice injected with iron oxide nanowires (NWs) (7.5 mg/kg of Fe) coated with FAM-#008 or with an inert peptide (control). The NWs were allowed to circulate for 5 hours, the mice were perfused through the heart with PBS and tumors, and organs were collected. Quantification of fluorescence carried out with ImageJ software. Multiple sections from three tumors were analyzed (P<0.0001, Student's t-test).

Two compounds have been identified that bind to the LyP-1 receptor, p32, at the same site as LyP-1 (Paasonen et al., Chembiochem. 2016 Apr. 11; 17(7):570-575). In vivo tests of one of these compounds (#008) show that nanoparticles coated with the peptide specifically home to tumors (Paasonen et al., Chembiochem. 2016 Apr. 11; 17(7):570-575) and to plaques (FIG. 10). In the procedure, which was adapted from Paasonen et al., Chembiochem. 2016 Apr. 11; 17(7):570-575), orthotopic MCF10Ca1A breast tumors from mice injected with iron oxide NWs (7.5 mg/kg of Fe) coated with FAM-#008 (FIG. 4C) or with an inert peptide (control). The NWs were allowed to circulate for 5 hours, the mice were perfused through the heart with PBS and tumors, and organs were collected. FAM-labeled #008-NWs were injected (1 mg/ml, 200 µl, IV) into an atherosclerotic mouse. Plaque sections at aorta root level were collected for immunofluorescence analysis after two hours circulation followed by PBS perfusion. Sections of normal tissues from a mouse injected with #008-NWs show some NPs in the liver and a trace in the spleen, which non-specifically take up NPs.

Figure 11A:
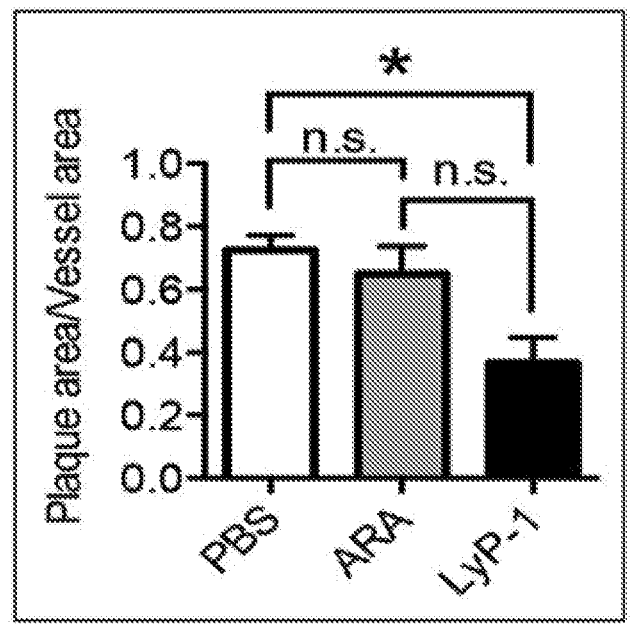
FIGS. 11A and 11B are graphs showing the effect of LyP-1 on carotid artery atherogenesis induced by arterial ligation. Carotid artery atherosclerotic plaque was induced in ApoE null mice by complete (A) or partial (B) ligation combined with high fat diet (HFD). The mice were treated with daily intravenous injections of PBS, or 200 μg of ARA (control peptide), or LyP-1 for 2 weeks. N=7 (A) and N=9 (B) per group. Statistical analysis: One-way Anova, followed by Kruskal-Wallis test. *, p<0.05.
Figure 11B:
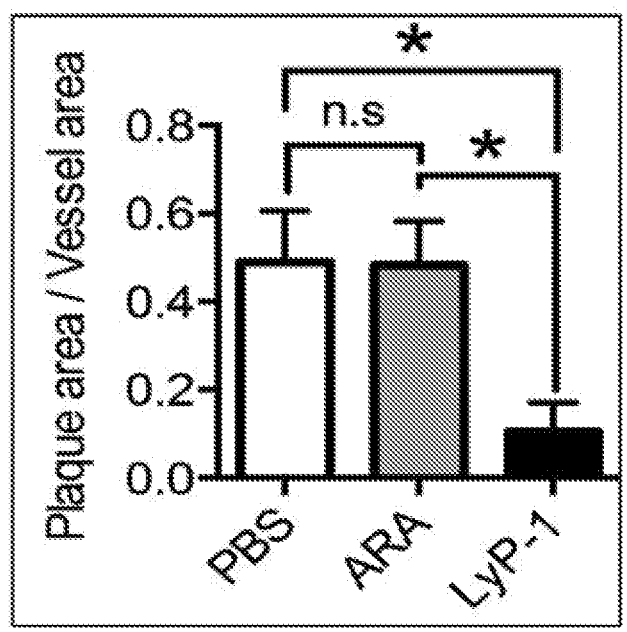
Figure 12A:
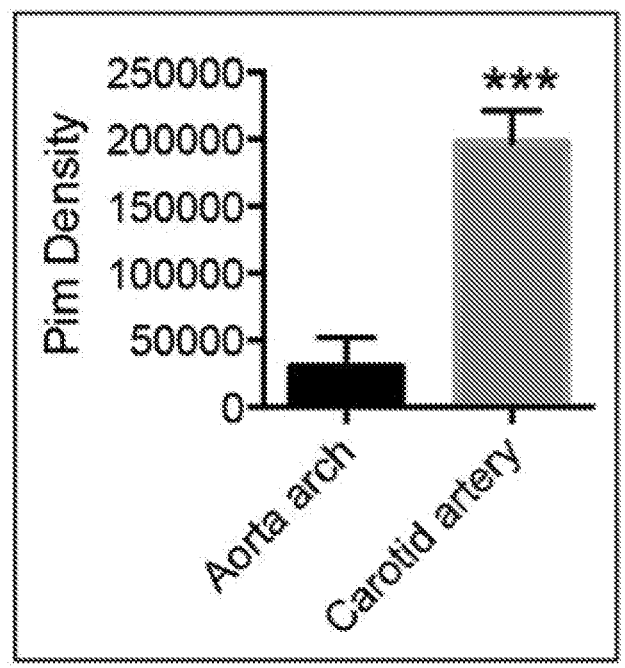
FIGS. 12A and 12B are graphs showing the effect of hypoxia in plaques. Carotid artery partial ligation was carried out on ApoE null mice after 16 weeks on HFD. Two weeks later, the mice had developed both aortic (HFD) and carotid artery plaque (HFD+ligation). The mice were intravenously injected with the hypoxia probe Pimonidazole (Pim) and the tissues were collected 90 min later, and sectioned for hypoxia (Pim) and blood vessel (CD31) staining. Shown is quantitative comparison of Pim staining density (A) and vascular area inside the plaque (B) in the two types of plaque. N=6; ***, P<0.005. She et al., Arteriosclerosis, thrombosis, and vascular biology. 2016; 36(1): 49-59.
Figure 12B:
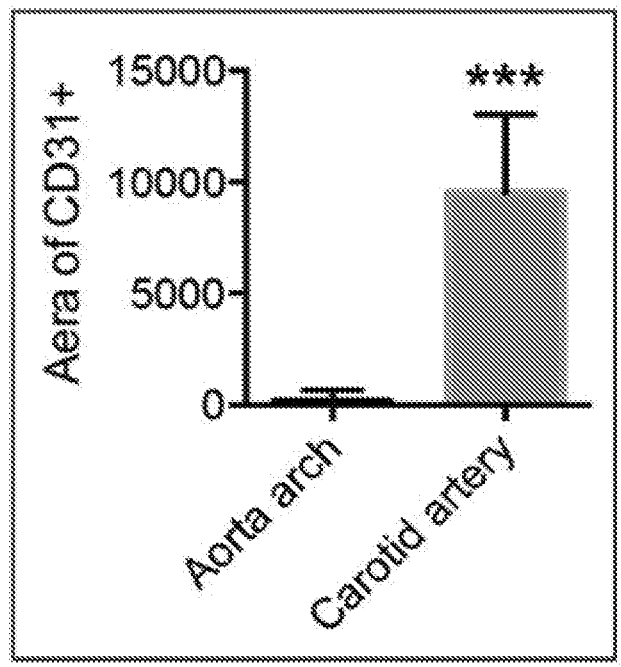

It was discovered that treatment with LyP-1 alone, without any drug, significantly (p<0.05) reduces plaque in two mouse models (FIG. 11; She et al., Arteriosclerosis, thrombosis, and vascular biology. 2016; 36(1):49-59). This striking plaque reduction was accomplished using complete and partial arterial ligation models in ApoE null mice. The mice develop abundant plaque in the carotid artery within a few weeks (Ruusalepp et al., Interactive cardiovascular and thoracic surgery. 2003; 2(2):196-200). LyP-1 was also tested in ApoE mice kept on a long-term (>16 weeks) HFD. The results indicate an inhibitory effect on aortic plaque by the peptide, but less robust than for carotid artery plaques. This difference might relate to a difference in the extent of hypoxia in aortic and carotid artery plaques (FIG. 12).

The LyP-1 effect on plaque is likely to be based on a pro-apoptotic effect of LyP-1 found on plaque macrophages (FIG. 13).

A pro-apoptotic effect by LyP-1 has also been observed on cultured RAW cells, but it was necessary to keep the cells under hypoxic conditions to see the effect, which is in agreement with the greater activity of LyP-1 on the hypoxic ligation-induced plaques. These results establish a direct anti-plaque activity by the LyP-1 peptide, thus providing a second mode for LyP-1 treatment of atherosclerosis.

High throughput drug screening was performed for compounds that inhibit the binding of LyP-1 to p32 in a florescence polarization (FP) assay (Paasonen et al., Chembiochem. 2016 Apr. 11; 17(7):570-575). Two of the hits from the screen passed all the specificity tests, and one of these has been characterized to some extent in vivo (FIG. 10). Importantly, this compound, #008, directs nanoparticle accumulation in plaques and is cytotoxic to plaque macrophages ex vivo. It was recognized that a small molecule with the same activities in plaques as LyP-1 would be a major advance because such a small molecule should display improved systemic pharmacokinetics, and therefore could be expected to be significantly more efficacious than the peptides. Moreover, it can serve as a lead compound for more potent, orally available compounds. Thus, the discovered compounds, especially #008 and #7933989, served as a starting point for other compounds with affinity for p32. Orally available compounds provide significant new opportunities in prevention and treatment of atherosclerosis.

Compounds can be tested for p32 binding in, for example, the FAM-LyP-1 FP assay (Paasonen et al., Chembiochem. 2016 Apr. 11; 17(7):570-575). For example, compounds with potency of <10 µM can be identified. Compounds can also be tested for apoptosis induction in plaque macrophages, and for in vivo plaque homing by using a functionality suitable fluorphor or nanoparticle coupling in the compound or that is added to the compound. Compounds can also be assessed for suitability for in vivo testing by a preliminary ADME (absorption, distribution, metabolism and excretion) analysis.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptides and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a", "an", and "the" include plural reference unless the context clearly dictates otherwise. Thus, for example, reference to "a compound" includes a plurality of such compounds, reference to "the compound" is a reference to one or more compounds and equivalents thereof known to those skilled in the art, and so forth.

The term "can," "can be," and related terms is intended to convey that the subject matter involved is optional (that is, the subject matter is present in some embodiments and is not present in other embodiments), not a reference to a capability of the subject matter or to a probability, unless the context clearly indicates otherwise.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different compounds or peptides does not indicate that the listed compounds or peptides are obvious one to the other, nor is it an admission of equivalence or obviousness.

Every compound disclosed herein is intended to be and should be considered to be specifically disclosed herein. Further, every subgroup that can be identified within this disclosure is intended to be and should be considered to be specifically disclosed herein. As a result, it is specifically contemplated that any compound, or subgroup of compounds can be either specifically included for or excluded from use or included in or excluded from a list of compounds. For example, as one option, a group of peptides is contemplated where each peptide is as described herein but is not LyP-1. As another example, a group of compounds is contemplated where each compound is as described herein and is able to home to atherosclerotic plaques. LyP-1 and TT1 can be independently and specifically included or excluded from the peptides and methods disclosed herein.

All publications mentioned herein are incorporated herein by reference in full for the purpose of describing and disclosing the databases, proteins, and methodologies, which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference. The publications, patents, patent applications, public databases, public database entries, and other references are cited for the purpose of describing and disclosing the information, databases, chemical compounds, proteins, and methodologies, which are described in the publications which might be used in connection with the presently described invention. The publications discussed anywhere herein are provided solely for their disclosure prior to the filing date of the present invention. Nothing herein is to be construed as an admission that the inventors are not entitled to antedate such disclosure by virtue of prior invention.

While in the foregoing specification, this invention has been described in relation to certain preferred embodiments thereof, and many details have been set forth for the purposes of illustration, it will be apparent to those skilled in the art that the invention is susceptible to additional embodiments and that certain of the details herein may be varied considerably without departing from the basic principles of the invention.

Although the invention has been described with reference to specific experiments and examples provided, it should be understood that various modifications can be made without departing from the spirit of the invention. One skilled in the art will be able to envision that the present invention encompasses the exemplary methods and compounds and use of the same as well as other aspects that are within the spirit of the invention.

Those skilled in the art will recognize, or be able to ascertain using no more than routine experimentation, many equivalents to the specific embodiments of the method and compositions described herein. Such equivalents are intended to be encompassed by the following claims.

We claim:

1. A composition comprising a plaque-homing element, a CendR-activating element, and a plaque-inhibiting element, wherein the plaque-homing element is $CX_aRGX_bRSX_cC$ (SEQ ID NO:3), wherein $X_a$ and $X_b$, are independently are any amino acid, and, independently, $X_c$ is any amino acid or is absent.

2. The composition of claim 1, wherein the CendR-activating element is a peptide.

3. The composition of claim 1, wherein the CendR-activating element is CGQKRTRGC (SEQ ID NO:2), GNK-RTR (SEQ ID NO:7), CKRGAR (SEQ ID NO:9), CKRGSR (SEQ ID NO:10), CKRGNR (SEQ ID NO:11), $CX_aRGX_bR$ (SEQ ID NO:13), KRGAR (SEQ ID NO:14), KRGSR (SEQ ID NO:15), KRGNR (SEQ ID NO:16), $RGX_bR$ (SEQ ID NO:12), $X_aRGX_bR$ (SEQ ID NO:17), RPARPAR (SEQ ID NO:18), a peptide with the sequence $X_1X_2X_3X_4$ at, or exposable at, the free C-terminal end of the peptide, wherein $X_1$ is R, K or H, wherein $X_4$ is R, K, H, or KG, and wherein $X_2$ and $X_3$ are each, independently, any amino acid), or an extended blood half-life LyP-1, wherein the extended blood half-life LyP-1 comprises the amino acid sequence GNK-RTR (SEQ ID NO:7), wherein $X_a$ and $X_b$ independently are any amino acid.

4. The composition of claim 1, wherein the plaque-inhibiting element is a peptide.

5. The composition of claim 1, wherein the plaque-inhibiting element is CGQKRTRGC (SEQ ID NO:2 or an extended blood half-life LyP-1, wherein the extended blood half-life LyP-1 comprises the amino acid sequence GNKRTR (SEQ ID NO:7).

6. The composition of claim 1, wherein one or more of the plaque-homing element, CendR-activating element, and plaque-inhibiting element is a peptide, wherein one or more of the one or more plaque-homing element, CendR-activating element, and plaque-inhibiting element that is a peptide conjugates to albumin in blood.

7. The composition of claim 1, wherein one or more of the plaque-homing element, CendR-activating element, and plaque-inhibiting element is a peptide, wherein one or more of the one or more plaque-homing element, CendR-activating element, and plaque-inhibiting element that is a peptide is conjugated to a lipid.

8. The composition of claim 1, wherein the composition is comprised in a micelle.

9. A method of treating atherosclerosis in a subject in need thereof, the method comprising administering a composition of claim 1 to the subject.

10. The method of claim 9, wherein the subject is at risk of atherosclerosis.

11. The method of claim 9, wherein the subject has atherosclerosis.

12. The composition of claim 1, wherein $X_a$ is K, V, T, R, A, or Q.

13. The composition of claim 1, wherein $X_a$ is K or T.

14. The composition of claim 1, wherein $X_a$ is K.

15. The composition of claim 1, wherein $X_b$ is A, S, G, N, T, or K.

16. The composition of claim 1, wherein $X_b$ is A, S, or N.

17. The composition of claim 1, wherein $X_b$ is A.

18. The composition of claim 1, wherein $X_c$ is T, S, K, A, V, R, L, or absent.

19. The composition of claim 1, wherein $X_c$ is T, S, or K.

20. The composition of claim 1, wherein $X_c$ is T.

21. The composition of claim 1, wherein $X_a$ is K, V, T, R, A, or Q, $X_b$ is A, S, G, N, T, or K, and $X_c$ is T, S, K, A, V, R, L, or absent.

22. The composition of claim 1, wherein $X_a$ is K or T, $X_b$ is A, S, or N, and $X_c$ is T, S, or K.

23. The composition of claim 1, wherein $X_a$ is K, $X_b$ is A, and $X_c$ is T.

* * * * *